United States Patent
Zhang et al.

(10) Patent No.: US 11,407,760 B2
(45) Date of Patent: Aug. 9, 2022

(54) DIOXINOQUINOLINE COMPOUNDS, PREPARATION METHOD AND USES THEREOF

(71) Applicant: BEIJING SCITECH-MQ PHARMACEUTICALS LIMITED, Beijing (CN)

(72) Inventors: Qiang Zhang, Beijing (CN); Shannan Yu, Beijing (CN); Zhongxiang Wang, Beijing (CN); Shouye Feng, Beijing (CN); Yueming Sun, Beijing (CN); Yansheng Liu, Beijing (CN); Hongbo Zhang, Beijing (CN); Leifu Yang, Beijing (CN); Hailong Yang, Beijing (CN); Likai Zhou, Beijing (CN); Nanqiao Zheng, Beijing (CN); Chenming Hu, Beijing (CN); Zhanqiang Xu, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 0 days.

(21) Appl. No.: 16/968,797

(22) PCT Filed: Jan. 25, 2019

(86) PCT No.: PCT/CN2019/073260
§ 371 (c)(1),
(2) Date: Aug. 10, 2020

(87) PCT Pub. No.: WO2019/154133
PCT Pub. Date: Aug. 15, 2019

(65) Prior Publication Data
US 2020/0399285 A1    Dec. 24, 2020

(30) Foreign Application Priority Data
Feb. 11, 2018    (WO) ............... PCT/CN2018/076233
Aug. 27, 2018    (CN) .......................... 201810983341.3

(51) Int. Cl.
C07D 491/056    (2006.01)
A61P 35/02    (2006.01)
A61P 35/04    (2006.01)
A61P 35/00    (2006.01)

(52) U.S. Cl.
CPC ............................... C07D 491/056 (2013.01)

(58) Field of Classification Search
CPC ................................................ C07D 491/056
See application file for complete search history.

(56) References Cited

U.S. PATENT DOCUMENTS

| | | |
|---|---|---|
| 8,664,244 B2 | 3/2014 | Chen |
| 10,106,508 B2 | 10/2018 | Sheng et al. |
| 2016/0220554 A1 | 8/2016 | Smith et al. |

FOREIGN PATENT DOCUMENTS

| | | |
|---|---|---|
| CN | 1553899 A | 12/2004 |
| CN | 103328447 A | 9/2013 |
| CN | 103402505 A | 11/2013 |
| CN | 104530063 A | 4/2015 |
| CN | 105541798 A | 5/2016 |
| CN | 105837586 A | 8/2016 |
| WO | 2005/030140 A2 | 4/2005 |
| WO | 2018/153293 A1 | 8/2018 |

OTHER PUBLICATIONS

Stella (J. Pharmaceutical Sciences, 2010, 99(12), pp. 4755-4765).*
Cui et al., Targeting receptor tyrosine kinase MET in cancer: small molecule inhibitors and clinical progress. J Med Chem. Jun. 12, 2014;57(11):4427-53.
Qin et al., Discovery of new [1,4]dioxino[2,3-f]quinazoline-based inhibitors of EGFR including the T790M/L858R mutant. Bioorg Med Chem. Jul. 1, 2016;24(13):2871-2881.
Zhan et al., Discovery of Anilinopyrimidines as Dual Inhibitors of c-Met and VEGFR-2: Synthesis, SAR, and Cellular Activity. ACS Med Chem Lett. Mar. 26, 2014;5(6):673-8.
International Search Report and Written Opinion for Application No. PCT/CN2019/073260, dated Apr. 26, 2019, 12 pages.

* cited by examiner

Primary Examiner — Susanna Moore
(74) Attorney, Agent, or Firm — McCarter & English, LLP; Xin Zhang; Xiaoyuan Ding

(57) ABSTRACT

The present invention relates to a dioxinoquinoline compound of formula (I) or a pharmaceutically acceptable salt thereof. The invention also provides a preparation method of the compound of formula (I) and a pharmaceutically acceptable salt thereof, as well as uses thereof as a drug, wherein the drug acting as a tyrosine kinase (i.e. VEGFR-2 and c-MET) inhibitor is used for treating disorders related to tyrosine kinase.

Formula (I)

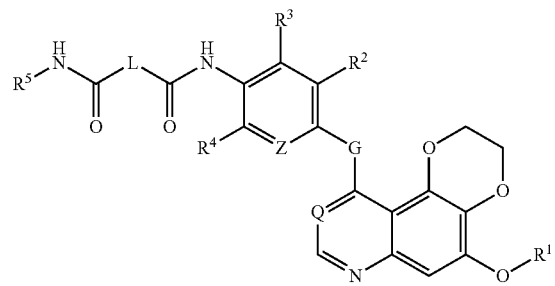

23 Claims, No Drawings

DIOXINOQUINOLINE COMPOUNDS, PREPARATION METHOD AND USES THEREOF

CROSS REFERENCE TO RELATED APPLICATIONS

The present application is a national application of PCT/CN2019/073260 filed on Jan. 25, 2019, which claims the priority of the PCT Application No. PCT/CN2018/076233 filed on Feb. 11, 2018, and the Chinese Patent Application No. 201810983341.3 filed on Aug. 27, 2018. The PCT Application No. PCT/CN2018/076233 and the Chinese Patent Application No. 201810983341.3 are incorporated herein by reference as part of the disclosure of the present application.

TECHNICAL FIELD

The present disclosure relates to a dioxinoquinoline compound, or a pharmaceutically acceptable salt, an isomer, a hydrate, a solvate, or a prodrug thereof, as well as the preparation method and use thereof.

BACKGROUND

Receptor tyrosine kinases (RTKs) cross cell membranes and affect the trans-cellular membrane transmission of biochemical signals. They are consisted of three parts: an extracellular domain containing a ligand binding site, a single transmembrane region, and an intracellular domain containing the activity of tyrosine protein kinase. The binding of a ligand to a receptor stimulates the activity of the relevant receptor tyrosine kinase, which leads to the phosphorylation of tyrosine residues on the receptor and other intracellular molecules, which in turn triggers cascade signals that cause various cellular responses. The overexpression of tyrosine receptor activates downstream signal transduction pathways, which ultimately leads to abnormal transformation and proliferation of cells, and promotes the occurrence and development of tumors.

A vascular endothelial growth factor receptor (VEGFR) is a member of the receptor tyrosine kinase family. It binds to its ligand, vascular endothelial growth factor (VEGF), to produce a series of biochemical and physiological processes, which ultimately promote the formation of new blood vessels. The formation and permeability of tumor blood vessels are mainly regulated by vascular endothelial growth factor (VEGF), which acts through at least two different receptors (VEGFR-1, VEGFR-2). According to studies by Jakeman, Kolch, Connolly, etc., VEGF is an important stimulus for normal and pathological angiogenesis and vascular permeability (Jakeman et al., 1993, Endocrinology 133: 848-859; Kolch et al., 1995, Breast Cancer Research and Treatment, 36:139-155; Connolly et al., 1989, J. Biol. Chem. 264: 20017-20024). Vascular endothelial cell growth factor induces vascular sprouting phenotype by inducing endothelial cell proliferation, protease expression, and migration of cell tissues that subsequently form capillary. Therefore, the antagonism of VEGF produced by the chelation of VEGF by antibodies can lead to the inhibition of tumor growth (Kim et al., 1993, Nature 362: 841-844).

Because VEGFR-2 is mainly distributed in vascular endothelial cells, it can bind to VEGF-A, VEGF-C, VEGF-D, and VEGF-E. However, the effects of VEGF on stimulating endothelial cell proliferation, increasing the permeability of blood vessels and increasing the formation of new blood vessels are mainly achieved by binding and activating VEGFR-2. If the activity of VEGFR-2 is blocked, the growth and metastasis of tumors can be inhibited through direct and indirect pathways, thereby achieving ideal anti-tumor effect. Therefore, the search for small molecular inhibitors with high activity and high selectivity for VEGFR-2 has become a very promising strategy for the tumor treatment.

A hepatocyte growth factor receptor (c-MET) is a kind of tyrosine kinase receptors, the abnormal activation of which plays an important role in the occurrence and development of various malignant tumors including lung cancer. A hepatocyte growth factor (HGF) is a specific ligand for c-MET, and c-MET binds to HGF to play a biological role through HGF/c-MET signaling pathway. The HGF/c-MET signaling pathway can induce a series of biological effects such as cell proliferation, dispersion, migration, organ morphogenesis, and angiogenesis. Abnormal activation of c-MET can manifest as receptor overexpression, gene mutation, amplification, translocation, rearrangement, etc. These changes can lead to dysregulation of downstream signaling pathways, such as serine/threonine protein kinase (AKT), extracellular signaling kinase (ERK), phosphatidylinositol-3-hydroxykinase, and retinoblastoma inhibitory protein (Rb), thereby mediating processes such as tumorigenesis, invasion and metastasis, angiogenesis, and epithelial-mesenchymal transition. c-MET plays an important role in cell proliferation, metabolism, tumor generation, metastasis, and angiogenesis, and has become an important target for the anti-tumor therapy. Targeted therapy with c-MET as the target has shown great significance in the treatment of various malignant tumors including lung cancer.

During the treatment with anti-tumor drugs, the interaction of multiple signaling pathways will affect the effect of anti-tumor drugs. For example, the interaction of the HFG/c-MET signaling pathway with other pathways affects the therapeutic effect of anti-tumor drugs and produces drug resistance. Therefore, drug combination against multiple kinase targets has become a new anti-tumor therapy. Moreover, the successful marketing of Crizotinib and Cabozantinib shows that the development of inhibitors for multiple kinase targets has good potential and application value.

Cabozantinib is a small molecular inhibitor of protein kinase, which can inhibit c-MET, VEGFR-2, Ret, Kit, AXL and other kinases. Cabozantinib can inhibit the phosphorylation of c-MET and VEGFR-2 in tumor models, and shows effective activity of anti-tumor metastasis and anti-angiogenesis in preclinical drug efficacy models. Compared with an inhibitor that acts on VEGFR target alone, no increase in tumor burden was found in the lung tumor metastasis model treated with Cabozantinib, indicating that Cabozantinib is an effective inhibitor of tumor angiogenesis and metastasis in tumor patients with dysregulated c-MET and VEGFR-2 signaling pathways. The FDA approved the marketing of Cabozantinib on Nov. 29, 2012 for the treatment of patients with progressive, metastatic medullary thyroid carcinoma (MTC).

Inhibitors like Cabozantinib that act on multiple targets have many advantages, and thus there are many researches on this type of inhibitor. At present, there are few such drugs on the market, the drug availability is limited, and the drugs that have been marketed encounter problems such as drug resistance and side effects during use. Therefore, compared with marketed inhibitors against single target, small molecular inhibitors for multiple targets will have better therapeutic effects and application prospects.

SUMMARY

The present disclosure provides a compound of formula (I), or a pharmaceutically acceptable salt, an isomer, a hydrate, a solvate, or a prodrug thereof, which can be used to treat or prevent diseases caused by tyrosine kinases (e.g., VEGFR-2 and/or c-MET), including some variants of tyrosine kinase receptors, Formula (I)

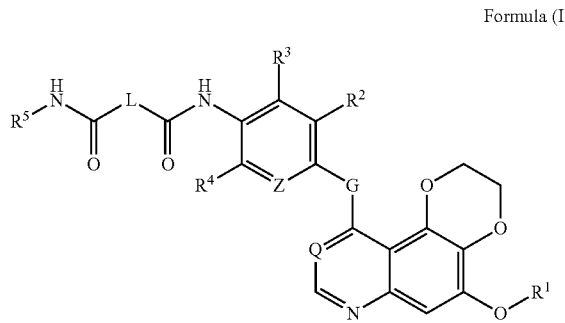

in the formula (I),
Q is CH;
G is O;
Z is CH;
L is selected from the group consisting of

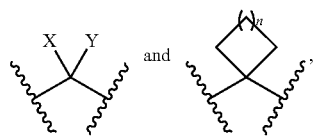

wherein X is H or $C_1$-$C_3$ alkyl; Y is H or $C_1$-$C_3$ alkyl; n is 0 to 3, and when n is 0, L represents

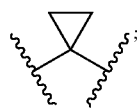 [SMILES: *C1(*)CC1]

$R^1$ is H, $C_1$-$C_9$ alkyl, $C_3$-$C_7$ cycloalkyl, 4- to 7-membered heterocyclyl, $C_1$-$C_6$ alkyl substituted with $C_3$-$C_7$ cycloalkyl, $C_1$-$C_6$ alkyl substituted with 4- to 7-membered heterocyclyl, or $C_1$-$C_9$ alkyl substituted with one or more of the following: hydroxyl, $C_1$-$C_6$ alkoxy, $C_1$-$C_6$ alkylthio and —$NR^6R^7$, $R^6$ and $R^7$ are each independently H, $C_1$-$C_6$ alkyl, $C_1$-$C_6$ alkyl substituted with hydroxyl, or $C_1$-$C_6$ alkyl substituted with $C_1$-$C_3$ alkoxy;

the above 4- to 7-membered heterocyclyl is a 4- to 7-membered heterocyclyl containing 1 to 2 atoms selected from the group consisting of N, O, and S, which is unsubstituted, or is substituted with $C_1$-$C_3$ alkyl or $C_1$-$C_3$ acyl, or is oxidized by 1 to 2 oxygen atoms;

$R^2$ is H, $C_1$-$C_3$ alkyl or halogen;
$R^3$ is H, $C_1$-$C_3$ alkyl or halogen;
$R^4$ is H, $C_1$-$C_3$ alkyl or halogen;

$R^5$ is H, $C_1$-$C_9$ alkyl, $C_3$-$C_7$ cycloalkyl, $C_1$-$C_6$ alkyl substituted with $C_3$-$C_7$ cycloalkyl, aryl, $C_1$-$C_6$ alkyl substituted with aryl, heteroaryl, or $C_1$-$C_6$ alkyl substituted with heteroaryl;

the aryl and heteroaryl are unsubstituted, or substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl, aryloxy and methylsulfonyl; and the heteroaryl is a monocyclic or bicyclic group containing 1 to 3 heteroatoms selected from the group consisting of N, O, and S, and containing 5 to 10 ring atoms.

According to an alternative embodiment, $R^1$ is H, $C_1$-$C_6$ alkyl, $C_3$-$C_6$ cycloalkyl, 5- to 6-membered heterocyclyl, $C_1$-$C_3$ alkyl substituted with $C_3$-$C_6$ cycloalkyl, $C_1$-$C_3$ alkyl substituted with 5- to 6-membered heterocyclyl, or $C_1$-$C_6$ alkyl substituted with the following: hydroxyl, $C_1$-$C_3$ alkoxy, $C_1$-$C_3$ alkylthio or —$NR^6R^7$, $R^6$ and $R^7$ are each independently —H, $C_1$-$C_3$ alkyl, $C_1$-$C_3$ alkyl substituted with hydroxyl, or $C_1$-$C_3$ alkyl substituted with $C_1$-$C_3$ alkoxy; and the above 5- to 6-membered heterocyclyl is a 5- to 6-membered heterocyclyl containing 1 to 2 atoms selected from the group consisting of N, O, and S, which is unsubstituted, or is substituted with $C_1$-$C_3$ alkyl or $C_1$-$C_3$ acyl, or is oxidized by 1 to 2 oxygen atoms.

According to an alternative embodiment, $R^1$ is selected from the group consisting of one or more of the following: methyl, ethyl, propyl, isopropyl, methoxyethyl, methoxypropyl, methoxybutyl, methoxypentyl, methoxyhexyl, tetrahydrofuran-3-yl, tetrahydro-2H-pyran-4-yl, tetrahydropyrrol-1-ylethyl, tetrahydropyrrol-1-ylpropyl, piperidin-1-ylethyl, piperidin-1-ylpropyl, piperazin-1-ylethyl, piperazin-1-ylpropyl, morpholin-4-ylethyl, morpholin-4-ylpropyl, methylpiperazin-4-ylethyl, methylpiperazin-4-ylpropyl, N-formylpiperazin-4-ylethyl, N-formylpiperazin-4-ylpropyl, N-acetylpiperazin-4-ylethyl, N-acetylpiperazin-4-ylpropyl, (1,1-dioxothiomorpholin)-4-ylethyl, (1,1-dioxothiomorpholin)-4-ylpropyl, methylthioethyl, methylthiopropyl, dimethylaminoethyl, dimethylaminopropyl, dimethylaminobutyl, dimethylaminopentyl, dimethylaminohexyl, diethylaminoethyl, diethylaminopropyl, hydroxyethyl, hydroxypropyl, hydroxyethylaminoethyl, hydroxypropylaminoethyl, hydroxyethylaminopropyl, methoxyethylaminoethyl, methoxypropylaminoethyl, methoxyethylaminopropyl, aminoethyl, aminopropyl, aminobutyl, N-methyl-N-hydroxyethylaminoethyl, N-methyl-N-hydroxypropylaminoethyl, N-methyl-N-hydroxyethylaminopropyl, N-methyl-N-methoxyethylaminoethyl, N-methyl-N-methoxypropylaminoethyl, N-methyl-N-methoxyethylaminopropyl, 2-methyl-2-hydroxypropyl, 3-methyl-3-hydroxybutyl, (3S)-3-aminobutyl, (3R)-3-aminobutyl, (3S)-3-hydroxybutyl or (3R)-3-hydroxybutyl.

According to an alternative embodiment, $R^1$ is selected from the group consisting of butyl, isobutyl, pentyl, isopentyl, hexyl, cyclopropylmethyl, cyclopropylethyl, cyclopropylpropyl, cyclobutylmethyl, cyclobutylethyl, cyclobutylpropyl, 4,4-dimethylpiperidin-1-ylethyl, 4,4-dimethylpiperidin-1-ylpropyl, and oxetan-3-yl.

According to an alternative embodiment, the halogen described in $R^2$, $R^3$, and $R^4$ is Cl or F.

According to an alternative embodiment, $R^5$ is —H, $C_1$-$C_6$ alkyl, $C_3$-$C_6$ cycloalkyl, $C_1$-$C_3$ alkyl substituted with $C_3$-$C_6$ cycloalkyl, aryl, $C_1$-$C_3$ alkyl substituted with aryl, heteroaryl, or $C_1$-$C_3$ alkyl substituted with heteroaryl, wherein the aryl and heteroaryl are substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl, aryloxy and methylsulfonyl; and the heteroaryl is a monocyclic or bicyclic group containing 1 to 2 heteroatoms selected from the group consisting of N, O, and S, and containing 5 to 10 ring atoms.

Yet alternatively, $R^5$ is selected from the group consisting of H, methyl, ethyl, propyl, isopropyl, isopentyl, cyclopropyl, cyclobutyl, cyclopentyl, cyclohexyl, phenyl, 4-fluorophenyl, 3-fluorophenyl, 2-fluorophenyl, 4-chlorophenyl, 3-chlorophenyl, 2-chlorophenyl, 2,4-difluorophenyl, 2,5-difluorophenyl, 3,4-difluorophenyl, 2,4-dichlorophenyl, 2,5-dichlorophenyl, 3,4-dichlorophenyl, 2-fluoro-4-(trifluoromethyl)phenyl, 2-fluoro-5-(trifluoromethyl)phenyl, 3-fluoro-4-(trifluoromethyl)phenyl, 3-fluoro-5-(trifluoromethyl)phenyl, 3-(trifluoromethyl)-4-fluorophenyl, 2-fluoro-4-chlorophenyl, 2-fluoro-5-chlorophenyl, 3-fluoro-4-chlorophenyl, 3-fluoro-5-chlorophenyl, 3-chloro-4-fluorophenyl, 2-chloro-4-(trifluoromethyl)phenyl, 2-chloro-5-(trifluoromethyl)phenyl, 3-chloro-4-(trifluoromethyl)phenyl, 3-chloro-5-(trifluoromethyl)phenyl, 3-(trifluoromethyl)-4-chlorophenyl, 2-chloro-4-fluorophenyl, 2-chloro-5-fluorophenyl, 3-chloro-4-fluorophenyl, benzyl, phenethyl, 4-fluorobenzyl, naphthalen-1-yl, 3-methylisoxazol-5-yl, 4-phenoxyphenyl, 3-(methylsulfonyl)phenyl, 4-(methylsulfonyl)phenyl, pyridin-2-yl, pyridin-3-yl, pyridin-4-yl, 3-methoxybenzyl or 4-methoxybenzyl.

The present application also provides a compound of formula (I), or a pharmaceutically acceptable salt, an isomer, a hydrate, a solvate, or a prodrug thereof, Formula (I)

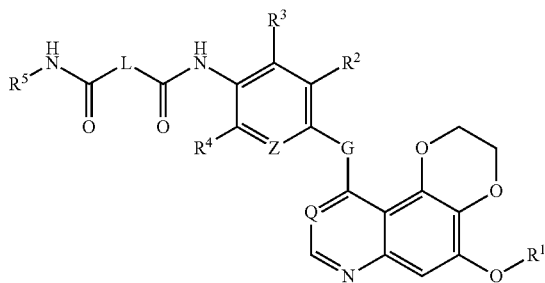

in the formula (I),
Q is CH;
G is O;
Z is CH;
L is selected from the group consisting of

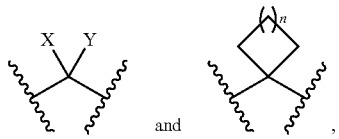
and wherein X is H or $C_1$-$C_3$ alkyl; Y is H or $C_1$-$C_3$ alkyl; n is 0 to 3, and when n is 0, L represents;

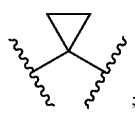 [SMILES: *C1(*)CC1]
;

$R^1$ is $C_1$-$C_6$ alkyl substituted with 1 to 3 substituents selected from the group consisting of $C_1$-$C_3$ acyl, halogen, trifluoromethyl, cyano, —$CONH_2$, —$NR^aR^b$ and 4- to 7-membered heteroalicyclic group, wherein the 4- to 7-membered heteroalicyclic group is a 4- to 7-membered heteroalicyclic group containing 1 to 2 atoms selected from the group consisting of N, O, and S as ring atoms, and the 4- to 7-membered heteroalicyclic group is substituted with 1 to 3 substituents selected from the group consisting of halogen, $C_1$-$C_3$ alkyl, hydroxyl, —$NH_2$, and $C_1$-$C_3$ acyl, $R^a$ and $R^b$ are each independently —H, $C_1$-$C_6$ alkyl, $C_3$-$C_6$ cycloalkyl, $C_1$-$C_6$ alkyl substituted with $C_1$-$C_3$ alkoxy, $C_1$-$C_6$ alkyl substituted with $C_1$-$C_3$ alkylthio, $C_1$-$C_6$ alkyl substituted with substituted amino or unsubstituted amino, wherein the substituted amino is substituted with mono- or di-$C_1$-$C_3$ alkyl;

$R^2$, $R^3$, and $R^4$ are each independently H, $C_1$-$C_3$ alkyl or halogen;

$R^5$ is —H, $C_1$-$C_9$ alkyl, $C_3$-$C_7$ cycloalkyl, $C_1$-$C_6$ alkyl substituted with $C_3$-$C_7$ cycloalkyl, aryl, $C_1$-$C_6$ alkyl substituted with aryl, heteroaryl, or $C_1$-$C_6$ alkyl substituted with heteroaryl;

the aryl and heteroaryl are unsubstituted, or are substituted with 1 to 3 substituents selected from the group consisting of one or more of the following: hydroxyl, amino, cyano, $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl, and methylsulfonyl; and the above heteroaryl is a monocyclic or bicyclic group containing 1 to 3 heteroatoms selected from the group consisting of N, O, and S and containing 5 to 10 ring atoms.

According to an alternative embodiment, $R^1$ is $C_1$-$C_6$ alkyl substituted with 1 to 3 substituents selected from the group consisting of $C_1$-$C_3$ acyl, —F, trifluoromethyl, cyano, —$CONH_2$, —$NR^aR^b$ and 4- to 7-membered heteroalicyclic group, wherein the 4- to 7-membered heteroalicyclic group is a 4- to 7-membered heteroalicyclic group containing 1 to 2 atoms selected from the group consisting of N, O, and S as ring atoms, and the 4- to 7-membered heteroalicyclic group is substituted with 1 to 3 substituents selected from the group consisting of —F, $C_1$-$C_3$ alkyl, hydroxyl, —$NH_2$, and $C_1$-$C_3$ acyl, $R^a$ and $R^b$ are each independently —H, $C_1$-$C_3$ alkyl, $C_3$-$C_6$ cycloalkyl, $C_1$-$C_3$ alkyl substituted with $C_1$-$C_3$ alkoxy, $C_1$-$C_3$ alkyl substituted with $C_1$-$C_3$ alkylthio, $C_1$-$C_3$ alkyl substituted with substituted amino or unsubstituted amino, wherein the substituted amino is substituted with mono- or di-$C_1$-$C_3$ alkyl;

$R^2$, $R^3$ and $R^4$ are each independently —H, —F or —Cl;

$R^5$ is —H, aryl, $C_1$-$C_3$ alkyl substituted with aryl, heteroaryl, or $C_1$-$C_3$ alkyl substituted with heteroaryl, wherein the aryl and heteroaryl are unsubstituted, or are substituted with 1 to 3 substituents selected from the group consisting of one or more of the following: hydroxyl, amino, cyano, $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl and methylsulfonyl; and the heteroaryl is a monocyclic or bicyclic group containing 5 to 10 ring atoms and containing 1 to 2 heteroatoms selected from the group consisting of N, O, and S.

Yet alternatively, $R^1$ is selected from the group consisting of cyanomethyl, cyanoethyl, cyanopropyl, —$CH_2CONH_2$, —$CH_2CF_3$,

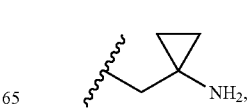

4-methyl-4-hydroxypiperidin-1-ylpropyl, 4-methyl-4-hydroxypiperidin-1-ylethyl, 4-methyl-4-aminopiperidin-1-ylpropyl, 4-methyl-4-aminopiperidin-1-ylethyl, N-methyl-N-cyclobutylaminopropyl, N-methyl-N-cyclopropylaminopropyl, N-methyl-N-cyclopentylaminopropyl, N-methyl-N-cyclohexylaminopropyl, N-methyl-N-cyclobutylaminoethyl, N-methyl-N-cyclopropylaminoethyl, N-methyl-N-cyclopentylaminoethyl, and N-methyl-N-cyclohexylaminoethyl.

The present disclosure provides a pharmaceutically acceptable salt of the compound of formula (I), wherein the salt is an acidic/anionic salt or a basic/cationic salt; the pharmaceutically acceptable acidic/anionic salt usually takes the form of protonating basic nitrogen(s) in them with inorganic or organic acids. Representative organic or inorganic acids include hydrochloric acid, hydrobromic acid, hydroiodic acid, perchloric acid, sulfuric acid, nitric acid, phosphoric acid, formic acid, acetic acid, propionic acid, glycolic acid, lactic acid, succinic acid, maleic acid, tartaric acid, malic acid, citric acid, fumaric acid, gluconic acid, benzoic acid, mandelic acid, methanesulfonic acid, isethionic acid, benzenesulfonic acid, oxalic acid, palmitic acid, 2-naphthalenesulfonic acid, p-toluenesulfonic acid, cyclohexylsulfamic acid, salicylic acid, hexonic acid, trifluoroacetic acid. Pharmaceutically acceptable basic/cationic salts include but are not limited to salts of aluminum, calcium, chloroprocaine, choline, diethanolamine, ethylenediamine, lithium, magnesium, potassium, sodium and zinc.

The present disclosure provides a method of preparing the above compound or a pharmaceutically acceptable salt, an isomer, a hydrate, a solvate, or a prodrug thereof, characterized in that the method includes the step of reacting the compound of formula (II') with the compound of formula (III') to afford the compound of formula (I), wherein Q, G, Z, L, $R^1$, $R^2$, $R^3$, $R^4$ and $R^5$ are as defined above,

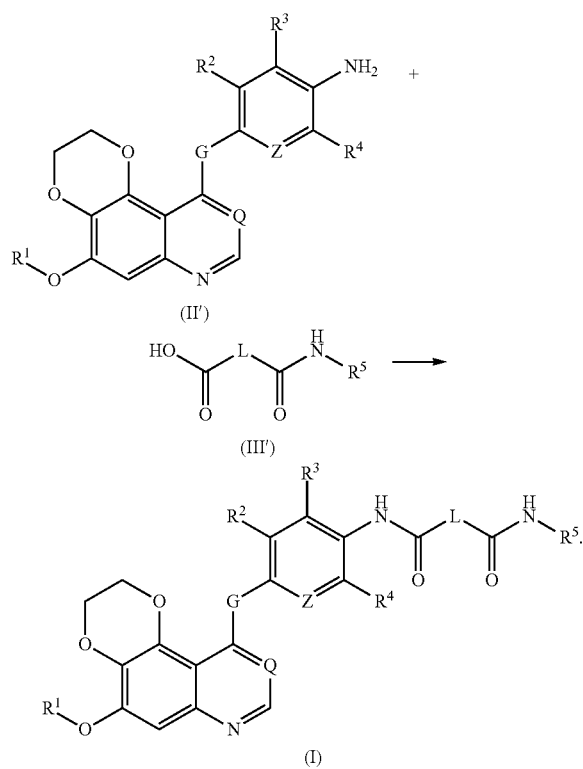

The present disclosure provides a method of preparing the above compound or a pharmaceutically acceptable salt, an isomer, a hydrate, a solvate, or a prodrug thereof, characterized in that the method includes the step of reacting the compound of formula (II') with the compound of formula (III) to afford the compound of formula (I), wherein Q, G, Z, L, R, $R^2$, $R^3$, $R^4$ and $R^5$ are as defined above,

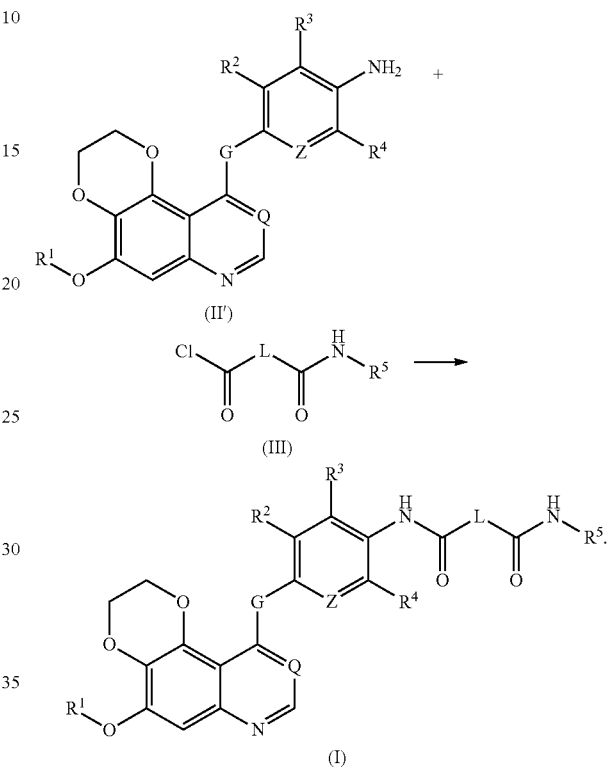

The present disclosure provides an intermediate for preparing the above compound, i.e., a compound of formula (II'), wherein Q, G, Z, $R^1$, $R^2$, $R^3$, and $R^4$ are as defined above,

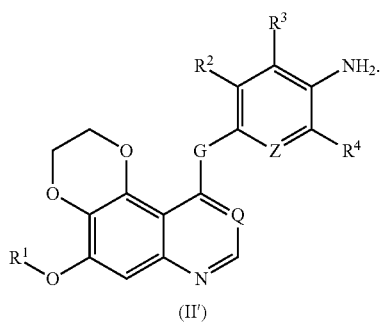

DETAILED DESCRIPTION OF THE EMBODIMENTS

Unless otherwise stated, the following terms used in this application (including the specification and claims) have the definitions given below. In this application, the use of "or" or "and" means "and/or" unless stated otherwise. In addition, the use of the term "comprising" and other forms such as "including", "containing" and "having" is not limiting. The chapter headings used herein are for organizational purposes only and should not be interpreted as limitations on the topics described.

The term "substituted" as used herein, includes multiple substituents (e.g., phenyl, aryl, heteroalkyl, heteroaryl), preferably 1 to 5 substituents, more preferably 1 to 3 substituents, most preferably 1 or 2 substituents, independently selected from the list of substituents.

Unless otherwise specified, alkyl includes saturated linear and branched hydrocarbon group, $C_1$-$C_9$ represents the number of carbon atoms of an alkyl is 1-9. Similarly, for example, $C_1$-$C_3$ represents the number of carbon atoms of an alkyl is 1-3, e.g., $C_1$-$C_6$ alkyl includes methyl, ethyl, propyl, isopropyl, n-butyl, isobutyl, sec-butyl, tert-butyl, n-pentyl, 3-(2-methyl)butyl, 2-pentyl, 2-methylbutyl, neopentyl, n-hexyl, 2-hexyl, and 2-methylpentyl, etc. An alkoxy group is an alkyl-O— group formed from a linear or branched alkyl group described previously and —O—. Similarly, alkenyl and alkynyl groups include linear or branched alkenyl or alkynyl groups.

Cycloalkyl refers to a cyclic group formed by carbon atoms. For example, $C_3$-$C_7$ cycloalkyl may include cyclopropyl, cyclobutyl, cyclopentyl, cyclohexyl, and cycloheptyl. Similarly, cyclic alkenyl group is also included herein.

The term "aryl" as used herein, unless otherwise specified, refers to an unsubstituted or substituted aromatic group, such as phenyl, naphthyl, anthracenyl.

"Oxidized by one or two oxygen atoms" refers to a sulfur atom oxidized by one oxygen atom to form a double bond between the sulfur and oxygen, or oxidized by two oxygen atoms to form double bonds between the sulfur and two oxygen atoms.

The term "heterocyclyl" as used herein, unless otherwise specified, represents an unsubstituted or substituted stable 3 to 8 membered monocyclic saturated ring system consisting of carbon atoms and 1 to 3 heteroatoms selected from N, O, and S, wherein the N, S heteroatoms can be optionally oxidized, and the N heteroatoms can also be optionally quaternized. Examples of such heterocyclyl rings include, but are not limited to, azetidinyl, pyrrolidinyl, tetrahydrofuranyl, tetrahydrothiazolyl, tetrahydropyranyl, morpholinyl, thiomorpholinyl, piperidinyl, piperazinyl, oxopiperazinyl, oxopiperidinyl, dioxolanyl, dioxanyl, tetrahydroimidazolyl, tetrahydrooxazolyl, thiamorpholinyl sulfoxide, thiomorpholine sulfone and oxadiazolyl.

The term "heteroaryl" as used herein, unless otherwise specified, represents an unsubstituted or substituted stable 5 or 6 membered monocyclic aromatic ring system, and may also represent unsubstituted or substituted 9 or 10-membered benzo-fused heteroaromatic ring system or a bicyclic heteroaromatic ring system consisting of carbon atoms and one to three heteroatoms selected from N, O, S, wherein the N, S heteroatoms may optionally be oxidized, and N heteroatoms may optionally be quaternized. Heteroaryl can be attached at any heteroatom or carbon atom to form a stable structure. Heteroaryl includes but is not limited to thienyl, furyl, imidazolyl, pyrrolyl, thiazolyl, oxazolyl, isoxazolyl, pyranyl, pyridinyl, piperazinyl, pyrimidinyl, pyrazinyl, pyridazinyl, pyrazolyl, thiadiazolyl, triazolyl, indolyl, azaindolyl, indazolyl, azaindazolyl, benzimidazolyl, benzofuryl, benzothienyl, benzoisoxazolyl, benzoxazolyl, benzopyrazolyl, benzothiazolyl, benzothiadiazolyl, benzotriazolyl, adeninyl, quinolinyl, or isoquinolinyl.

The term "carbonyl" refers to a —C(O)— group.

Whenever the terms "alkyl" or "aryl" or either of their prefix roots appear in the name of a substituent (eg, aralkyl, dialkylamino), it shall be interpreted to contain those limitations given for the above "alkyl" and "aryl". Designated numbers of carbon atoms (e.g., $C_1$-$C_6$) shall independently represent the number of carbon atoms in an alkyl moiety or an alkyl moiety in a larger substituent (wherein the alkyl group is the prefix root).

The present disclosure also provides methods for preparing corresponding compounds. Various synthetic methods can be used to prepare the compounds described herein, including the following methods. The compound disclosed herein or a pharmaceutically acceptable salt, an isomer or a hydrate thereof can be synthesized using the following methods and synthetic methods known in the field of organic chemical synthesis, or by variations of these methods as understood by those skilled in the art. Preferred methods include, but are not limited to, the following methods.

In one embodiment, the compound of formula (I) disclosed herein is prepared by reacting the compound of formula (II') with the compound of formula (III') or formula (III), wherein Q, G, Z, L, $R^1$, $R^2$, $R^3$, $R^4$ and $R^5$ are as described above.

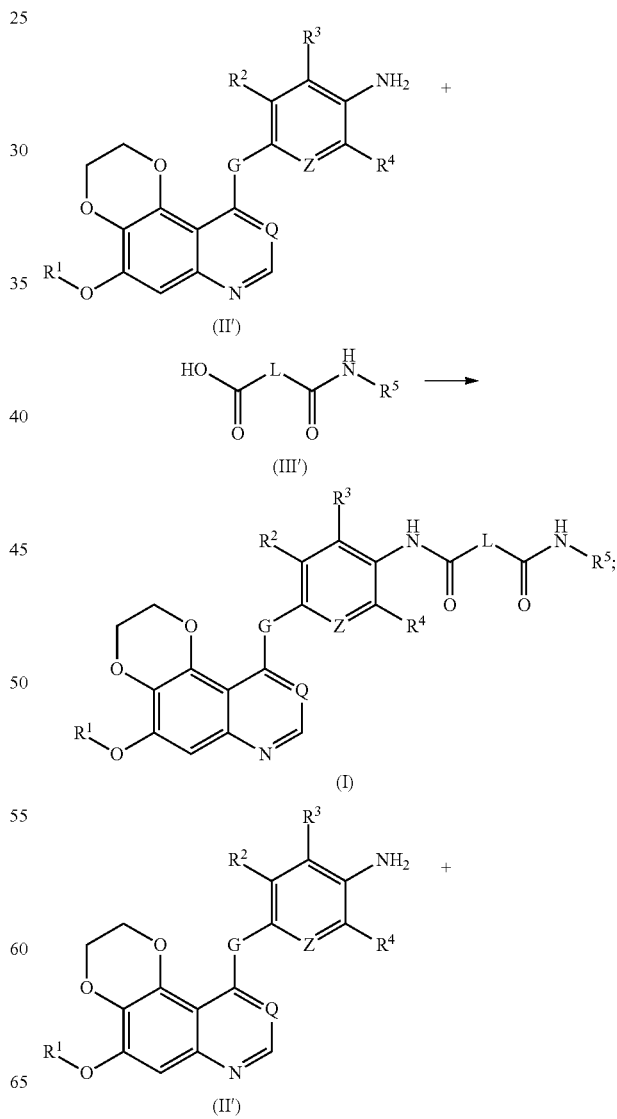

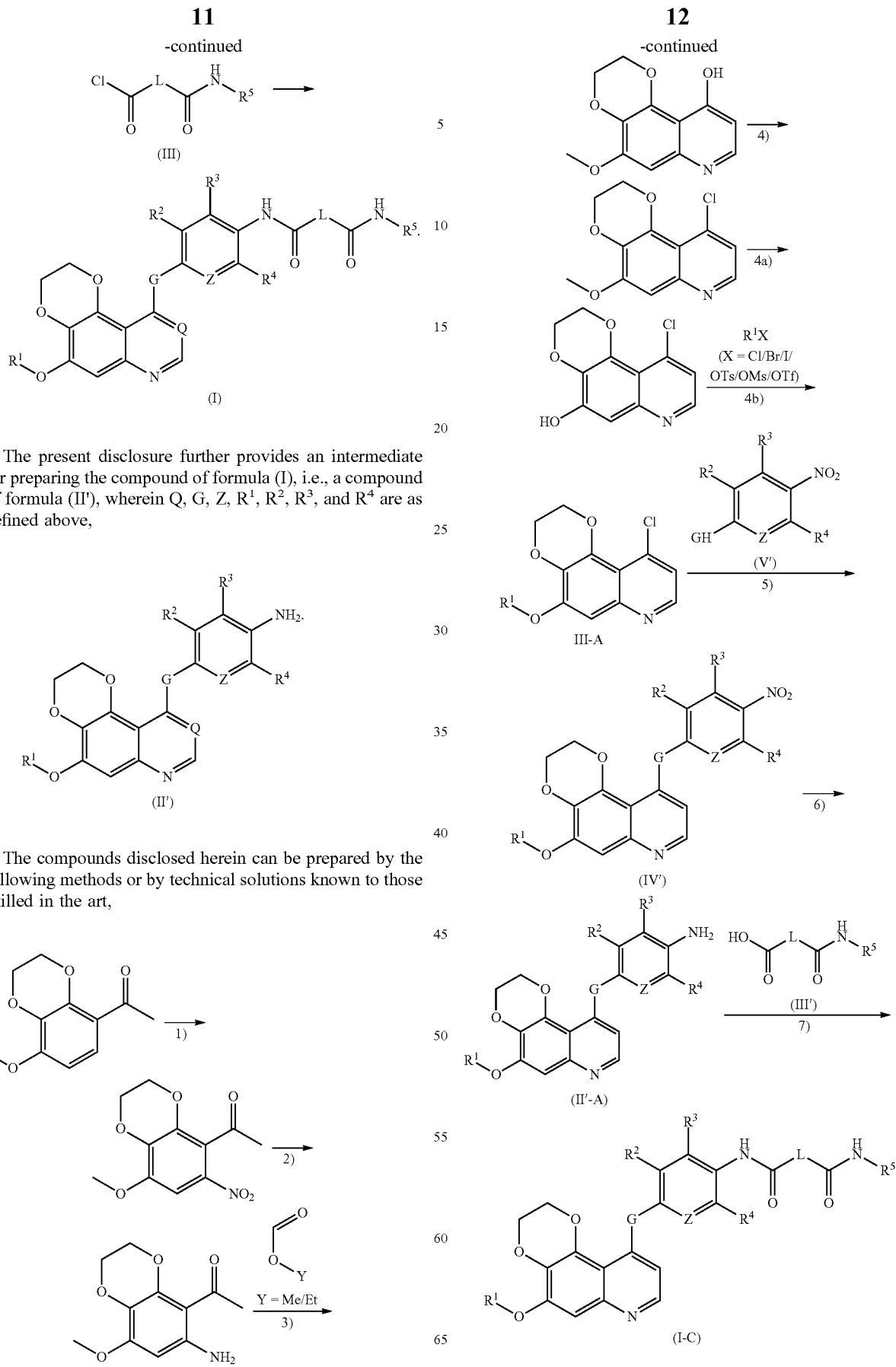
The present disclosure further provides an intermediate for preparing the compound of formula (I), i.e., a compound of formula (II'), wherein Q, G, Z, $R^1$, $R^2$, $R^3$, and $R^4$ are as defined above,
The compounds disclosed herein can be prepared by the following methods or by technical solutions known to those skilled in the art, Step 1) A nitrification reaction is carried out, preferably, with nitric acid and acetic acid.

Step 2) A nitro-reduction reaction is carried out by routine operations known by those skilled in the art; preferably, the conditions of the nitro-reduction reaction include, but are not limited to, hydrogen and Raney nickel, hydrogen and palladium/carbon, an iron or zinc powder under an acidic condition, or stannous chloride.

Step 3) 1-(8-methoxy-6-amino-2,3-dihydrobenzo[b][1,4]dioxin-5-yl)ethan-1-one and methyl formate or ethyl formate are reacted in an organic solvent, and catalyzed by a base to afford 10-hydroxy-5-methoxy-2,3-dihydro-[1,4]dioxino[2,3-f]quinoline, wherein the organic solvent includes, but is not limited to, one or a combination of two or more of dioxane, tetrahydrofuran, t-butanol, ethanol, and methanol; the base includes, but is not limited to, sodium t-butoxide, potassium t-butoxide, sodium methoxide, and sodium ethoxide; and this reaction can also be carried out under heating with the temperature of from room temperature to reflux temperature.

Step 4) 10-hydroxy-5-methoxy-2,3-dihydro-[1,4]dioxino[2,3-f]quinoline is reacted with a chlorinating reagent in an organic solvent to afford 10-chloro-5-methoxy-2,3-dihydro-[1,4]dioxino[2,3-f]quinoline, wherein the chlorinating reagent is phosphorus oxychloride; the organic solvent includes, but is not limited to, one or a combination of two or more of benzene, toluene, chlorobenzene and xylene; and the reaction can also be carried out in the presence of an organic base, e.g., triethylamine or diisopropylethylamine.

Step 4a) 10-chloro-5-methoxy-2,3-dihydro-[1,4]dioxino[2,3-f]quinoline is dissolved in an organic solvent and subjected to the action of Lewis acid to afford 5-hydroxy-10-chloro-2,3-dihydro-[1,4]dioxino[2,3-f]quinoline,
wherein the Lewis acid is boron tribromide or boron trichloride; and the organic solvent is dichloromethane.

Step 4b) 5-hydroxy-10-chloro-2,3-dihydro-[1,4]dioxino[2,3-f]quinoline is reacted with the compound of $R^1X$ in an organic solvent to afford the compound of formula III-A, wherein $R^1$ is as defined above; the organic solvent includes, but is not limited to, one or a combination of two or more of tetrahydrofuran, dioxane, DMF, DMA, DMSO, and acetonitrile; X in $R^1X$ is chlorine, bromine, iodine, mesylate, p-toluenesulfonate or triflate.

Step 5) The compound of formula III-A was dissolved in an organic solvent, mixed with the compound of formula V', and heated to 100° C. to 140° C. to afford the compound of IV'; wherein the organic solvent is selected from the group consisting of one or a combination of two or more of toluene, chlorobenzene, xylene, DMF, DMA and DMSO.

Step 6) A nitro-reduction reaction is carried out by routine operations known by those skilled in the art;
preferably, the conditions of the nitro-reduction reaction include, but are not limited to, hydrogen and Raney nickel, hydrogen and palladium/carbon, an iron or zinc powder under an acidic condition, or stannous chloride.

Step 7) In an alternative embodiment, when the compound of formula (III') is reacted with the compound of formula (II'-A), the compound of formula (III') can be first reacted with an acylating reagent, and then reacted with the compound of formula (II'-A).

Preferably, the acylating reagent includes, but is not limited to, one or a combination of two or more of phosphorus oxychloride, thionyl chloride, oxalyl chloride, phosphorus trichloride, or phosphorus pentachloride.

In another embodiment, the compound of formula (III') is reacted with the compound of formula (II'-A) in the presence of a condensing agent to afford the compound of formula (I-C),
preferably, the condensing agent includes, but is not limited to, one or a combination of two or more of carbodiimide-based condensing agent, onium salt-based condensing agent, organic phosphorus-based condensing agent and other types of condensing agents, preferably N,N'-dicyclohexylcarbodiimide (DCC), N,N'-diisopropylcarbodiimide (DIC), 1-hydroxybenzotriazole (HOBt), N,N-diisopropylethylamine (DIEA), 1-hydroxy-7-azabenzotriazole (HOAt), 0-(benzotriazol-1-yl)-N,N,N',N'-tetramethyluronium tetrafluoroborate (TBTU), (benzotriazol-1-yloxy)tris(dimethylamino)phosphonium hexafluorophosphate (BOP), O-(benzotriazol-1-yl)-N,N,N',N'-tetramethyluronium hexafluorophosphate (HBTU), O-(6-chlorobenzotriazol-1-yl)1,1,3,3-tetramethyluronium hexafluorophosphate (HCTU), O-(7-azabenzotriazol-1-yl)-N,N,N',N'-tetramethyluronium hexafluorophosphate (HATU), propylphosphonic anhydride (T3P), 1-(3-dimethylaminopropyl)-3-ethylcarbodiimide hydrochloride (EDCI), 1-ethyl-3-(3-dimethylaminopropyl)carbodiimide hydrochloride (EDC), (benzotriazol-1-yloxy)tripyrrolidinophosphonium hexafluorophosphate (PyBOP), and (3H-1,2,3-triazolo[4,5-b]pyridin-3-yloxy) tripyrrolidinophosphonium hexafluorophosphate (PyAOP);
preferably, this step can be carried out in an organic base, which includes, but is not limited to, one or a combination of two or more of triethylamine, diisopropylethylamine, pyridine, 4-dimethylaminopyridine, 2,6-lutidine, 1,8-diazabicycloundec-7-ene or N-methylmorpholine.

When $R^1$ is $-CH_3$, steps 4a and 4b can be omitted. That is to say, after completing step 4), the operation of step 5) is carried out.

Meanwhile, for example, the order of steps 4a and 4b and step 5 may not be fixed. For example, step 5 may be first carried out, followed by steps 4a and 4b.

It is apparent that the compounds of Formula I, the isomers, crystalline forms or prodrugs, and pharmaceutically acceptable salts thereof, may exist in both solvated and unsolvated forms. For example, the solvated form can be a hydrate form. The disclosure includes both solvated and unsolvated forms.

The compounds of the present disclosure may have asymmetric carbon atoms. Such diastereomeric mixtures can be separated into their individual diastereomers on the basis of their different physicochemical properties by methods known to those skilled in the art, for example, by chromatography or fractional crystallization. Enantiomers can be separated by converting the enantiomeric mixtures into a diastereomeric mixture by reaction with an appropriate optically active compound, separating the diastereomers and converting (e.g., hydrolyzing) the individual diastereomers to the corresponding pure enantiomers. All such isomers, including diastereomer mixtures and pure enantiomers are considered as part of the disclosure.

The compound of the present disclosure as an active ingredient, and the method of preparing the same, are both included in the present disclosure. Moreover, the crystalline form of some of the compounds may exist as polymorphs, and such forms may also be included in the present disclosure. Additionally, some of the compounds may form solvates with water (i.e., hydrates) or common organic solvents, and such solvates are also included within the scope of the disclosure.

The compounds of the disclosure may be used in the free form for treatment or, when appropriate, in the form of a pharmaceutically acceptable salt or other derivative for treatment. As used herein, the term "pharmaceutically acceptable salt" refers to organic and inorganic salts of the compounds of the present disclosure which are suitable for use in human and lower animals without undue toxicity, irritation, allergic response, etc., and have reasonable benefit/risk ratio. Pharmaceutically acceptable salts of amines, carboxylic acids, phosphonates, and other types of compounds are well known in the art. The salt can be formed by reacting a compound of the disclosure with a suitable free base or acid, including, but not limited to, salts with inorganic acids such as hydrochloric acid, hydrobromic acid, phosphoric acid, sulfuric acid, perchloric acid or with organic acids such as acetic acid, oxalic acid, maleic acid, tartaric acid, citric acid, succinic acid, malonic acid. Or the salts may be obtained by methods well known in the art, such as ion exchange. Other pharmaceutically acceptable salts include adipate, alginate, ascorbate, aspartate, besylate, benzoate, bisulfate, borate, butyrate, camphorate, camphorsulfonate, citrate, digluconate, lauryl sulfate, ethanesulfonate, formate, fumarate, glucoheptonate, glycerol phosphate, glyconate, hemisulfate, hexanoate, hydroiodide, 2-hydroxyethanesulfonate, lactobionate, lactate, laurate, lauryl sulfate, malate, maleate, mesylate, 2-naphthalenesulfonate, nicotinate, nitrate, oleate, palmitate, pamoate, pectate, persulphate, per-3-phenylpropionate, phosphate, picrate, propionate, stearate, sulfate, thiocyanate, p-toluenesulfonate, undecanoate, and the like. Representative alkali or alkaline earth metal salts include salts of sodium, lithium, potassium, calcium, magnesium, and the like. Other pharmaceutically acceptable salts include suitable non-toxic salts of ammonium, quaternary ammonium, and amine cations formed from halides, hydroxides, carboxylates, sulfates, phosphates, nitrates, lower alkyl sulfonates and aryl sulfonates.

Further, the term "prodrug" as used herein means that a compound can be converted into a compound of Formula (I) of the present disclosure in vivo. Such transformation is affected by hydrolysis of the prodrug in the blood or enzymatic conversion to the parent compound in the blood or tissue.

Pharmaceutical compositions of this disclosure comprise a compound of the formula (I) described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyper proliferation compound; and any pharmaceutically acceptable carrier, adjuvant or vehicle.

The compounds of the present disclosure may be used alone or in combination with one or more of other compounds of the present disclosure or with one or more of other agents. When administered in combination, the therapeutic agents can be formulated for simultaneous or sequential administration at different times, or the therapeutic agents can be administered as a single composition. By "combination therapy", it refers to the use of a compound of the disclosure in combination with another agent in the form of co-administration of each agent or sequential administration of each agent, in either case, for the purpose of achieving the optimal results. Co-administration includes dosage form for simultaneous delivery, as well as separate dosage forms for each compound. Thus, administration of the compounds of the disclosure can be combined with other therapies known in the art, for example, radiation therapy or cytostatic agents, cytotoxic agents, other anticancer agents, and the like as used in the treatment of cancer, in order to improve the symptoms of cancer. The administration sequence is not limited in the present disclosure. The compounds of the present disclosure may be administered before, simultaneously, or after other anticancer or cytotoxic agents.

To prepare the pharmaceutical ingredient of the present disclosure, one or more compounds of Formula (I) or salts thereof as an active ingredient can be intimately mixed with a pharmaceutical carrier, which is carried out according to a conventional pharmaceutical Formulation technique. The carrier can be used in a wide variety of forms depending on the form of preparation which is designed for different administration modes (for example, oral or parenteral administration). Suitable pharmaceutically acceptable carriers are well known in the art. A description of some of these pharmaceutically acceptable carriers can be found in the Handbook of Pharmaceutical Excipients, published jointly by the American Pharmaceutical Association and the Pharmaceutical Society of Great Britain.

The pharmaceutical composition of the present disclosure may have the following forms, for example, those suitable for oral administration, such as tablets, capsules, pills, powders, sustained release forms, solutions or suspensions; those for parenteral injections such as clear solutions, suspensions, emulsion; or those for topical use such as ointments, creams; or as a suppository for rectal administration. The pharmaceutical ingredients may also be presented in unit dosage form for single administration in a precise dosage. The pharmaceutical ingredient will include a conventional pharmaceutical carrier or excipient and a compound as an active ingredient prepared according to the present disclosure, and may also include other medical or pharmaceutical preparations, carriers, adjuvants, and the like.

Therapeutic compounds can also be administered to mammals other than humans. The drug dosage for a mammal will depend on the species of the animal and its disease condition or its disordered condition. The therapeutic compound can be administered to the animal in the form of a capsule, a bolus, or a tablet or liquid. The therapeutic compound can also be introduced into the animal by injection or infusion. These drug forms are prepared in a traditional manner complying with standard veterinary practice. As an alternative, the therapeutic compounds can be mixed with the animal feed and fed to the animal, so that the concentrated feed additive or premix can be prepared by mixing ordinary animal feed.

It is a further object of the present disclosure to provide a method for treating cancer in a subject in need thereof, including a method for administering to the subject a therapeutically effective amount of a composition containing the compound of the present disclosure.

The present disclosure also includes the use of a compound of the present disclosure, or a pharmaceutically acceptable derivative thereof, in the manufacture of a medicament for treating cancer (including non-solid tumors, solid tumors, primary or metastatic cancer, as indicated elsewhere herein and including one or more of other therapies to which the cancer is resistant or refractory), as well as other diseases (including, but not limited to, ocular fundus diseases, psoriasis, atheroma, pulmonary fibrosis, liver fibrosis, myelofibrosis, and the like). The cancer includes, but is not limited to any one of non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myeloid leukemia, non-Hodgkin's lymphoma, nasopharyngeal carcinoma, esophageal cancer, brain tumor, B-cell and T-cell lymphoma, lymphoma, multiple myeloma, biliary cancer and sarcoma, and cholangiocarcinoma.

In order to make the objectives, technical solutions and advantages of the present disclosure more clear, the present disclosure will be further described in detail below in conjunction with specific examples. It should be understood that the specific examples described here are only used to explain the present disclosure and are not intended to limit the present invention. If no specific technology or conditions are indicated in examples, the technology or conditions described in the literature in the art or the product specification shall be followed. If reagents or instruments used do not indicate manufacturers, they are all conventional products that are commercially available. The term "and/or" as used herein includes any and all combinations of one or more related listed items. The examples provided below can better illustrate the present disclosure. Unless otherwise specified, all temperatures are in degrees Celsius.

Intermediate: Preparation of 10-chloro-5-methoxy-2,3-dihydro-[1,4]dioxino[2,3-f]quinoline

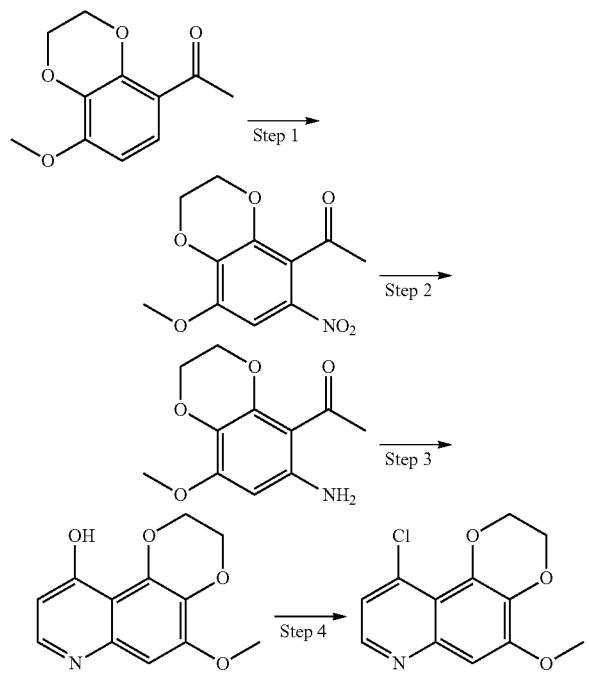

Step 1) Preparation of 1-(8-methoxy-6-nitro-2,3-dihydrobenzo[b][1,4]dioxin-5-yl)ethan-1-one 1-(8-methoxy-2,3-dihydrobenzo[b][1,4]dioxin-5-yl)ethan-1-one (20.8 g, 100 mmol), nitric acid (22 mL) and acetic acid (44 mL) were placed in a round-bottom flask and stirred until the reaction was completed. The reaction solution was poured into crushed ice, and filtered with suction to afford 16.5 g of a yellow solid product with a yield of 66%. $^1$HNMR (400 MHz, Chloroform-d) δ 7.37 (s, 1H), 4.43 (dd, J=5.4, 2.7 Hz, 2H), 4.35 (dd, J=5.3, 2.7 Hz, 2H), 3.98 (s, 3H), 2.57 (s, 3H); MS: 254[M+H]$^+$.

Step 2) Preparation of 1-(8-methoxy-6-amino-2,3-dihydrobenzo[b][1,4]dioxin-5-yl)ethan-1-one 1-(8-methoxy-6-nitro-2,3-dihydrobenzo[b][1,4]dioxin-5-yl)ethan-1-one (16.5 g, 65 mmol) was placed in a reaction flask, to which palladium/carbon (2 g) was then added. The mixture was stirred under hydrogen atmosphere until the reaction was completed. The reaction solution was filtered with suction and concentrated to afford 13.7 g of an off-white solid product with a yield of 95%. $^1$HNMR (400 MHz, DMSO-d6) δ 6.90 (s, 2H), 5.96 (s, 1H), 4.32-4.25 (m, 2H), 4.18-4.09 (m, 2H), 3.72 (s, 3H), 2.41 (s, 3H); MS: 224[M+H]$^+$.

Step 3) Preparation of 10-hydroxy-5-methoxy-2,3-dihydro-[1,4]dioxino[2,3-f]quinoline 1-(6-amino-8-methoxy-2,3-dihydrobenzo[b][1,4]dioxin-5-yl)ethan-1-one (13.7 g, 62 mmol) and ethyl formate (27.5 g, 372 mmol) were dissolved in dioxane, to which sodium tert-butoxide (17.8 g, 186 mmol) was then added. The mixture was stirred until the raw materials disappeared. 10 ml of methanol was added to the reaction solution, which was then stirred until the reaction was completed. The reaction solution was neutralized with hydrochloric acid to neutrality. The mixture was then filtered with suction and concentrated to afford 14.4 g of an off-white solid product with a yield of 99%. $^1$HNMR (400 MHz, DMSO-d6) δ 11.26 (s, 1H), 7.59 (d, J=7.3 Hz, 1H), 6.55 (s, 1H), 5.77 (d, J=7.2 Hz, 1H), 4.34-4.13 (m, 4H), 3.82 (s, 3H); MS: 234[M+H]$^+$.

Step 4) Preparation of 10-chloro-5-methoxy-2,3-dihydro-[1,4]dioxino[2,3-f]quinoline 10-hydroxy-5-methoxy-2,3-dihydro-[1,4]dioxino[2,3-f]quinoline (14.4 g, 61 mmol) was placed in a reaction flask, and dissolved by adding toluene. To the mixture were added triethylamine (42 mL, 305 mmol) and phosphorus oxychloride (17 mL, 183 mmol). The reaction solution was heated and stirred until the reaction was completed. The reaction solution was distilled to remove the solvent. The resulting solid was washed with an aqueous solution of sodium bicarbonate and then filtered with suction to afford 14.1 g of an off-white solid with a yield of 92%. $^1$HNMR (400 MHz, DMSO-d$_6$) δ 8.51 (d, J=4.9 Hz, 1H), 7.38 (d, J=4.8 Hz, 1H), 7.12 (s, 1H), 4.49-4.29 (m, 4H), 3.93 (s, 3H); MS: 252[M+H]$^+$.

Intermediate: Preparation of 1-((4-fluorophenyl)carbamoyl)cyclopropan-1-carboxylic acid

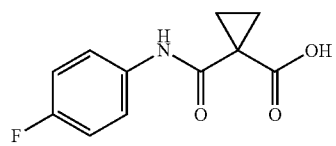 [SMILES: O=C(O)C1(C(=O)Nc2ccc(F)cc2)CC1]

1,1-Cyclopropyldicarboxylic acid (1.04 g) was added to anhydrous tetrahydrofuran (20 mL). To the stirred suspension was slowly added dropwise triethylamine (0.84 g) in ice water bath, and stirred for half an hour. Thionyl chloride (1.1 g) was then added dropwise at 0° C. After the addition, the mixture was further stirred for 1 hour. Triethylamine (0.8 g) and a solution of 4-fluoroaniline (0.9 g) in tetrahydrofuran (10 mL) were then added. After further stirring for 2 hours, the reaction was completed. The reaction solution was concentrated, dissolved in 1 N sodium hydroxide, and extracted with ethyl acetate. The aqueous phase was adjusted to pH 2.0 with a 1N solution of dilute hydrochloric acid, and further stirred for half an hour. The mixture was filtered to afford 1.1 g of a white solid product with a yield of 62%. MS: 224[M+H]$^+$.

Intermediate: Preparation of 1-((4-fluorophenyl)carbamoyl)cyclopropan-1-carbonyl chloride

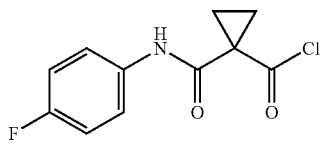 [SMILES: O=C(Cl)C1(C(=O)Nc2ccc(F)cc2)CC1]

A solution of 1-((4-fluorophenyl)carbamoyl)cyclopropan-1-carboxylic acid (111 mg, 0.5 mmol) in thionyl chloride (2 mL) was heated to reflux and stirred for reaction. After the reaction solution became clear, reflux was continued for 1 hour. The reaction solution was cooled and concentrated to afford 120 mg of a light yellow solid product with a yield of 100%.

Example 1. Preparation of N-(4-fluorophenyl)-N-(4-((5-methoxy-2,3-dihydro-[1,4]dioxino[2,3-f]quinolin-10-yl)oxy)phenyl)cyclopropan-1,1-dicarboxamide

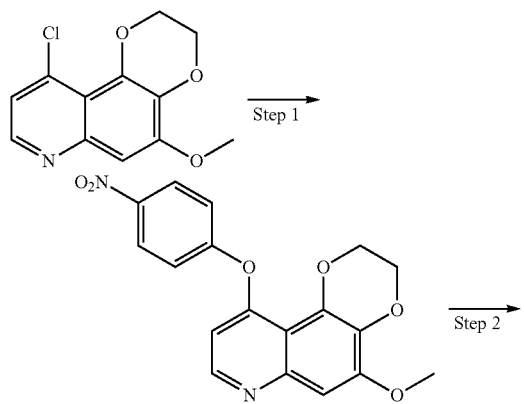

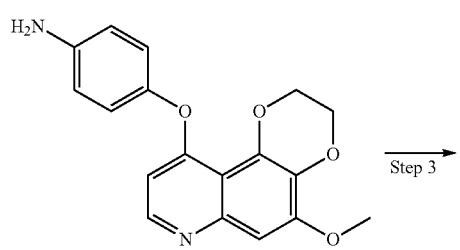

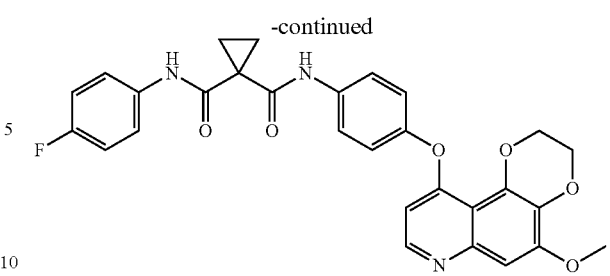

Step 1): 10-chloro-5-methoxy-2,3-dihydro-[1,4]dioxino[2,3-f]quinoline (251 mg, 1 mmol) and p-nitrophenol (139 mg, 1 mmol) were placed in a reaction flask, to which chlorobenzene was then added. The mixture was heated to reflux and stirred until the reaction was completed. After cooling, the reaction solution was filtered with suction. The resulting solid was washed with an aqueous solution of potassium carbonate to afford 250 mg of a pale yellow solid (5-methoxy-10-(4-nitrophenoxy)-2,3-dihydro-[1,4]dioxino[2,3-f]quinoline) with a yield of 71%. MS: 355[M+H]$^+$.

Step 2): The product (250 mg, 0.7 mmol) obtained in step 1) was placed in a reaction flask, to which methanol and Raney nickel (250 mg) were then added. The reaction solution was stirred under hydrogen atmosphere until the reaction was completed. The reaction solution was filtered with suction and concentrated to afford 226 mg of an off-white solid product (4-((5-methoxy-2,3-dihydro-[1,4]dioxino[2,3-f]quinolin-10-yl)oxy)aniline) with a yield of 99%. MS: 325[M+H]$^+$.

Step 3): The product (226 mg, 0.7 mmol) obtained in step 2) and 1-((4-fluorophenyl)carbamoyl)cyclopropan-1-carboxylic acid were placed in a reaction flask, and dissolved by adding N,N-dimethylformamide. To the mixture were added O-(7-azabenzotriazol-1-yl)-N,N,N',N'-tetramethyluronium hexafluorophosphate (HATU) (380 mg, 1 mmol) and diethylisopropylamine (0.25 mL, 1.5 mmol), and stirred until the reaction was completed. The reaction solution was washed with an aqueous solution of sodium carbonate, filtered with suction, and subjected to column chromatography to afford 296 mg of a white solid with a yield of 80%. $^1$HNMR (300 MHz, DMSO-d$_6$) δ 10.19-10.02 (m, 2H), 8.43 (d, J=5.2 Hz, 1H), 7.78-7.67 (m, 2H), 7.67-7.56 (m, 2H), 7.22-7.01 (m, 5H), 6.42 (d, J=5.3 Hz, 1H), 4.38-4.25 (m, 4H), 3.92 (s, 3H), 1.50-1.40 (m, 4H). MS: 530[M+H]$^+$.

Example 2. Preparation of N-(3-fluoro-4-((5-methoxy-2,3-dihydro-[1,4]dioxino[2,3-f]quinolin-10-yl)oxy)phenyl)-N-(4-fluorophenyl)cyclopropan-1,1-dicarboxamide

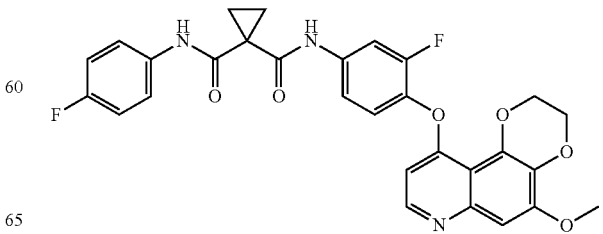

Step 1) Preparation of 10-(2-fluoro-4-nitrophenoxy)-5-methoxy-2,3-dihydro-[1,4]dioxino[2,3-f]quinoline Referring to step 1) of Example 1, except that an equimolar equivalent of 2-fluoro-4-nitrophenol was used in place of p-nitrophenol. $^1$HNMR (400 MHz, DMSO-$d_6$) δ 8.67 (d, J=5.0 Hz, 1H), 8.44-8.27 (m, 1H), 8.13-7.93 (m, 1H), 7.19 (s, 1H), 7.07 (d, J=4.9 Hz, 1H), 6.98 (t, J=8.7 Hz, 1H), 4.31-4.18 (m, 2H), 4.16-4.06 (m, 2H), 3.95 (s, 3H); MS: 373[M+H]$^+$.

Step 2) Preparation of 3-fluoro-4-((5-methoxy-2,3-dihydro-[1,4]dioxino[2,3-f]quinolin-10-yl)oxy)aniline Referring to step 2) of Example 1, except that an equimolar equivalent of 10-(2-fluoro-4-nitrophenoxy)-5-methoxy-2,3-dihydro-[1,4]dioxino[2,3-f]quinoline was used in place of 5-methoxy-10-(4-nitrophenoxy)-2,3-dihydro-[1,4]dioxino[2,3-f]quinoline. $^1$HNMR (400 Hz, DMSO-d6) δ 8.38 (d, J=5.2 Hz, 1H), 7.05 (s, 1H), 6.99 (t, J=9.0 Hz, 1H), 6.61-6.49 (m, 1H), 6.49-6.38 (m, 1H), 6.33 (d, J=5.3 Hz, 1H), 5.53-5.37 (m, 2H), 4.36-4.38 (m, 4H), 3.92 (s, 3H); MS: 343[M+H]$^+$.

Step 3) Preparation of N-(3-fluoro-4-((5-methoxy-2,3-dihydro-[1,4]dioxino[2,3-f]quinolin-10-yl)oxy)phenyl)-N-(4-fluorophenyl)cyclopropan-1,1-dicarboxamide Referring to step 3) of Example 1, except that an equimolar equivalent of 3-fluoro-4-((5-methoxy-2,3-dihydro-[1,4]dioxino[2,3-f]quinolin-10-yl)oxy)aniline was used in place of 4-((5-methoxy-2,3-dihydro-[1,4]dioxino[2,3-f]quinolin-10-yl)oxy)aniline. $^1$HNMR (400 MHz, DMSO-$d_6$) δ 10.30 (s, 1H), 9.97 (s, 1H), 8.35 (d, J=5.2 Hz, 1H), 7.94-7.69 (m, 1H), 7.64-7.52 (m, 2H), 7.48-7.32 (m, 1H), 7.19 (t, J=9.0 Hz, 1H), 7.09 (t, J=8.8 Hz, 2H), 7.01 (s, 1H), 6.32 (d, J=5.2 Hz, 1H), 4.28 (s, 4H), 3.85 (s, 3H), 1.55-1.28 (m, 4H). MS: 548[M+H]$^+$.

Example 3. Preparation of N-(2-fluoro-4-((5-methoxy-2,3-dihydro-[1,4]dioxino[2,3-f]quinolin-10-yl)oxy)phenyl)-N-(4-fluorophenyl)cyclopropan-1,1-dicarboxamide

Step 1) Preparation of 10-(3-fluoro-4-nitrophenoxy)-5-methoxy-2,3-dihydro-[1,4]dioxino[2,3-f]quinoline Referring to step 1) of Example 1, except that an equimolar equivalent of 3-fluoro-4-nitrophenol was used in place of p-nitrophenol. MS: 373[M+H]$^+$.

Step 2) Preparation of 2-fluoro-4-((5-methoxy-2,3-dihydro-[1,4]dioxino[2,3-f]quinolin-10-yl)oxy)aniline Referring to step 2) of Example 1, except that an equimolar equivalent of 10-(3-fluoro-4-nitrophenoxy)-5-methoxy-2,3-dihydro-[1,4]dioxino[2,3-f]quinoline was used in place of 5-methoxy-10-(4-nitrophenoxy)-2,3-dihydro-[1,4]dioxino[2,3-f]quinoline. $^1$HNMR (400 MHz, DMSO-d6) δ 8.38 (d, J=5.2 Hz, 1H), 7.04 (s, 1H), 6.98-6.91 (m, 1H), 6.89-6.79 (m, 1H), 6.78-6.67 (m, 1H), 6.37 (d, J=5.2 Hz, 1H), 5.14 (s, 2H), 4.43-4.30 (m, 4H), 3.91 (s, 3H); MS: 343[M+H]$^+$.

Step 3) Preparation of N-(2-fluoro-4-((5-methoxy-2,3-dihydro-[1,4]dioxino[2,3-f]quinolin-10-yl)oxy)phenyl)-N-(4-fluorophenyl)cyclopropan-1,1-dicarboxamide

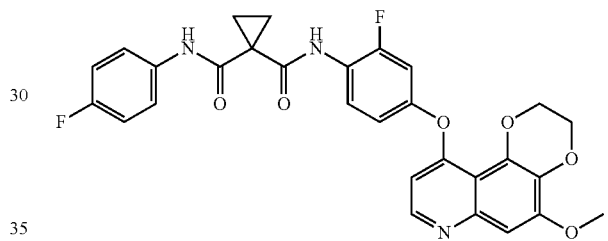

Referring to step 3) of Example 1, except that an equimolar equivalent of 2-fluoro-4-((5-methoxy-2,3-dihydro-[1,4]dioxino[2,3-f]quinolin-10-yl)oxy)aniline was used in place of 4-((5-methoxy-2,3-dihydro-[1,4]dioxino[2,3-f]quinolin-10-yl)oxy)aniline. $^1$HNMR (400 MHz, DMSO-$d_6$) δ 10.49 (s, 1H), 9.97 (s, 1H), 8.50 (d, J=5.1 Hz, 1H), 7.92-7.82 (m, 1H), 7.65-7.57 (m, 2H), 7.25-7.06 (m, 4H), 6.89-6.84 (m, 1H), 6.63 (d, J=5.1 Hz, 1H), 4.33-4.22 (m, 4H), 3.92 (s, 3H), 1.63-1.52 (m, 4H); MS: 548[M+H]$^+$.

Example 4. Preparation of N-(4-fluorophenyl)-N-(4-((5-(3-morpholinopropoxy)-2,3-dihydro-[1,4]dioxino[2,3-f]quinolin-10-yl)oxy)phenyl)cyclopropan-1,1-dicarboxamide

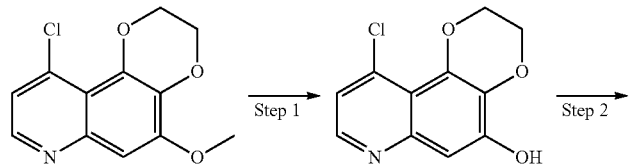

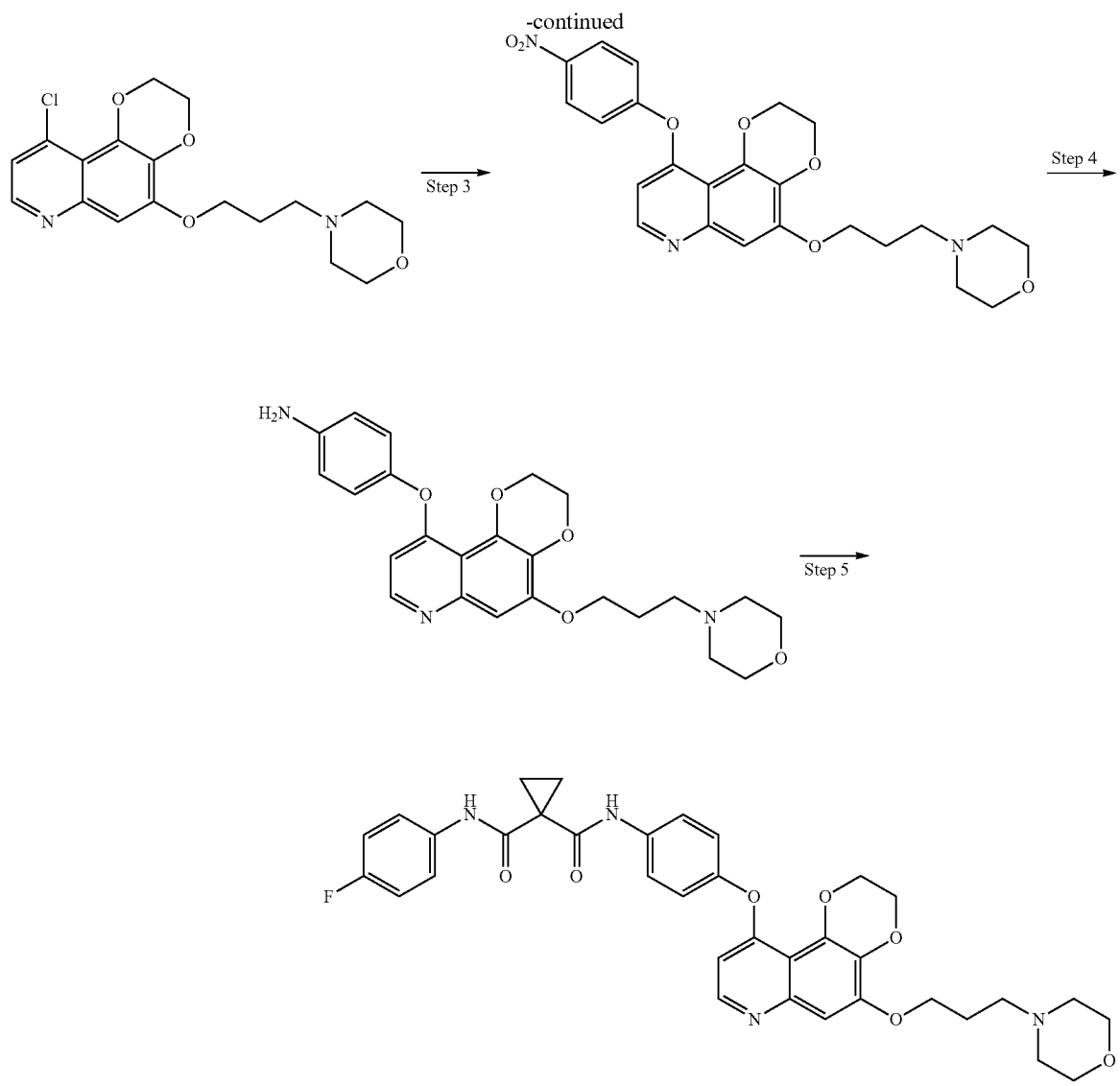

Step 1) 10-chloro-5-methoxy-2,3-dihydro-[1,4]dioxino[2,3-f]quinoline (251 mg, 1 mmol) was dissolved in dichloromethane, to which 1 mol per liter of boron tribromide in dichloromethane (3 mL, 3 mmol) was then added. The mixture was stirred until the reaction was completed. The reaction solution was concentrated to afford 236 mg of a light yellow solid product (5-hydroxy-10-chloro-2,3-dihydro-[1,4]dioxino[2,3-f]quinoline) with a yield of 99%. MS: 238[M+H]+.

Step 2) The product (236 mg, 1 mmol) obtained in step 1) was dissolved in N,N-dimethylformamide, to which 4-(3-chloropropyl)morpholine (163 mg, 1 mmol) and potassium carbonate (414 mg, 3 mmol) were then added. The mixture was heated and stirred until the reaction was completed. Water was added to the reaction solution, which was then extracted with ethyl acetate. The organic phase was concentrated and then subjected to column chromatography to afford 291 mg of an off-white solid (10-chloro-5-(3-morpholinopropoxy)-2,3-dihydro-[1,4]dioxino[2,3-f]quinoline) with a yield of 80%. $^1$H NMR (400 MHz, DMSO-$d_6$) δ 8.50 (d, J=4.8 Hz, 1H), 7.37 (d, J=4.8 Hz, 1H), 7.10 (s, 1H), 4.47-4.30 (m, 4H), 4.17 (t, J=6.4 Hz, 2H), 3.59 (t, J=4.6 Hz, 4H), 2.45 (t, J=7.1 Hz, 2H), 2.39 (d, J=4.5 Hz, 4H), 1.97-1.95 (m, 2H). MS: 365[M+H]+.

Step 3) Preparation of 5-(3-morpholinopropoxy)-10-(4-nitrophenoxy)-2,3-dihydro-[1,4]dioxino[2,3-f]quinoline Referring to step 1) of Example 1, except that an equimolar equivalent of 10-chloro-5-(3-morpholinopropoxy)-2,3-dihydro-[1,4]dioxino[2,3-f]quinoline was used in place of 10-chloro-5-methoxy-2,3-dihydro-[1,4]dioxino[2,3-f]quinoline. MS: 468[M+H]+.

Step 4) Preparation of 4-((5-(3-morpholino-propoxy)-2,3-dihydro-[1,4]dioxino[2,3-f]quinolin-10-yl)oxy)aniline Referring to step 2) of Example 1, except that an equimolar equivalent of 5-(3-morpholinopropoxy)-10-(4-nitrophenoxy)-2,3-dihydro-[1,4]dioxino[2,3-f]quinoline was used in place of 5-methoxy-10-(4-nitrophenoxy)-2,3-dihydro-[1,4]dioxino[2,3-f]quinoline. $^1$H NMR (400 MHz, DMSO-d6) δ 8.33 (d, J=5.3 Hz, 1H), 7.00 (s, 1H), 6.84 (d, J=8.1 Hz, 2H), 6.65 (d, J=8.2 Hz, 2H), 6.29 (d, J=5.3 Hz, 1H), 5.10 (s, 2H), 4.35 (s, 4H), 4.20-4.11 (m, 2H), 3.62-3.56 (m, 4H), 2.48-2.36 (m, 6H), 2.00-1.91 (m, 2H). MS: 438[M+H]$^+$.

Step 5) Preparation of N-(4-fluorophenyl)-N-(4-((5-(3-morpholinopropoxy)-2,3-dihydro-[1,4]dioxino[2,3-f]quinolin-10-yl)oxy)phenyl)cyclopropan-1,1-dicarboxamide Referring to step 3) of Example 1, except that an equimolar equivalent of 4-((5-(3-morpholinopropoxy)-2,3-dihydro-[1,4]dioxino[2,3-f]quinolin-10-yl)oxy)aniline was used in place of 4-((5-methoxy-2,3-dihydro-[1,4]dioxino[2,3-f]quinolin-10-yl)oxy)aniline. $^1$HNMR (400 MHz, DMSO-d$_6$) δ 10.14 (s, 1H), 10.07 (s, 1H), 8.41 (d, J=5.3 Hz, 1H), 7.70 (d, J=8.6 Hz, 2H), 7.63 (dd, J=9.1, 5.1 Hz, 2H), 7.18-7.12 (m, 2H), 7.11-7.03 (m, 3H), 6.41 (d, J=5.2 Hz, 1H), 4.37-4.26 (m, 4H), 4.26-4.10 (m, 2H), 3.68-3.54 (m, 4H), 2.44-2.39 (m, 4H), 2.02-1.92 (m, 2H), 1.52-1.41 (m, 6H); $^{13}$C NMR (101 MHz, DMSO-d6) δ 168.6, 168.5, 161.3, 151.7, 151.1, 149.6, 146.7, 138.2, 136.0, 135.6, 132.28, 122.9, 122.8, 122.6, 120.7, 115.6, 115.3, 108.7, 105.7, 102.2, 67.1, 66.7, 64.4, 63.9, 55.3, 53.8, 31.9, 26.2, 15.8; MS: 643[M+H]$^+$.

Example 5. Preparation of N-(3-fluoro-4-((5-(3-morpholinopropoxy)-2,3-dihydro-[1,4]dioxino[2,3-f]quinolin-10-yl)oxy)phenyl)-N-(4-fluorophenyl)cyclopropan-1,1-dicarboxamide Steps 1 and 2 are the same as Steps 1 and 2 of the preparation of Example 4.

Step 3) Preparation of 10-(2-fluoro-4-nitrophenoxy)-5-(3-morpholinopropoxy)-2,3-dihydro-[1,4]dioxino[2,3-f]quinoline

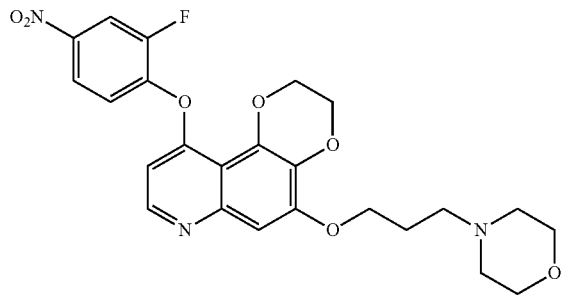 [SMILES: O=[N+]([O-])c1ccc(Oc2ccnc3cc(OCCCN4CCOCC4)c4c(c23)OCCO4)c(F)c1]

Referring to step 3) of Example 4, except that an equimolar equivalent of 2-fluoro-4-nitrophenol was used in place of p-nitrophenol. MS: 486[M+H]$^+$.

Step 4) Preparation of 3-fluoro-4-((5-(3-morpholinopropoxy)-2,3-dihydro-[1,4]dioxino[2,3-f]quinolin-10-yl)oxy)aniline

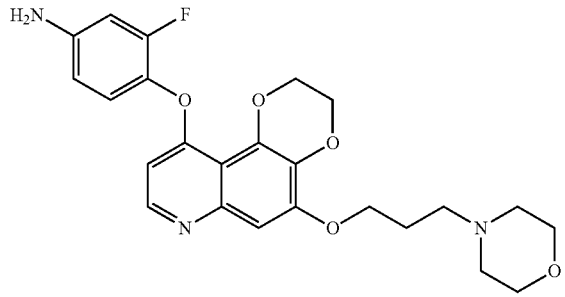

Referring to step 2) of Example 1, except that an equimolar equivalent of 10-(2-fluoro-4-nitrophenoxy)-5-(3-morpholinopropoxy)-2,3-dihydro-[1,4]dioxino[2,3-f]quinoline was used in place of 5-methoxy-10-(4-nitrophenoxy)-2,3-dihydro-[1,4]dioxino[2,3-f]quinoline. $^1$H NMR (400 MHz, DMSO-d$_6$) δ 8.37 (d, J=5.3 Hz, 1H), 7.08-6.88 (m, 2H), 6.60-6.49 (m, 1H), 6.48-6.40 (m, 1H), 6.32 (d, J=5.2 Hz, 1H), 5.44 (s, 2H), 4.37-4.39 (m, 4H), 4.16 (t, J=6.4 Hz, 2H), 3.59 (t, J=4.6 Hz, 4H), 2.46 (d, J=7.0 Hz, 2H), 2.39 (s, 4H), 1.95-1.97 (m, 2H); MS: 456[M+H]$^+$.

Step 5) Preparation of N-(3-fluoro-4-((5-(3-morpholinopropoxy)-2,3-dihydro-[1,4]dioxino[2,3-f]quinolin-10-yl)oxy)phenyl)-N-(4-fluorophenyl)cyclopropan-1,1-dicarboxamide

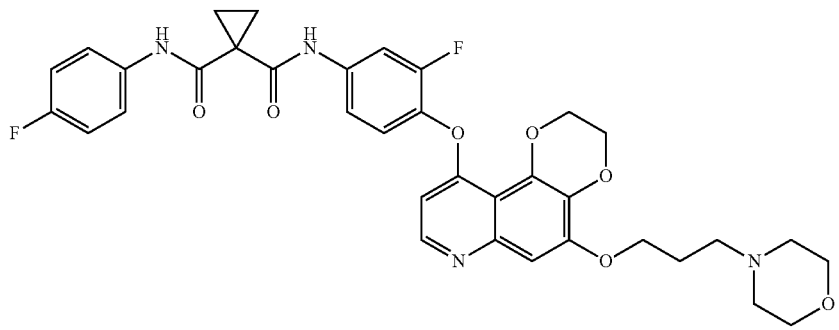 [SMILES: O=C(Nc1ccc(F)cc1)C1(C(=O)Nc2ccc(Oc3ccnc4cc(OCCCN5CCOCC5)c5c(c34)OCCO5)c(F)c2)CC1]

Referring to step 3) of Example 1, except that an equimolar equivalent of 3-fluoro-4-((5-(3-morpholinopropoxy)-2,3-dihydro-[1,4]dioxino[2,3-f]quinolin-10-yl)oxy)aniline was used in place of 4-((5-methoxy-2,3-dihydro-[1,4]dioxino[2,3-f]quinolin-10-yl)oxy)aniline. $^1$HNMR (400 MHz, DMSO-d6) δ 10.32 (s, 1H), 10.00 (s, 1H), 8.41 (d, J=5.2 Hz, 1H), 7.98-7.79 (m, 1H), 7.67-7.59 (m, 2H), 7.53-7.39 (m, 1H), 7.24 (t, J=9.0 Hz, 1H), 7.18-7.11 (m, 2H), 7.06 (s, 1H), 6.43-6.34 (m, 1H), 4.37-4.34 (m, 4H), 4.17 (t, J=6.4 Hz, 2H), 3.59 (t, J=4.6 Hz, 4H), 2.46 (t, J=7.1 Hz, 2H), 2.39 (d, J=4.6 Hz, 4H), 2.08-1.79 (m, 2H), 1.47 (d, J=2.3 Hz, 4H); 13C NMR (101 MHz, DMSO-d6) δ 168.7, 168.4, 160.9, 151.8, 149.6, 146.6, 138.2, 133.8, 129.8, 127.7, 123.4, 122.9, 115.6, 115.4, 107.9, 102.2, 67.1, 66.7, 64.4, 63.97, 55.2, 53.8, 32.3, 26.2, 15.7; MS: 661[M+H]$^+$.

Example 6. Preparation of N-(2-fluoro-4-((5-(3-morpholinopropoxy)-2,3-dihydro-[1,4]dioxino[2,3-f]quinolin-10-yl)oxy)phenyl)-N-(4-fluorophenyl)cyclopropan-1,1-dicarboxamide Steps 1 and 2 are the same as Steps 1 and 2 of the preparation of Example 4.

Step 3) Preparation of 10-(3-fluoro-4-nitrophenoxy)-5-(3-morpholinopropoxy)-2,3-dihydro-[1,4]dioxino[2,3-f]quinoline

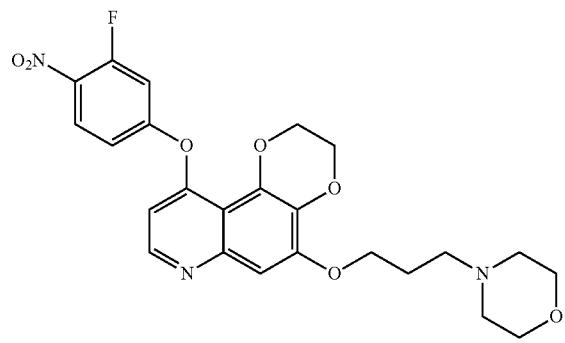 [SMILES: O=[N+]([O-])c1ccc(Oc2ccnc3cc(OCCCN4CCOCC4)c4c(c23)OCCO4)cc1F]

Referring to step 3) of Example 4, except that an equimolar equivalent of 3-fluoro-4-nitrophenol was used in place of p-nitrophenol. $^1$H NMR (400 MHz, DMSO-d$_6$) δ 8.69 (s, 1H), 8.29-8.09 (m, 1H), 7.51-7.35 (m, 1H), 7.22-7.08 (m, 2H), 6.97-6.72 (m, 1H), 4.33-4.16 (m, 4H), 4.12-3.98 (m, 2H), 3.65-3.54 (m, 4H), 2.47-2.26 (m, 6H), 2.05-1.82 (m, 2H). MS: 486[M+H]$^+$.

Step 4) Preparation of 2-fluoro-4-((5-(3-morpholinopropoxy)-2,3-dihydro-[1,4]dioxino[2,3-f]quinolin-10-yl)oxy)aniline

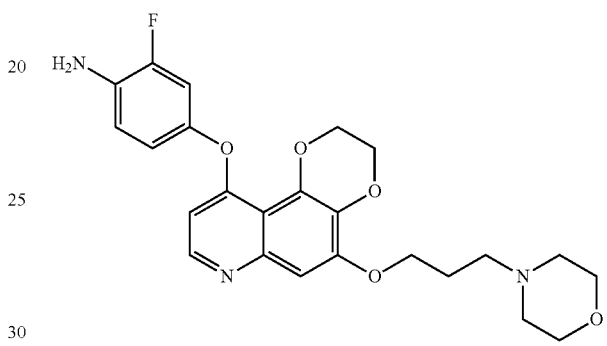

Referring to step 2) of Example 1, except that an equimolar equivalent of 10-(3-fluoro-4-nitrophenoxy)-5-(3-morpholinopropoxy)-2,3-dihydro-[1,4]dioxino[2,3-f]quinoline was used in place of 5-methoxy-10-(4-nitrophenoxy)-2,3-dihydro-[1,4]dioxino[2,3-f]quinoline. $^1$H NMR (400 MHz, DMSO-d6) δ 8.37 (d, J=5.2 Hz, 1H), 7.02 (s, 1H), 6.98-6.92 (m, 1H), 6.89-6.80 (m, 1H), 6.78-6.70 (m, 1H), 6.36 (d, J=5.2 Hz, 1H), 5.13 (s, 2H), 4.35 (s, 4H), 4.15 (t, J=6.5 Hz, 2H), 3.59 (t, J=4.6 Hz, 4H), 2.47 (t, J=7.2 Hz, 2H), 2.39 (d, J=4.9 Hz, 4H), 1.95-1.97 (m, 2H). MS: 456[M+H]$^+$.

Step 5) Preparation of N-(2-fluoro-4-((5-(3-morpholinopropoxy)-2,3-dihydro-[1,4]dioxino[2,3-f]quinolin-10-yl)oxy)phenyl)-N-(4-fluorophenyl)cyclopropan-1,1-dicarboxamide

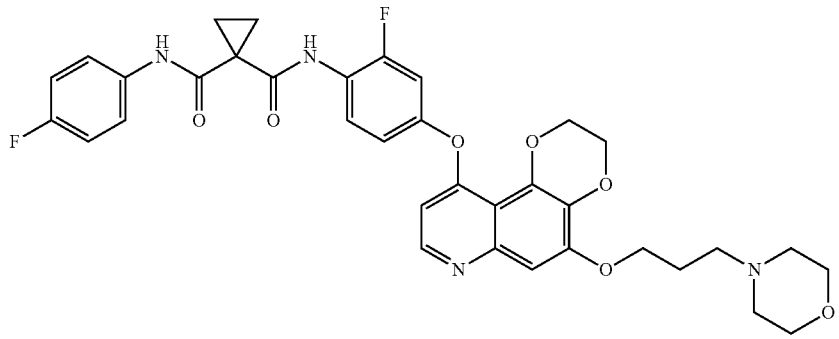 [SMILES: O=C(Nc1ccc(F)cc1)C1(C(=O)Nc2ccc(Oc3ccnc4cc(OCCCN5CCOCC5)c5c(c34)OCCO5)cc2F)CC1]

Referring to step 3) of Example 1, except that an equimolar equivalent of 2-fluoro-4-((5-(3-morpholinopropoxy)-2,3-dihydro-[1,4]dioxino[2,3-f]quinolin-10-yl)oxy)aniline was used in place of 4-((5-methoxy-2,3-dihydro-[1,4]dioxino[2,3-f]quinolin-10-yl)oxy)aniline. $^1$H NMR (400 MHz, DMSO-$d_6$) δ 10.48 (s, 1H), 9.97 (s, 1H), 8.50 (d, J=5.1 Hz, 1H), 7.86 (s, 1H), 7.71-7.48 (m, 2H), 7.16 (dd, J=9.9, 7.9 Hz, 2H), 7.10 (d, J=10.5 Hz, 2H), 6.95-6.80 (m, 1H), 6.63 (d, J=5.1 Hz, 1H), 4.34-4.28 (m, 2H), 4.27-4.24 (m, 2H), 4.17 (t, J=6.4 Hz, 2H), 3.59 (t, J=4.6 Hz, 4H), 2.46 (t, J=7.2 Hz, 2H), 2.38 (d, J=4.8 Hz, 4H), 1.95 (q, J=6.8 Hz, 2H), 1.56-1.58 (m, 4H). MS: 661[M+H]$^+$.

Example 7. N-(4-((5-ethoxy-2,3-dihydro-[1,4]dioxino[2,3-f]quinolin-10-yl)oxy)-3-fluorophenyl)-N-(4-fluorophenyl)cyclopropan-1,1-dicarboxamide

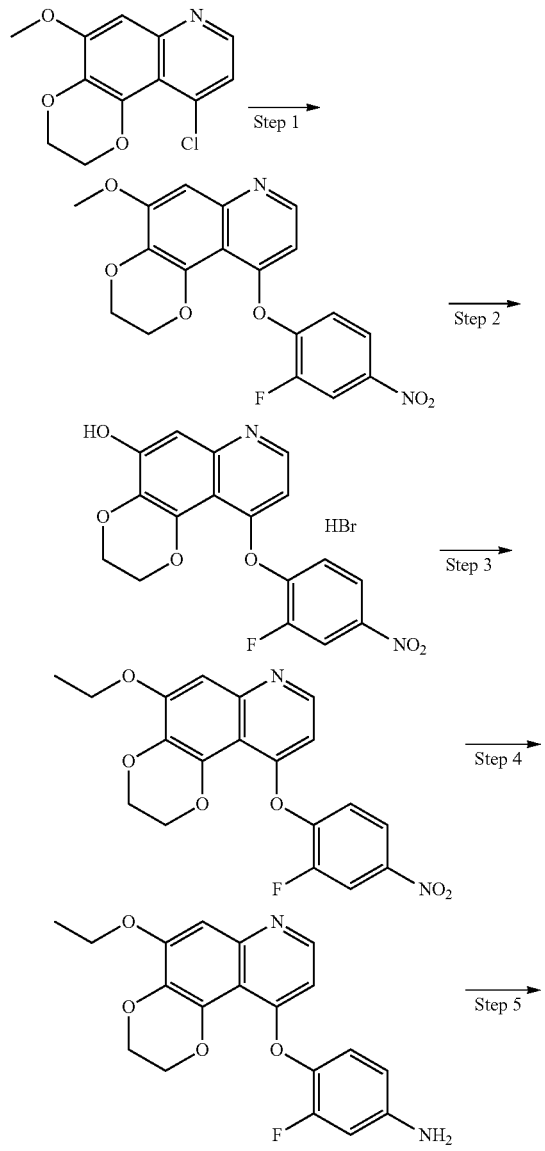

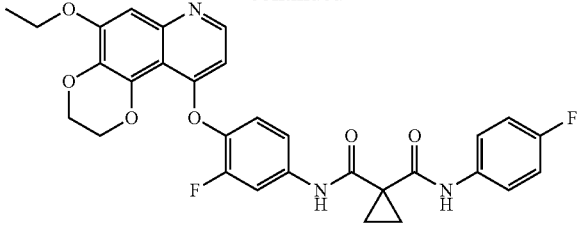

Step 1. A solution of 10-chloro-5-methoxy-2,3-dihydro-[1,4]dioxino[2,3-f]quinoline (2.5 g, 10 mmol), 2-fluoro-4-nitrophenol (1.6 g, 10 mmol) and potassium carbonate (2.1 g, 15 mmol) in DMF (20 mL) was heated to 80° C. for 3 hours. The reaction solution was cooled, slurried with water and filtered. The filter cake was dried to afford 3.5 g of an off-white solid product (10-(2-fluoro-4-nitrophenoxy)-5-methoxy-2,3-dihydro-[1,4]dioxino[2,3-f]quinoline) with a yield of 94%;

Step 2. The product (350 mg, 1 mmol) obtained in step 1 was added to a solution of bromide hydrogen in acetic acid (33%, 5 mL), and heated to 90° C. for 15 hours. The reaction solution was cooled, slurried with ethyl acetate (15 mL), and filtered. The filter cake was dried to afford 3.8 g of a light green solid (10-(2-fluoro-4-nitrophenoxy)-2,3-dihydro-[1,4]dioxino[2,3-f]quinolin-5-ol hydrobromide) with a yield of 87%. MS: 359[M+H]$^+$;

Step 3. To a solution of the product (440 mg, 1 mmol) obtained in step 2 in DMF (5 mL) were added bromoethane (165 mg, 1.5 mmol) and potassium carbonate (280 mg, 2 mmol), respectively, and heated to 80° C. for 10 hours. After cooling, water was added to the reaction solution, which was then extracted with ethyl acetate. The extract was washed with a saturated solution of sodium chloride, dried and concentrated. The residue was purified by column chromatography to afford 320 mg of a pale yellow solid product (10-(2-fluoro-4-nitrophenoxy)-5-ethoxy-2,3-dihydro-[1,4]dioxino[2,3-f]quinoline) with a yield of 83%;

Step 4. To a solution of the product (320 mg) obtained in step 3 in methanol (30 mL) was added Raney nickel, which was stirred at room temperature under hydrogen atmosphere for 3 hours. The reaction was filtered and washed. The filtrate was concentrated to afford 290 mg of a purple solid product (3-fluoro-4-((5-ethoxy-2,3-dihydro-[1,4]dioxino[2,3-f]quinolin-10-yl)oxy)aniline) with a yield of 81%. MS: 357[M+H]$^+$;

Step 5. To a solution of the product (36 mg, 0.1 mmol) obtained in step 4 in NMP (1 mL) were added a solution of 1-((4-fluorophenyl)carbamoyl)cyclopropan-1-carbonyl chloride (24 mg, 0.1 mmol) in dichloromethane (0.5 mL), and triethylamine (0.1 mL), and was stirred at room temperature for 5 hours. The reaction solution was quenched with water and filtered to afford a pale yellow solid, which was purified by preparative liquid chromatography to afford 24 mg of a white solid product with a yield of 43%. $^1$H NMR (600 MHz, DMSO-$d_6$) δ 10.33 (s, 1H), 10.00 (s, 1H), 8.41 (d, J=5.2 Hz, 1H), 7.86 (d, J=13.1 Hz, 1H), 7.63 (dd, J=8.7, 5.0 Hz, 2H), 7.45 (d, J=8.9 Hz, 1H), 7.25-7.13 (m, 3H), 7.05 (s, 1H), 6.39 (d, J=5.2 Hz, 1H), 4.34 (s, 4H), 4.25-4.10 (m, 2H), 1.47 (d, J=3.9 Hz, 4H), 1.41 (t, J=6.9 Hz, 3H). MS: 562[M+H]$^+$.

Example 8. N-(4-((5-(3-(dimethylamino)propoxy)-2,3-dihydro-[1,4]dioxino[2,3-f]quinolin-10-yl)oxy)-3-fluorophenyl)-N-(4-fluorophenyl)cyclopropan-1,1-dicarboxamide

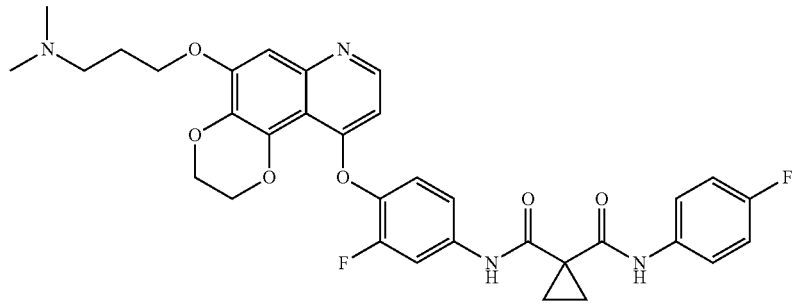 [SMILES: CN(C)CCCOc1cc2nccc(Oc3ccc(NC(=O)C4(C(=O)Nc5ccc(F)cc5)CC4)cc3F)c2c2c1OCCO2]

The preparation was carried out in a similar manner to Example 7, except that in step 3, an equimolar equivalent of dimethylaminopropyl chloride was used in place of bromoethane to afford a white solid product; $^1$H NMR (400 MHz, DMSO-d6) δ 10.32 (s, 1H), 9.99 (s, 1H), 8.41 (d, J=5.2 Hz, 1H), 7.85 (dd, J=13.2, 2.4 Hz, 1H), 7.68-7.56 (m, 2H), 7.45 (d, J=8.7 Hz, 1H), 7.23 (t, J=9.0 Hz, 1H), 7.15 (t, J=8.9 Hz, 2H), 7.05 (s, 1H), 6.40 (d, J=5.2 Hz, 1H), 4.35 (s, 4H), 4.16 (t, J=6.5 Hz, 2H), 2.42-2.32 (m, 2H), 2.20 (s, 6H), 1.94 (t, J=6.9 Hz, 2H), 1.47 (d, J=2.3 Hz, 4H). MS: 619 [M+H]$^+$.

Example 9. N-(4-((5-(3-(piperidin-1-yl)propoxy)-2,3-dihydro-[1,4]dioxino[2,3-f]quinolin-10-yl)oxy)-3-fluorophenyl)-N-(4-fluorophenyl)cyclopropan-1,1-dicarboxamide

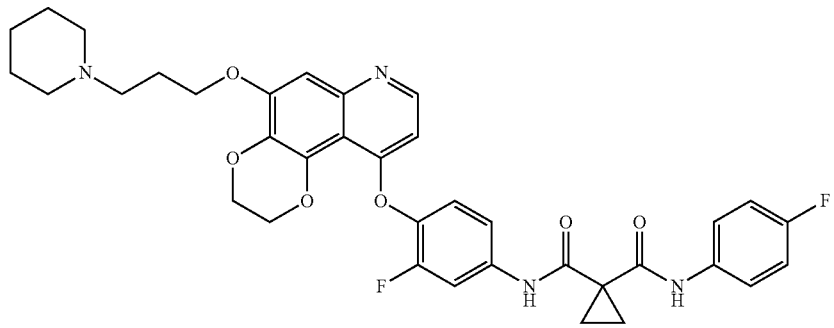 [SMILES: O=C(Nc1ccc(F)cc1)C1(C(=O)Nc2ccc(Oc3ccnc4cc(OCCCN5CCCCC5)c5c(c34)OCCO5)c(F)c2)CC1]

The preparation was carried out in a similar manner to Example 7, except that in step 3, an equimolar equivalent of (piperidin-1-yl)propyl chloride was used in place of bromoethane to afford a white solid product; $^1$H NMR (400 MHz, DMSO-d6) δ 10.31 (s, 1H), 9.99 (s, 1H), 8.41 (d, J=5.2 Hz, 1H), 7.85 (d, J=13.1 Hz, 1H), 7.69-7.59 (m, 2H), 7.45 (d, J=9.0 Hz, 1H), 7.23 (t, J=9.0 Hz, 1H), 7.20-7.10 (m, 2H), 7.05 (s, 1H), 6.40 (d, J=5.2 Hz, 1H), 4.35 (s, 4H), 4.16 (t, J=6.5 Hz, 2H), 2.41 (d, J=29.1 Hz, 6H), 1.95 (t, J=7.4 Hz, 2H), 1.62-1.44 (m, 8H), 1.39 (Br, 2H). MS: 659 [M+H]$^+$.

Example 10. N-(3-fluoro-4-((5-(2-methoxyethoxy)-2,3-dihydro-[1,4]dioxino[2,3-f]quinolin-10-yl)oxy)phenyl)-N-(4-fluorophenyl)cyclopropan-1,1-dicarboxamide

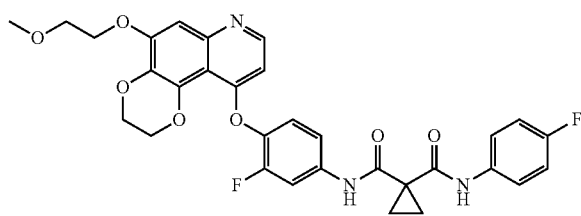 [SMILES: COCCOc1cc2nccc(Oc3ccc(NC(=O)C4(C(=O)Nc5ccc(F)cc5)CC4)cc3F)c2c2c1OCCO2]

The preparation was carried out in a similar manner to Example 7, except that in step 3, an equimolar equivalent of methoxyethyl bromide was used in place of bromoethane to afford a white solid product; $^1$H NMR (400 MHz, DMSO-d$_6$) δ 10.32 (s, 1H), 9.99 (s, 1H), 8.41 (d, J=5.2 Hz, 1H), 7.86 (dd, J=13.3, 2.5 Hz, 1H), 7.72-7.56 (m, 2H), 7.50-7.36 (m, 1H), 7.24 (t, J=9.0 Hz, 1H), 7.18-7.11 (m, 2H), 7.08 (s, 1H), 6.40 (dd, J=5.2, 1.0 Hz, 1H), 4.35 (s, 4H), 4.29-4.17 (m, 2H), 3.79-3.67 (m, 2H), 3.34 (s, 3H), 1.47 (d, J=2.0 Hz, 4H). MS: 592 [M+H]$^+$.

Example 11. N-(4-((5-(cyclopropylmethoxy)-2,3-dihydro-[1,4]dioxino[2,3-f]quinolin-10-yl)oxy)-3-fluorophenyl)-N-(4-fluorophenyl)cyclopropan-1,1-dicarboxamide

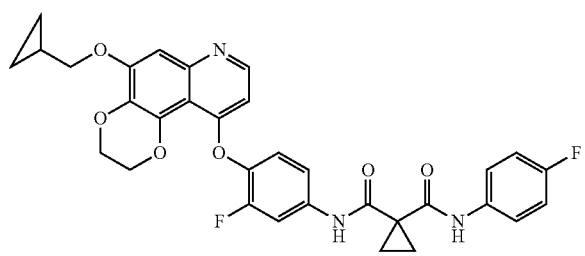 [SMILES: O=C(Nc1ccc(F)cc1)C1(C(=O)Nc2ccc(Oc3ccnc4cc(OCC5CC5)c5c(c34)OCCO5)c(F)c2)CC1]

The preparation was carried out in a similar manner to Example 7, except that in step 3, an equimolar equivalent of cyclopropylmethyl bromide was used in place of bromoethane to afford a white solid product; $^1$H NMR (400 MHz, DMSO-d$_6$) δ 10.31 (s, 1H), 9.99 (s, 1H), 8.40 (d, J=5.2 Hz, 1H), 7.85 (dd, J=13.3, 2.4 Hz, 1H), 7.63 (dd, J=9.1, 5.1 Hz, 2H), 7.45 (d, J=8.8 Hz, 1H), 7.26-7.20 (m, 1H), 7.15 (t, J=8.9 Hz, 2H), 7.02 (s, 1H), 6.39 (d, J=5.2 Hz, 1H), 4.35 (s, 4H), 3.97 (d, J=7.1 Hz, 2H), 1.47 (d, J=2.1 Hz, 4H), 1.36-1.25 (m, 1H), 0.73-0.55 (m, 2H), 0.43-0.31 (m, 2H). MS: 588 [M+H]$^+$.

Example 12. N-(4-((5-(isobutyloxy)-2,3-dihydro-[1,4]dioxino[2,3-f]quinolin-10-yl)oxy)-3-fluorophenyl)-N-(4-fluorophenyl)cyclopropan-1,1-dicarboxamide

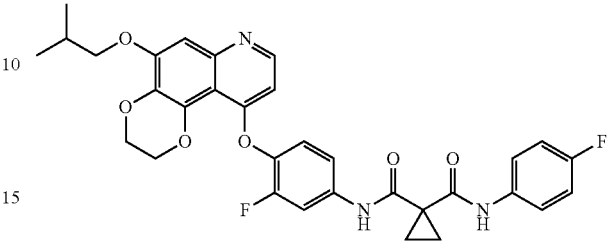

The preparation was carried out in a similar manner to Example 7, except that in step 3, an equimolar equivalent of isobutyl bromide was used in place of bromoethane to afford a white solid product; $^1$H NMR (400 MHz, DMSO-d$_6$) δ 10.31 (s, 1H), 9.99 (s, 1H), 8.41 (d, J=5.2 Hz, 1H), 7.85 (dd, J=13.3, 2.4 Hz, 1H), 7.69-7.57 (m, 2H), 7.50-7.39 (m, 1H), 7.23 (t, J=9.0 Hz, 1H), 7.18-7.11 (m, 2H), 7.05 (s, 1H), 6.40 (dd, J=5.2, 1.0 Hz, 1H), 4.35 (s, 4H), 3.90 (d, J=6.5 Hz, 2H), 2.11 (dt, J=13.3, 6.7 Hz, 1H), 1.47 (d, J=2.0 Hz, 4H), 1.03 (d, J=6.7 Hz, 6H). MS: 590 [M+H]$^+$.

Example 13. N-(3-fluoro-4-((5-(3-hydroxypropoxy)-2,3-dihydro-[1,4]dioxino[2,3-f]quinolin-10-yl)oxy)phenyl)-N-(4-fluorophenyl)cyclopropan-1,1-dicarboxamide

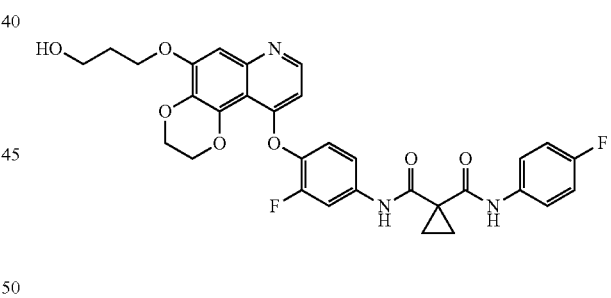

The preparation was carried out in a similar manner to Example 7, except that in step 3, an equimolar equivalent of 3-bromopropanol was used in place of bromoethane to afford a white solid product; $^1$H NMR (600 MHz, DMSO-d$_6$) δ 10.32 (s, 1H), 10.00 (s, 1H), 8.41 (dd, J=5.2, 0.9 Hz, 1H), 7.86 (d, J=12.6 Hz, 1H), 7.63 (dd, J=9.0, 4.9 Hz, 2H), 7.45 (d, J=9.0 Hz, 1H), 7.24 (t, J=9.0 Hz, 1H), 7.15 (t, J=8.9 Hz, 2H), 7.06 (s, 1H), 6.39 (d, J=5.2 Hz, 1H), 4.60 (t, J=5.1 Hz, 1H), 4.35 (s, 4H), 4.19 (t, J=6.4 Hz, 2H), 3.60 (q, J=5.9 Hz, 2H), 1.95 (t, J=6.3 Hz, 2H), 1.46 (q, J=3.3 Hz, 4H). MS: 592 [M+H]$^+$.

Example 14. N-(3-fluoro-4-((5-(3-methoxy-propoxy)-2,3-dihydro-[1,4]dioxino[2,3-f]quinolin-10-yl)oxy)phenyl)-N-(4-fluorophenyl)cyclopropan-1,1-dicarboxamide

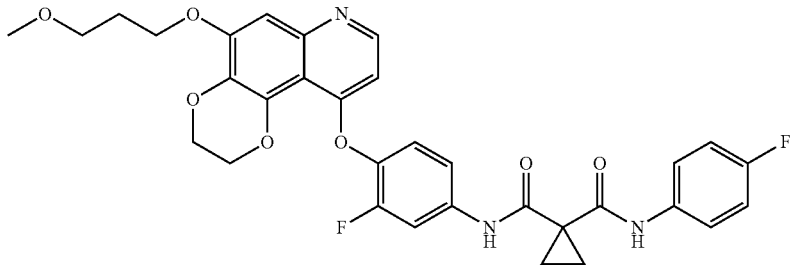 [SMILES: COCCCOc1cc2nccc(Oc3ccc(NC(=O)C4(C(=O)Nc5ccc(F)cc5)CC4)cc3F)c2c2c1OCCO2]

The preparation was carried out in a similar manner to Example 7, except that in step 3, an equimolar equivalent of methoxypropyl bromide was used in place of bromoethane to afford a white solid product; $^1$H NMR (600 MHz, DMSO-d$_6$) δ 10.32 (s, 1H), 10.00 (s, 1H), 8.41 (d, J=5.2 Hz, 1H), 7.99-7.81 (m, 1H), 7.63 (dd, J=9.0, 5.1 Hz, 2H), 7.45 (d, J=9.0 Hz, 1H), 7.24 (t, J=9.0 Hz, 1H), 7.15 (t, J=8.9 Hz, 2H), 7.06 (s, 1H), 6.40 (d, J=5.2 Hz, 1H), 4.35 (s, 4H), 4.17 (t, J=6.4 Hz, 2H), 3.51 (t, J=6.3 Hz, 2H), 3.27 (s, 3H), 2.03 (t, J=6.4 Hz, 2H), 1.46 (q, J=3.4 Hz, 4H). MS: 606[M+H]$^+$.

Example 15. N-(3-fluoro-4-((5-(3-((2-methoxyethyl)(methyl)amino)propoxy)-2,3-dihydro-[1,4]dioxino[2,3-f]quinolin-10-yl)oxy)phenyl)-N-(4-fluorophenyl)cyclopropan-1,1-dicarboxamide

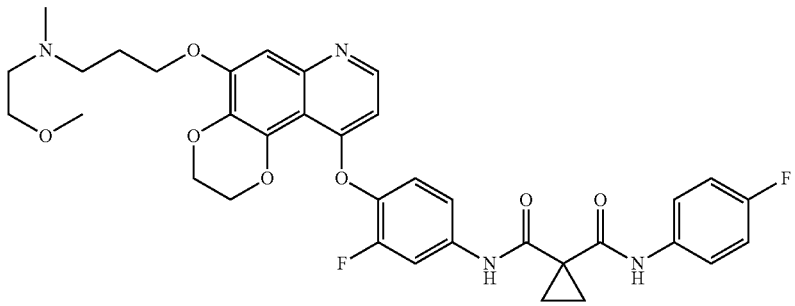 [SMILES: COCCN(C)CCCOc1cc2nccc(Oc3ccc(NC(=O)C4(C(=O)Nc5ccc(F)cc5)CC4)cc3F)c2c2c1OCCO2]

The preparation was carried out in a similar manner to Example 7, except that in step 3, an equimolar equivalent of 3-bromo-N-(2-methoxyethyl)-N-methylpropan-1-amine was used in place of bromoethane to afford a white solid product; $^1$H NMR (600 MHz, DMSO-d$_6$) δ 10.33 (s, 1H), 10.01 (s, 1H), 8.41 (d, J=5.2 Hz, 1H), 7.86 (dd, J=13.2, 2.4 Hz, 1H), 7.68-7.59 (m, 2H), 7.45 (dt, J=8.8, 1.6 Hz, 1H), 7.24 (t, J=9.0 Hz, 1H), 7.20-7.09 (m, 2H), 7.05 (s, 1H), 6.39 (d, J=5.2 Hz, 1H), 4.35 (s, 4H), 4.15 (t, J=6.4 Hz, 2H), 3.41 (t, J=5.9 Hz, 2H), 3.21 (s, 3H), 2.52 (td, J=6.6, 6.1, 4.4 Hz, 4H), 2.22 (s, 3H), 1.93 (q, J=6.7 Hz, 2H), 1.47 (q, J=3.3, 2.9 Hz, 4H). MS: 663 [M+H]$^+$.

Example 16. N-(3-fluoro-4-((5-isopropoxy-2,3-dihydro-[1,4]dioxino[2,3-f]quinolin-10-yl)oxy)phenyl)-N-(4-fluorophenyl)cyclopropan-1,1-dicarboxamide

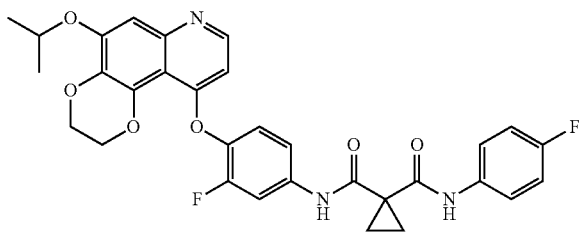 [SMILES: CC(C)Oc1cc2nccc(Oc3ccc(NC(=O)C4(C(=O)Nc5ccc(F)cc5)CC4)cc3F)c2c2c1OCCO2]

The preparation was carried out in a similar manner to Example 7, except that in step 3, an equimolar equivalent of isopropyl bromide was used in place of bromoethane to afford a white solid product; $^1$H NMR (600 MHz, DMSO-d$_6$) δ 10.32 (s, 1H), 10.00 (s, 1H), 8.40 (d, J=5.2 Hz, 1H), 7.86 (dd, J=13.2, 2.5 Hz, 1H), 7.65-7.62 (m, 2H), 7.45 (dd, J=8.9, 1.9 Hz, 1H), 7.22 (d, J=9.1 Hz, 1H), 7.17-7.13 (m, 2H), 7.06 (s, 1H), 6.38 (d, J=5.2 Hz, 1H), 4.82-4.80 (m, 1H), 4.34 (s, 4H), 1.47 (t, J=3.5 Hz, 4H), 1.36 (d, J=6.0 Hz, 6H). MS: 576[M+H]$^+$.

Example 17. N-(3-fluoro-4-((5-((tetrahydrofuran-3-yl)oxy)-2,3-dihydro-[1,4]dioxino[2,3-f]quinolin-10-yl)oxy)phenyl)-N-(4-fluorophenyl)cyclopropan-1,1-dicarboxamide

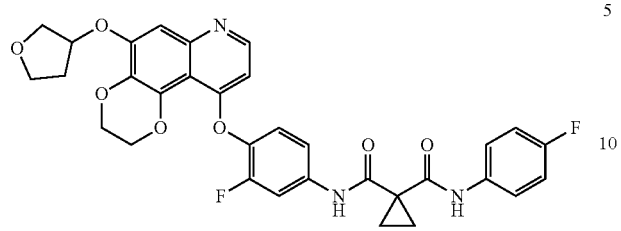

The preparation was carried out in a similar manner to Example 7, except that in step 3, an equimolar equivalent of tetrahydrofuran-3-yl p-toluenesulfonate was used in place of bromoethane to afford a white solid product; $^1$H NMR (600 MHz, DMSO-$d_6$) δ 10.33 (s, 1H), 10.00 (s, 1H), 8.42 (d, J=5.2 Hz, 1H), 7.86 (dd, J=13.2, 2.4 Hz, 1H), 7.67-7.57 (m, 2H), 7.45 (dd, J=8.4, 2.1 Hz, 1H), 7.24 (t, J=9.0 Hz, 1H), 7.15 (t, J=8.9 Hz, 2H), 7.03 (s, 1H), 6.40 (d, J=5.2 Hz, 1H), 5.24-5.16 (m, 1H), 4.35 (s, 4H), 3.96 (dd, J=10.3, 4.5 Hz, 1H), 3.92-3.84 (m, 2H), 3.78 (td, J=8.3, 4.7 Hz, 1H), 2.36-2.29 (m, 1H), 2.09-2.03 (m, 1H), 1.47 (q, J=3.3 Hz, 4H). MS: 604[M+H]$^+$.

Example 18. N-(3-fluoro-4-((5-((tetrahydropyran-4-yl)oxy)-2,3-dihydro-[1,4]dioxino[2,3-f]quinolin-10-yl)oxy)phenyl)-N-(4-fluorophenyl)cyclopropan-1,1-dicarboxamide

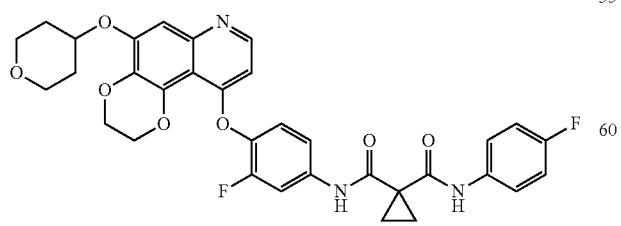

The preparation was carried out in a similar manner to Example 7, except that in step 3, an equimolar equivalent of tetrahydropyran-4-yl p-toluenesulfonate was used in place of bromoethane to afford a white solid product; $^1$H NMR (600 MHz, DMSO-$d_6$) δ 10.33 (s, 1H), 10.00 (s, 1H), 8.41 (d, J=5.2 Hz, 1H), 7.90-7.81 (m, 1H), 7.63 (dd, J=9.0, 5.1 Hz, 2H), 7.46 (d, J=8.8 Hz, 1H), 7.24 (t, J=9.1 Hz, 1H), 7.18-7.14 (m, 3H), 6.39 (d, J=5.2 Hz, 1H), 4.80 (dt, J=9.0, 4.7 Hz, 1H), 4.35 (s, 4H), 3.89 (dt, J=11.6, 4.3 Hz, 2H), 3.55 (ddd, J=12.0, 9.8, 2.7 Hz, 2H), 2.07 (d, J=10.7 Hz, 2H), 1.67 (dtd, J=13.2, 9.3, 4.1 Hz, 2H), 1.50-1.39 (m, 4H). MS: 618 [M+H]$^+$.

Example 19. N-(4-((5-(3-(4-(acetylpiperazin-1-yl)propoxy)-2,3-dihydro-[1,4]dioxino[2,3-f]quinolin-10-yl)oxy)-3-fluorophenyl)-N-(4-fluorophenyl)cyclopropan-1,1-dicarboxamide

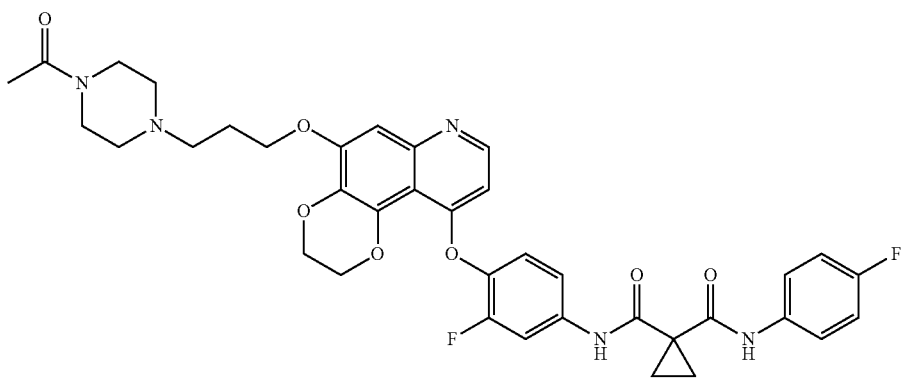 [SMILES: CC(=O)N1CCN(CCCOc2cc3nccc(Oc4ccc(NC(=O)C5(C(=O)Nc6ccc(F)cc6)CC5)cc4F)c3c3c2OCCO3)CC1]

The preparation was carried out in a similar manner to Example 7, except that in step 3, an equimolar equivalent of 4-acetylpiperazin-1-ylpropyl chloride was used in place of bromoethane to afford a white solid product; $^1$H NMR (400 MHz, DMSO-$d_6$) δ 10.26 (s, 1H), 9.93 (s, 1H), 8.35 (d, J=5.2 Hz, 1H), 7.79 (dd, J=13.3, 2.4 Hz, 1H), 7.64-7.49 (m, 2H), 7.42-7.33 (m, 1H), 7.17 (t, J=9.1 Hz, 1H), 7.12-7.05 (m, 2H), 7.01 (s, 1H), 6.36-6.25 (m, 1H), 4.29 (s, 4H), 4.12 (t, J=6.4 Hz, 2H), 3.38 (s, 4H), 2.48 (br, 2H), 2.41-2.11 (m, 4H), 1.93 (s, 5H), 1.40 (q, J=3.2 Hz, 4H). MS: 702 [M+H]$^+$.

Example 20. N-(4-((5-(cyanomethoxy)-2,3-dihydro-[1,4]dioxino[2,3-f]quinolin-10-yl)oxy)-3-fluorophenyl)-N-(4-fluorophenyl)cyclopropan-1,1-dicarboxamide

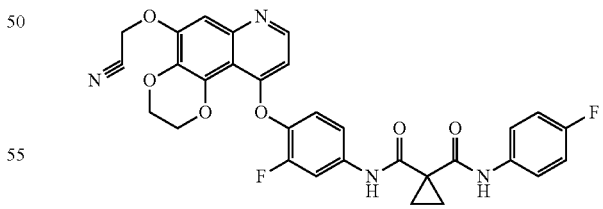

The preparation was carried out in a similar manner to Example 7, except that in step 3, an equimolar equivalent of bromoacetonitrile was used in place of bromoethane to afford a white solid product; $^1$H NMR (400 MHz, DMSO-$d_6$) δ 10.34 (s, 1H), 10.00 (s, 1H), 8.47 (d, J=5.2 Hz, 1H), 7.87 (dd, J=13.3, 2.4 Hz, 1H), 7.68-7.59 (m, 2H), 7.50-7.43 (m, 1H), 7.33-7.23 (m, 2H), 7.20-7.10 (m, 2H), 6.49-6.43 (m, 1H), 5.38 (s, 2H), 4.38 (s, 4H), 1.47 (q, J=3.4 Hz, 4H). MS: 573[M+H]$^+$.

Example 21. N-(4-((5-(3-(4-methylpiperazin-1-yl)propoxy)-2,3-dihydro-[1,4]dioxino[2,3-f]quinolin-10-yl)oxy)-3-fluorophenyl)-N-(4-fluorophenyl)cyclopropan-1,1-dicarboxamide

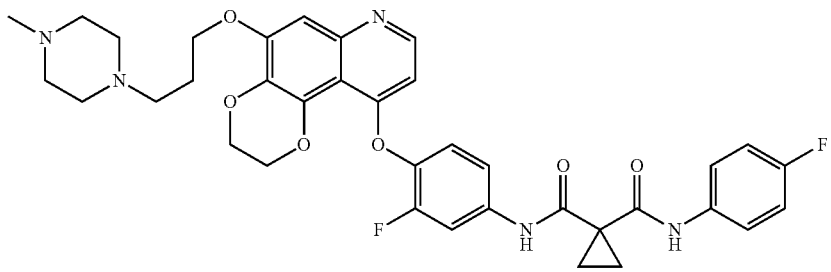 [SMILES: CN1CCN(CCCOc2cc3nccc(Oc4ccc(NC(=O)C5(C(=O)Nc6ccc(F)cc6)CC5)cc4F)c3c3c2OCCO3)CC1]

The preparation was carried out in a similar manner to Example 7, except that in step 3, an equimolar equivalent of 4-methylpiperazin-1-ylpropyl bromide was used in place of bromoethane to afford a white solid product; $^1$H NMR (600 MHz, DMSO-$d_6$) δ 10.32 (s, 1H), 10.00 (s, 1H), 8.41 (dd, J=5.2, 1.4 Hz, 1H), 7.86 (d, J=13.2 Hz, 1H), 7.63 (dd, J=8.7, 5.1 Hz, 2H), 7.45 (d, J=8.9 Hz, 1H), 7.24 (t, J=9.2 Hz, 1H), 7.15 (td, J=8.8, 1.5 Hz, 2H), 7.05 (d, J=1.4 Hz, 1H), 6.39 (d, J=5.3 Hz, 1H), 4.35 (s, 4H), 4.18-4.13 (m, 2H), 2.45 (t, J=7.2 Hz, 2H), 2.40-2.29 (m, 8H), 2.14 (s, 3H), 1.94 (t, J=6.9 Hz, 2H), 1.47 (d, J=3.8 Hz, 4H). MS: 674[M+H]$^+$.

Example 22. N-(3-fluoro-4-((5-(3-(4-hydroxy-4-methylpiperidin-1-yl)propoxy)-2,3-dihydro-[1,4]dioxino[2,3-f]quinolin-10-yl)oxy)phenyl)-N-(4-fluorophenyl)cyclopropan-1,1-dicarboxamide

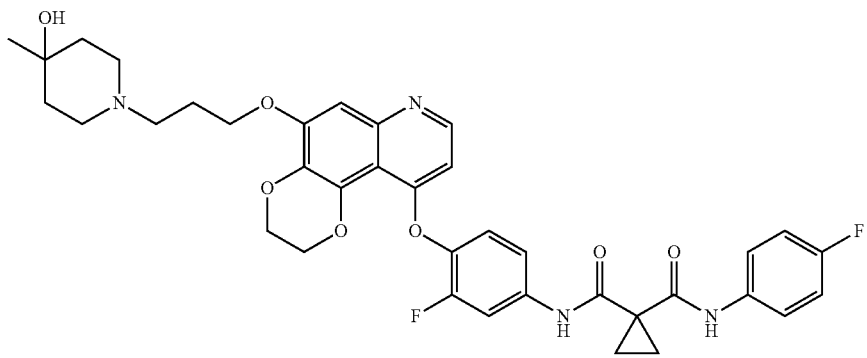 [SMILES: CC1(O)CCN(CCCOc2cc3nccc(Oc4ccc(NC(=O)C5(C(=O)Nc6ccc(F)cc6)CC5)cc4F)c3c3c2OCCO3)CC1]

The preparation was carried out in a similar manner to Example 7, except that in step 3, an equimolar equivalent of (4-hydroxy-4-methylpiperidin-1-yl)propyl bromide was used in place of bromoethane to afford a white solid product; $^1$H NMR (600 MHz, DMSO-$d_6$) δ 10.33 (s, 1H), 10.00 (s, 1H), 8.41 (d, J=5.2 Hz, 1H), 7.86 (dd, J=13.1, 2.4 Hz, 1H), 7.66-7.60 (m, 2H), 7.45 (dt, J=8.5, 1.7 Hz, 1H), 7.24 (t, J=9.0 Hz, 1H), 7.17-7.11 (m, 2H), 7.05 (s, 1H), 6.39 (d, J=5.2 Hz, 1H), 4.35 (s, 4H), 4.16 (t, J=6.4 Hz, 2H), 2.50 (br, 4H), 2.42 (br, 2H), 2.01-1.90 (m, 2H), 1.55-1.42 (m, 8H), 1.10 (s, 3H). MS: 689[M+H]$^+$.

Example 23. N-(4-((5-(3-(cyclobutyl(methyl)amino)propoxy)-2,3-dihydro-[1,4]dioxino[2,3-f]quinolin-10-yl)oxy)-3-fluorophenyl)-N-(4-fluorophenyl)cyclopropan-1,1-dicarboxamide

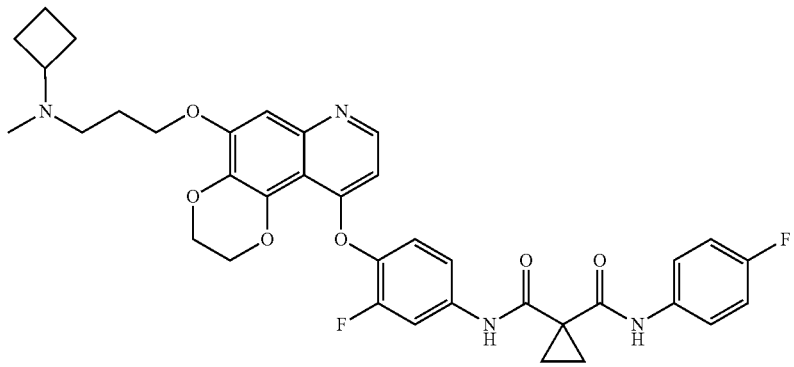 [SMILES: CN(CCCOc1cc2nccc(Oc3ccc(NC(=O)C4(C(=O)Nc5ccc(F)cc5)CC4)cc3F)c2c2c1OCCO2)C1CCC1]

The preparation was carried out in a similar manner to Example 7, except that in step 3, an equimolar equivalent of 3-(cyclobutyl(methyl)amino)propyl bromide was used in place of bromoethane to afford a white solid product; $^1$H NMR (600 MHz, DMSO-$d_6$) δ 10.33 (s, 1H), 10.01 (s, 1H), 8.42 (d, J=5.2 Hz, 1H), 7.87 (dd, J=13.2, 2.5 Hz, 1H), 7.67-7.59 (m, 2H), 7.46 (dt, J=8.9, 1.7 Hz, 1H), 7.25 (t, J=9.0 Hz, 1H), 7.19-7.11 (m, 2H), 7.06 (s, 1H), 6.40 (d, J=5.2 Hz, 1H), 4.35 (s, 4H), 4.16 (t, J=6.4 Hz, 2H), 2.79 (t, J=7.6 Hz, 1H), 2.38 (t, J=7.0 Hz, 2H), 2.06 (s, 3H), 2.02-1.94 (m, 2H), 1.91 (p, J=6.7 Hz, 2H), 1.76 (ddd, J=11.2, 6.4, 2.2 Hz, 2H), 1.65-1.55 (m, 2H), 1.47 (dd, J=4.4, 3.0 Hz, 4H). MS: 659[M+H]$^+$.

Example 24. N-(4-((5-(3-(1,1-dioxothiomorpholin-4-yl)propoxy)-2,3-dihydro-[1,4]dioxino[2,3-f]quinolin-10-yl)oxy)-3-fluorophenyl)-N-(4-fluorophenyl)cyclopropan-1,1-dicarboxamide

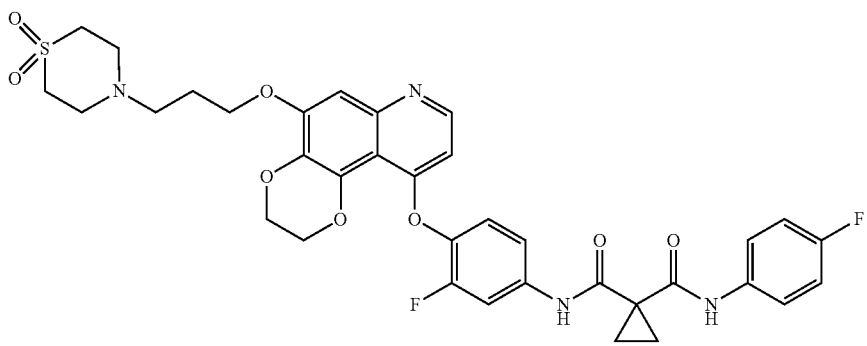 [SMILES: O=C(Nc1ccc(F)cc1)C1(C(=O)Nc2ccc(Oc3ccnc4cc(OCCCN5CCS(=O)(=O)CC5)c5c(c34)OCCO5)c(F)c2)CC1]

The preparation was carried out in a similar manner to Example 7, except that in step 3, an equimolar equivalent of 3-(1,1-dioxothiomorpholin-4-yl)propyl bromide was used in place of bromoethane to afford a white solid product; $^1$H NMR (600 MHz, DMSO-$d_6$) δ 10.33 (s, 1H), 10.00 (s, 1H), 8.41 (d, J=5.2 Hz, 1H), 7.86 (dd, J=13.2, 2.4 Hz, 1H), 7.63 (dd, J=8.9, 5.2 Hz, 2H), 7.45 (dd, J=8.9, 2.3 Hz, 1H), 7.24 (t, J=9.0 Hz, 1H), 7.15 (t, J=8.9 Hz, 2H), 7.09 (s, 1H), 6.39 (d, J=5.2 Hz, 1H), 4.35 (s, 4H), 4.18 (t, J=6.4 Hz, 2H), 3.11 (t, J=5.2 Hz, 4H), 2.92 (dd, J=7.2, 3.5 Hz, 4H), 2.65 (t, J=7.0 Hz, 2H), 1.96 (p, J=6.7 Hz, 2H), 1.47 (q, J=3.3 Hz, 4H). MS: 709[M+H]$^+$.

Example 25. N-(3-fluoro-4-((5-(3-(pyrrolidin-1-yl)propoxy)-2,3-dihydro-[1,4]dioxino[2,3-f]quinolin-10-yl)oxy)phenyl)-N-(4-fluorophenyl)cyclopropan-1,1-dicarboxamide

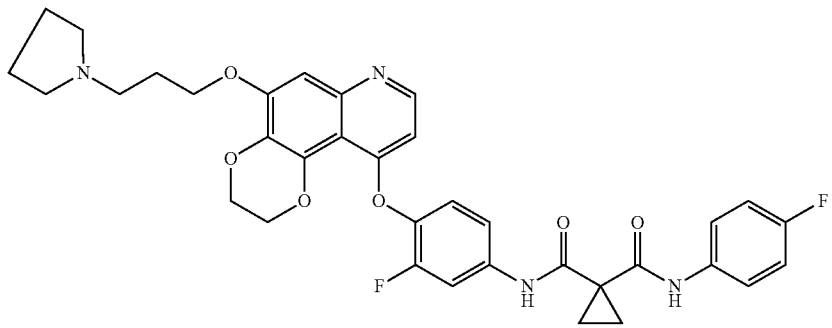 [SMILES: O=C(Nc1ccc(F)cc1)C1(C(=O)Nc2ccc(Oc3ccnc4cc(OCCCN5CCCC5)c5c(c34)OCCO5)c(F)c2)CC1]

The preparation was carried out in a similar manner to Example 7, except that in step 3, an equimolar equivalent of 3-(pyrrolidin-1-yl)propyl bromide was used in place of bromoethane to afford a white solid product; $^1$H NMR (600 MHz, DMSO-$d_6$) δ 10.34 (s, 1H), 10.01 (s, 1H), 8.41 (d, J=5.2 Hz, 1H), 7.86 (dd, J=13.1, 2.4 Hz, 1H), 7.63 (dd, J=8.9, 5.0 Hz, 2H), 7.45 (dd, J=8.9, 2.3 Hz, 1H), 7.24 (t, J=9.0 Hz, 1H), 7.15 (t, J=8.8 Hz, 2H), 7.06 (s, 1H), 6.40 (d, J=5.2 Hz, 1H), 4.35 (s, 4H), 4.18 (t, J=6.4 Hz, 2H), 2.73 (t, J=7.3 Hz, 2H), 2.66 (d, J=5.9 Hz, 4H), 2.03 (q, J=6.9 Hz, 2H), 1.80-1.68 (m, 4H), 1.47 (t, J=3.9 Hz, 4H). MS: 645 [M+H]$^+$.

Example 26. N-(3-fluoro-4-((5-(3-cyanopropoxy)-2,3-dihydro-[1,4]dioxino[2,3-f]quinolin-10-yl)oxy)phenyl)-N-(4-fluorophenyl)cyclopropan-1,1-dicarboxamide

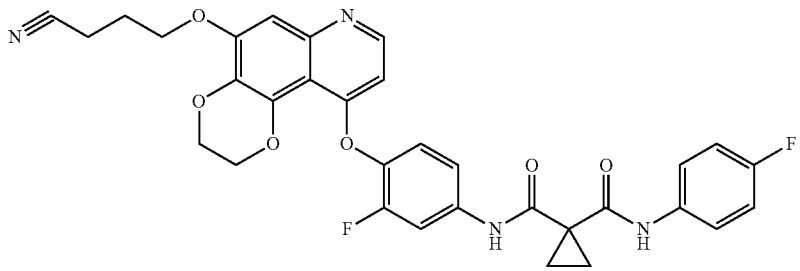 [SMILES: N#CCCCOc1cc2nccc(Oc3ccc(NC(=O)C4(C(=O)Nc5ccc(F)cc5)CC4)cc3F)c2c2c1OCCO2]

The preparation was carried out in a similar manner to Example 7, except that in step 3, an equimolar equivalent of bromobutyronitrile was used in place of bromoethane to afford a white solid product; $^1$H NMR (600 MHz, DMSO-$d_6$) δ 10.33 (s, 1H), 10.00 (s, 1H), 8.42 (d, J=5.2 Hz, 1H), 7.86 (dd, J=13.2, 2.4 Hz, 1H), 7.63 (dd, J=9.0, 5.1 Hz, 2H), 7.45 (dd, J=9.0, 2.3 Hz, 1H), 7.24 (t, J=9.0 Hz, 1H), 7.15 (t, J=8.9 Hz, 2H), 7.10 (s, 1H), 6.41 (d, J=5.2 Hz, 1H), 4.36 (s, 4H), 4.20 (t, J=6.1 Hz, 2H), 2.69 (t, J=7.2 Hz, 2H), 2.12 (p, J=6.7 Hz, 2H), 1.47 (t, J=3.6 Hz, 4H). MS: 601[M+H]$^+$.

Example 27. N-(4-((5-((6-(dimethylamino)hexyl) oxy)-2,3-dihydro-[1,4]dioxino[2,3-f]quinolin-10-yl) oxy)-3-fluorophenyl)-N-(4-fluorophenyl) cyclopropan-1,1-dicarboxamide

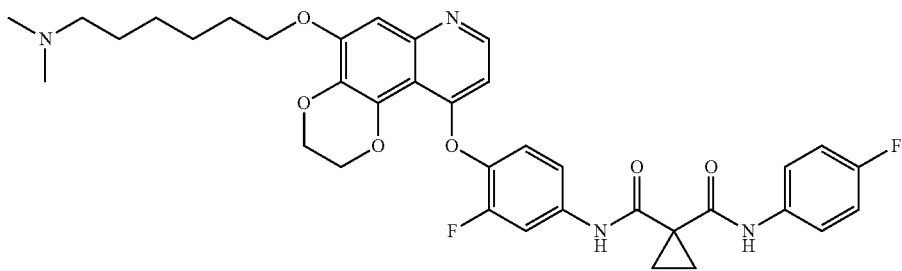 [SMILES: CN(C)CCCCCCOc1cc2nccc(Oc3ccc(NC(=O)C4(C(=O)Nc5ccc(F)cc5)CC4)cc3F)c2c2c1OCCO2]

The preparation was carried out in a similar manner to Example 7, except that in step 3, an equimolar equivalent of 6-dimethylaminohexyl bromide was used in place of bromoethane to afford a white solid product; $^1$H NMR (600 MHz, DMSO-$d_6$) δ 10.34 (s, 1H), 10.01 (s, 1H), 8.41 (d, J=5.2 Hz, 1H), 7.86 (d, J=13.0 Hz, 1H), 7.63 (dd, J=8.8, 5.1 Hz, 2H), 7.45 (d, J=8.9 Hz, 1H), 7.24 (t, J=9.0 Hz, 1H), 7.15 (t, J=8.7 Hz, 2H), 7.05 (s, 1H), 6.39 (d, J=5.2 Hz, 1H), 4.35 (s, 4H), 4.12 (t, J=6.5 Hz, 2H), 2.31 (t, J=7.4 Hz, 2H), 2.20 (s, 6H), 1.80 (q, J=7.1 Hz, 2H), 1.49-1.43 (m, 8H), 1.36 (q, J=7.8 Hz, 2H). MS: 661[M+H]$^+$.

Example 28. N-(3-fluoro-4-((5-(oxetan-3-yloxy)-2,3-dihydro-[1,4]dioxino[2,3-f]quinolin-10-yl)oxy) phenyl)-N-(4-fluorophenyl)cyclopropan-1,1-dicarboxamide

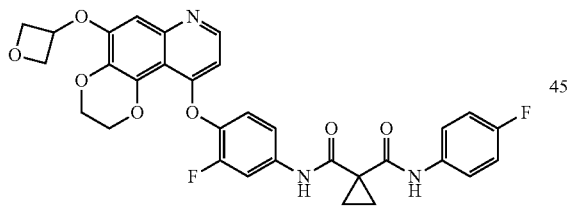

The preparation was carried out in a similar manner to Example 7, except that in step 3, an equimolar equivalent of oxetan-3-yl p-toluenesulfonate was used in place of bromoethane to afford a white solid product; $^1$H NMR (600 MHz, DMSO-$d_6$) δ 10.33 (s, 1H), 10.00 (s, 1H), 8.41 (d, J=5.2 Hz, 1H), 7.87 (d, J=13.2 Hz, 1H), 7.73-7.57 (m, 2H), 7.45 (s, 1H), 7.24 (s, 1H), 7.15 (t, J=8.8 Hz, 2H), 6.70 (s, 1H), 6.41 (d, J=5.2 Hz, 1H), 5.45 (h, J=5.1 Hz, 1H), 5.07-4.87 (m, 2H), 4.62 (dd, J=7.4, 4.9 Hz, 2H), 4.38 (s, 4H), 1.45 (s, 4H). MS: 590[M+H]$^+$.

Example 29. N-(3-fluoro-4-((5-(3-(4,4-dimethylpiperidin-1-yl)propoxy)-2,3-dihydro-[1,4]dioxino[2,3-f] quinolin-10-yl)oxy)phenyl)-N-(4-fluorophenyl)cyclopropan-1,1-dicarboxamide

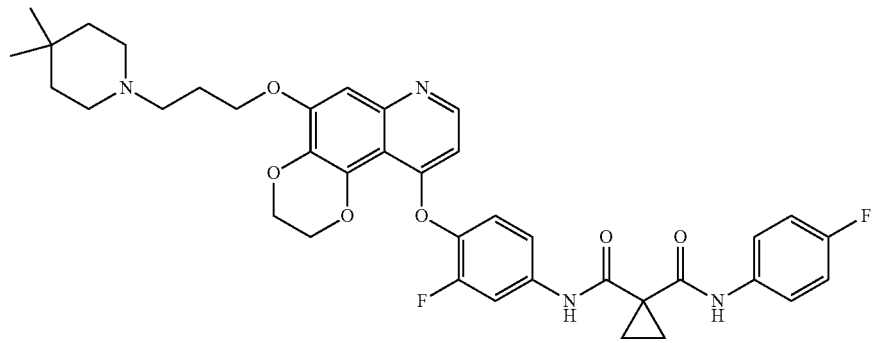 [SMILES: CC1(C)CCN(CCCOc2cc3nccc(Oc4ccc(NC(=O)C5(C(=O)Nc6ccc(F)cc6)CC5)cc4F)c3c3c2OCCO3)CC1]

The preparation was carried out in a similar manner to Example 7, except that in step 3, an equimolar equivalent of (4,4-dimethylpiperidin-1-yl)propyl bromide was used in place of bromoethane to afford a white solid product; $^1$H NMR (600 MHz, DMSO-d$_6$) δ 10.32 (s, 1H), 10.00 (s, 1H), 8.41 (d, J=5.2 Hz, 1H), 7.89-7.81 (m, 1H), 7.63 (dd, J=9.0, 5.1 Hz, 2H), 7.45 (d, J=8.7 Hz, 1H), 7.24 (t, J=9.1 Hz, 1H), 7.15 (t, J=8.9 Hz, 2H), 7.05 (s, 1H), 6.39 (d, J=5.2 Hz, 1H), 4.35 (s, 4H), 4.15 (t, J=6.4 Hz, 2H), 2.46-2.36 (m, 6H), 1.98-1.92 (m, 2H), 1.47 (q, J=3.3 Hz, 4H), 1.35-1.30 (m, 4H), 0.90 (s, 6H). MS: 687[M+H]$^+$.

Example 30. N-(3-fluoro-4-((5-(3-(4-amino-4-methylpiperidin-1-yl)propoxy)-2,3-dihydro-[1,4]dioxino[2,3-f]quinolin-10-yl)oxy)phenyl)-N-(4-fluorophenyl)cyclopropan-1,1-dicarboxamide

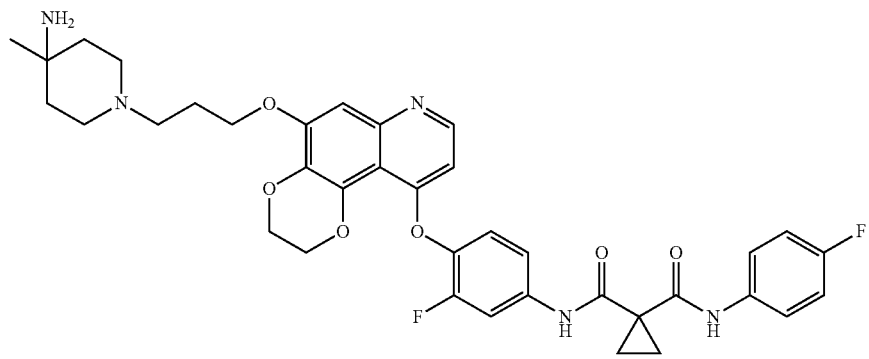 [SMILES: CC1(N)CCN(CCCOc2cc3nccc(Oc4ccc(NC(=O)C5(C(=O)Nc6ccc(F)cc6)CC5)cc4F)c3c3c2OCCO3)CC1]

The preparation was carried out in a similar manner to Example 7, except that in step 3, an equimolar equivalent of (4-amino-4-methylpiperidin-1-yl)propyl bromide was used in place of bromoethane to afford a white solid product; $^1$H NMR (600 MHz, DMSO-d$_6$) δ 10.31 (s, 1H), 9.97 (s, 1H), 8.34 (d, J=5.2 Hz, 1H), 8.30 (s, 2H), 7.79 (dd, J=13.2, 2.4 Hz, 1H), 7.61-7.50 (m, 2H), 7.39 (dt, J=8.7, 1.7 Hz, 1H), 7.17 (t, J=9.1 Hz, 1H), 7.12-7.04 (m, 2H), 6.98 (s, 1H), 6.33 (d, J=5.2 Hz, 1H), 4.28 (s, 4H), 4.09 (t, J=6.4 Hz, 2H), 2.59-2.52 (m, 4H), 2.19 (s, 2H), 1.92-1.84 (m, 2H), 1.66-1.48 (m, 4H), 1.40 (dd, J=5.4, 3.6 Hz, 4H), 1.14 (s, 3H). MS: 688[M+H]$^+$.

Example 31. N-(3-chloro-4-((5-(3-morpholinopropoxy)-2,3-dihydro-[1,4]dioxino[2,3-f]quinolin-10-yl)oxy)phenyl)-N-(4-fluorophenyl)cyclopropan-1,1-dicarboxamide

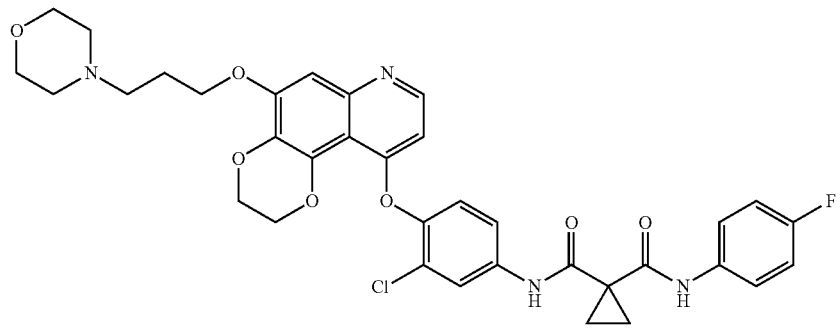 [SMILES: O=C(Nc1ccc(F)cc1)C1(C(=O)Nc2ccc(Oc3ccnc4cc(OCCCN5CCOCC5)c5c(c34)OCCO5)c(Cl)c2)CC1]

The preparation was carried out in a similar manner to Example 7, except that in step 1, 2-chloro-4-nitrophenol was used in place of 2-fluoro-4-nitrophenol, and in step 3, 4-(3-chloropropyl)morpholine was used in place of bromoethane to afford a white solid product; $^1$H NMR (600 MHz, DMSO-$d_6$) δ 10.28 (s, 1H), 10.02 (s, 1H), 8.43 (d, J=5.2 Hz, 1H), 8.05 (d, J=2.5 Hz, 1H), 7.69-7.62 (m, 2H), 7.60 (dd, J=8.9, 2.5 Hz, 1H), 7.22-7.13 (m, 3H), 7.09 (s, 1H), 6.34 (d, J=5.2 Hz, 1H), 4.38-4.30 (m, 4H), 4.20 (t, J=6.3 Hz, 2H), 3.63 (s, 4H), 2.42 (br, 6H), 2.01 (d, J=16.4 Hz, 2H), 1.47 (t, J=3.1 Hz, 4H). MS: 677[M+H]$^+$.

Example 32. N-(3-fluoro-4-((5-(2-hydroxyethoxy)-2,3-dihydro-[1,4]dioxino[2,3-f]quinolin-10-yl)oxy)phenyl)-N-(4-fluorophenyl)cyclopropan-1,1-dicarboxamide

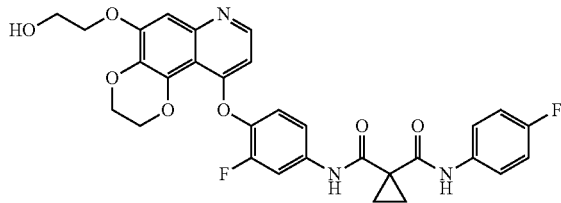 [SMILES: O=C(Nc1ccc(F)cc1)C1(C(=O)Nc2ccc(Oc3ccnc4cc(OCCO)c5c(c34)OCCO5)c(F)c2)CC1]

The preparation was carried out in a similar manner to Example 7, except that in step 3, an equimolar equivalent of 2-bromoethanol was used in place of bromoethane to afford a white solid product; $^1$H NMR (400 MHz, DMSO-$d_6$) δ 10.34 (s, 1H), 10.01 (s, 1H), 8.44 (d, J=5.3 Hz, 1H), 7.87 (dd, J=13.2, 2.4 Hz, 1H), 7.64 (dd, J=8.9, 5.1 Hz, 2H), 7.47 (dd, J=8.9, 2.3 Hz, 1H), 7.26 (t, J=9.0 Hz, 1H), 7.15 (t, J=8.9 Hz, 2H), 7.09 (s, 1H), 6.43 (d, J=5.3 Hz, 1H), 4.96 (s, 1H), 4.36 (s, 4H), 4.15 (t, J=4.9 Hz, 2H), 3.81 (t, J=4.9 Hz, 2H), 1.48 (t, J=2.9 Hz, 4H). MS: 578[M+H]$^+$.

Example 33. N-(4-((5-(((1-aminocyclopropyl)methoxy)-2,3-dihydro-[1,4]dioxino[2,3-f]quinolin-10-yl)oxy)-3-fluorophenyl)-N-(4-fluorophenyl)cyclopropan-1,1-dicarboxamide

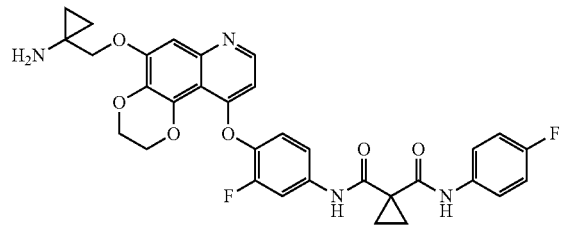 [SMILES: NC1(COc2cc3nccc(Oc4ccc(NC(=O)C5(C(=O)Nc6ccc(F)cc6)CC5)cc4F)c3c3c2OCCO3)CC1]

The preparation was carried out in a similar manner to Example 7, except that in step 3, an equimolar equivalent of (1-(((tertbutyloxycarbonyl)amino)cyclopropyl)methyl 4-methylbenzenesulfonate was used in place of bromoethane to afford a white solid product; $^1$H NMR (400 MHz, DMSO-$d_6$) δ 10.32 (s, 1H), 10.00 (s, 1H), 8.40 (d, J=5.2 Hz, 1H), 7.85 (dd, J=13.3, 2.4 Hz, 1H), 7.73-7.57 (m, 2H), 7.45 (dd, J=8.9, 2.3 Hz, 1H), 7.19 (dt, J=35.1, 9.0 Hz, 3H), 7.03 (s, 1H), 6.39 (d, J=5.1 Hz, 1H), 4.36 (q, J=4.5 Hz, 4H), 4.02 (s, 2H), 1.47 (t, J=2.9 Hz, 4H), 0.62 (dt, J=9.6, 2.1 Hz, 4H). MS: 603[M+H]$^+$.

Example 34. N-(3-fluoro-4-((5-(2-hydroxy-2-methylpropoxy)-2,3-dihydro-[1,4]dioxino[2,3-f]quinolin-10-yl)oxy)phenyl)-N-(4-fluorophenyl)cyclopropan-1,1-dicarboxamide

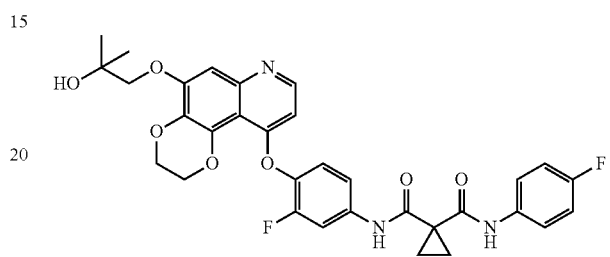

The preparation was carried out in a similar manner to Example 7, except that in step 3, an equimolar equivalent of 1-bromo-2-methylpropan-2-ol was used in place of bromoethane to afford a white solid product; $^1$H NMR (400 MHz, DMSO-$d_6$) δ 10.32 (s, 1H), 10.00 (s, 1H), 8.41 (d, J=5.2 Hz, 1H), 7.86 (dd, J=13.2, 2.4 Hz, 1H), 7.69-7.59 (m, 2H), 7.49-7.40 (m, 1H), 7.24 (t, J=9.0 Hz, 1H), 7.19-7.11 (m, 2H), 7.04 (s, 1H), 6.40 (dd, J=5.2, 1.0 Hz, 1H), 4.69 (s, 1H), 4.36 (d, J=1.8 Hz, 4H), 3.87 (s, 2H), 1.47 (t, J=2.7 Hz, 4H), 1.25 (s, 6H). MS: 606[M+H]$^+$.

Example 35. N-(2-chloro-5-fluoro-4-((5-methoxy-2,3-dihydro-[1,4]dioxino[2,3-f]quinolin-10-yl)oxy)phenyl)-N-(4-fluorophenyl)cyclopropan-1,1-dicarboxamide

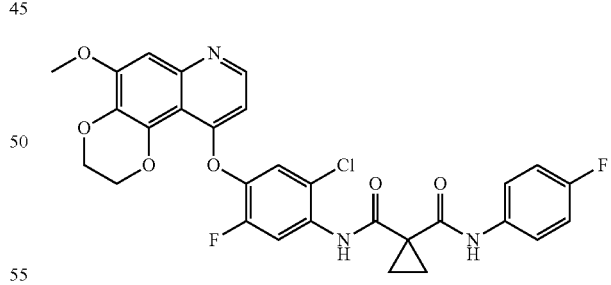

The preparation was carried out in a similar manner to Example 7, except that in step 1, an equimolar equivalent of 5-chloro-2-fluoro-4-nitrophenol was used in place of 2-fluoro-4-nitrophenol to afford a white solid product; $^1$H NMR (400 MHz, DMSO-$d_6$) δ 11.37 (s, 1H), 9.72 (s, 1H), 8.46 (d, J=5.1 Hz, 1H), 8.26 (d, J=12.8 Hz, 1H), 7.63-7.48 (m, 3H), 7.18 (t, J=8.9 Hz, 2H), 7.09 (s, 1H), 6.57 (d, J=5.2 Hz, 1H), 4.32 (s, 4H), 3.92 (s, 3H), 1.71 (s, 2H), 1.63 (s, 2H). MS: 582[M+H]$^+$.

Example 36. N-(2-chloro-4-((5-(3-morpholino-propoxy)-2,3-dihydro-[1,4]dioxino[2,3-f]quinolin-10-yl)oxy)phenyl)-N-(4-fluorophenyl)cyclopropan-1,1-dicarboxamide

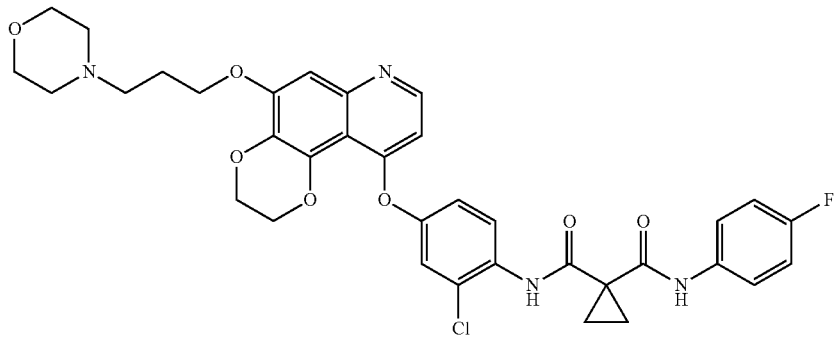 [SMILES: O=C(Nc1ccc(F)cc1)C1(C(=O)Nc2ccc(Oc3ccnc4cc(OCCCN5CCOCC5)c5c(c34)OCCO5)cc2Cl)CC1]

The preparation was carried out in a similar manner to Example 7, except that in step 1, an equimolar equivalent of 3-chloro-4-nitrophenol was used in place of 2-fluoro-4-nitrophenol, and in step 3, an equimolar equivalent of 4-(3-chloropropyl)morpholine was used in place of bromoethane to afford a white solid product; $^1$H NMR (600 MHz, DMSO-$d_6$) δ 10.83 (s, 1H), 9.89 (s, 1H), 8.51 (d, J=5.1 Hz, 1H), 8.03 (d, J=9.0 Hz, 1H), 7.59 (dd, J=8.9, 5.1 Hz, 2H), 7.28 (d, J=2.7 Hz, 1H), 7.18 (t, J=8.9 Hz, 2H), 7.13 (d, J=9.2 Hz, 1H), 7.05 (dd, J=9.0, 2.8 Hz, 1H), 6.64 (d, J=5.1 Hz, 1H), 4.36-4.14 (m, 6H), 3.84-3.63 (m, 2H), 3.26 (s, 4H), 2.51 (br, 4H), 2.26-2.11 (m, 2H), 1.66 (q, J=4.3, 3.7 Hz, 2H), 1.60 (q, J=4.9, 4.2 Hz, 2H). MS: 677[M+H]$^+$.

Biological Example 1. Assay of Small Molecular Compounds for Inhibiting the Activity of c-MET Kinase The assay is based on the LANCE TR-FRET technology of Perkin Elmer Inc., and the assay method is as follows:

1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).
2. 2.5 μL of the gradient-diluted compounds were taken with a transfer pipette to a 384-well plate.
3. Addition of enzyme: 5 μL of 2× c-MET kinase solution (concentration was 2 nM) was taken with a transfer pipette to the corresponding reaction well of the 384-well plate, mixed well and pre-reacted at room temperature for 5 minutes.
4. 2.5 μL 4× Ultra ULight™-JAK-1 (Tyr1023) Peptide (concentration was 400 nM)/ATP (concentration was 40 μM) mixture was taken with a transfer pipette to the corresponding reaction well of the 384-well plate.
5. Negative control: 2.5 μL/well 4× substrate/ATP mixture and 7.5 μL 1× Kinase Assay Buffer were added to the wells of the 384-well plate.
6. Positive control: 2.5 μL/well 4× substrate/ATP mixture, 2.5 μL/well 1× Kinase Assay Buffer containing 16% DMSO, and 5 L/well 2× c-MET kinase solution were added to the 384-well plate. The final concentration of DMSO in the reaction system was 4%.
7. The mixture was mixed well and then centrifuged and reacted at room temperature in dark for 60 min.
8. Termination of the enzymatic reaction: 5 μL of 4× stop solution was taken with a transfer pipette to the wells of the 384-well plate, mixed and then centrifuged, and reacted at room temperature for 5 min.
9. Development of the reaction: 5 μL of 4× detection solution was taken with a transfer pipette to the wells of the 384-well plate for color development, and the mixture was mixed and then centrifuged and reacted at room temperature for 60 min.
10. The 384-well plate was placed into the Envision plate reader and the signal was detected using the appropriate program.
11. Analysis and processing of the raw data:
12. The drug concentrations and the corresponding inhibition rates were input into GraphPad Prism5 for calculation, and the inhibition rate of the compounds were calculated as follows: inhibition rate (%)=(reading of positive well−reading of experimental well)/(reading of positive control well−reading of negative control well)×100%. Processing with GraphPad Prism5 software yielded the corresponding $IC_{50}$ values (the concentration of the compound at which 50% of the highest inhibition of the enzyme is achieved).

Table 1 lists the assay results of the inhibitory activity of some of the compounds disclosed herein on the c-MET tyrosine kinase, wherein A indicates that the $IC_{50}$ is less than or equal to 50 nM, B indicates that the $IC_{50}$ is greater than 50 nM but less than or equal to 500 nM, C indicates that the $IC_{50}$ is greater than 500 nM but less than or equal to 5000 nM, and D indicates that the $IC_{50}$ is greater than 5000 nM.

TABLE 1

Assay results of the inhibitory activity of the compounds disclosed herein on the c-MET tyrosine kinase

| Example No. | c-MET $IC_{50}$ (nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | B |
| 12 | B |
| 13 | A |
| 14 | A |
| 15 | A |
| 16 | A |

TABLE 1-continued

Assay results of the inhibitory activity of the compounds disclosed herein on the c-MET tyrosine kinase

| Example No. | c-MET IC$_{50}$ (nM) |
|---|---|
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |

Biological Example 2. Assay of Small Molecular Compounds for Inhibiting the Activity of VEGFR-2 Kinase The assay is based on the LANCE TR-FRET technology of Perkin Elmer Inc., and the assay method is as follows:

1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).

2. 2.5 µL of the gradient-diluted compounds were taken with a transfer pipette to a 384-well plate.

3. Addition of enzyme: 5 µL of 2× VEGFR-2 kinase solution (concentration was 0.5 nM) was taken with a transfer pipette to the corresponding reaction well of the 384-well plate, mixed well and pre-reacted at room temperature for 30 minutes.

4. 2.5 µL 4× Ultra ULight™-JAK-1 (Tyr1023) Peptide (concentration was 200 nM)/ATP (concentration was 40 µM) mixture was taken with a transfer pipette to the corresponding reaction well of the 384-well plate.

5. Negative control: 2.5 µL/well 4× substrate/ATP mixture and 7.5 µL 1× Kinase Assay Buffer were added to the wells of the 384-well plate.

6. Positive control: 2.5 µL/well 4× substrate/ATP mixture, 2.5 µL/well 1× Kinase Assay Buffer containing 16% DMSO, and 5 µL/well 2× VEGFR-2 kinase solution were added to the 384-well plate. The final concentration of DMSO in the reaction system was 4%.

7. The mixture was mixed well and then centrifuged and reacted at room temperature in dark for 60 min.

8. Termination of the enzymatic reaction: 5 µL of 4× stop solution was taken with a transfer pipette to the wells of the 384-well plate, mixed and then centrifuged, and reacted at room temperature for 5 min.

9. Development of the reaction: 5 µL of 4× detection solution was taken with a transfer pipette to the wells of the 384-well plate for color development, and the mixture was mixed and then centrifuged and reacted at room temperature for 60 min.

10. The 384-well plate was placed into the Envision plate reader and the signal was detected using the appropriate program.

11. Analysis and processing of the raw data: The drug concentrations and the corresponding inhibition rates were input into GraphPad Prism5 for calculation, and the inhibition rate of the compounds were calculated as follows: inhibition rate (%)=(reading of positive well−reading of experimental well)/(reading of positive control well−reading of negative control well)×100%. Processing with GraphPad Prism5 software yielded the corresponding IC$_{50}$ values (the concentration of the compound at which 50% of the highest inhibition of the enzyme is achieved).

Table 2 lists the assay results of the inhibitory activity of some of the compounds disclosed herein on the VEGFR-2 tyrosine kinase, wherein A indicates that the IC$_{50}$ is less than or equal to 50 nM, B indicates that the IC$_{50}$ is greater than 50 nM but less than or equal to 500 nM, C indicates that the IC$_{50}$ is greater than 500 nM but less than or equal to 5000 nM, and D indicates that the IC$_{50}$ is greater than 5000 nM.

TABLE 2

Assay results of the inhibitory activity of some of the compounds disclosed herein on the VEGFR-2 tyrosine kinase

| Example No. | VEGFR-2 IC$_{50}$ (nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 13 | A |
| 14 | A |
| 15 | A |
| 17 | A |
| 18 | B |
| 19 | A |
| 20 | B |
| 21 | A |
| 22 | A |
| 23 | A |
| 24 | A |
| 25 | A |
| 26 | A |
| 27 | A |
| 28 | A |
| 29 | A |
| 30 | A |
| 32 | A |
| 33 | A |
| 34 | A |
| 35 | D |
| 36 | B |

Biological Example 3. Assay of the Inhibitory Activity of Small Molecular Compounds on the Proliferation of MHCC97H Cells The specific steps of the assay are as follows:

1. Dilution of compounds: a total of 9 concentrations were obtained using a 3-fold gradient dilution from the highest concentration of 5000 nM (the maximum final concentration of the drug used in this assay was 5000 nM, and the minimum final concentration was 0.76 nM).

2. MHCC97H cells were collected, then transferred to a 15 mL centrifuge tube, and centrifuged at 1000 rpm for 5 minutes.

3. The supernatant was discarded, and the complete medium was added and pipetted evenly, 10 μL of cell suspension was taken out and mixed evenly with 10 μL of 0.4% trypan blue, the counting was carried out with a cell counter, and the number and survival rate of cells were recorded;

4. The cell suspension was seeded into a 96-well plate at 5000 cells/80 μL per well;

5. 20 μL of the corresponding 5× compound solution diluted with the medium mentioned above was added to each well and mixed evenly;

6. After 72 hours of incubation, 10 μL of CCK-8 reagent was added to each well and incubated for another 2 hours (the reaction time can be adjusted according to the color depth);

7. The OD value was read at 450 nm on a multi-function plate reader.

8. Data processing: cell survival rate (%)=[(As−Ab)/(Ac−Ab)]*100%

As: OD value of assay well (medium containing cells, CCK-8, compound),
Ac: OD value of control well (medium containing cells, CCK-8),
Ab: OD value of blank well (CCK-8, medium without cell and compound), The values were then imported into Graphpad Prism5 software for curve fitting, and $IC_{50}$ was calculated.

Table 3 lists the assay results of the inhibitory activity of some compounds disclosed herein on the proliferation of the MHCC97H cell line.

TABLE 3

The assay results of the inhibitory activity of some compounds disclosed herein on the proliferation of MHCC97H cells

| Example No. | MHCC97H $IC_{50}$ (nM) |
|---|---|
| 1 | <50 |
| 2 | <50 |
| 3 | <50 |
| 4 | <50 |
| 5 | <50 |
| 6 | <50 |
| 7 | <50 |
| 8 | <50 |
| 9 | <50 |
| 10 | <50 |
| 13 | <50 |
| 14 | <50 |
| 15 | <50 |
| 17 | <50 |
| 19 | <50 |
| 20 | <50 |
| 21 | <50 |
| 22 | <50 |
| 23 | <50 |
| 24 | <50 |
| 25 | <50 |
| 26 | <50 |
| 27 | <50 |
| 28 | <50 |
| 29 | <50 |
| 30 | <500 |
| 32 | <50 |
| 33 | <50 |
| 35 | <50 |
| 36 | <50 |

The biological data provided by the present disclosure indicate that the compounds disclosed herein are useful for treating or preventing diseases caused by abnormalities of VEGFR-2 or c-MET kinase. Therefore, the compounds disclosed herein are useful in the treatment of cancer, including primary and metastatic cancers, including solid tumors. Such cancers include, but are not limited to, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myeloid leukemia, non-Hodgkin's lymphoma, nasopharyngeal carcinoma, esophageal cancer, brain tumor, B-cell and T-cell lymphoma, lymphoma, multiple myeloma, biliary cancer and sarcoma, cholangiocarcinoma, etc. The compounds disclosed herein also treat cancers that are resistant to one or more other therapeutic methods. The compounds disclosed herein can also be used for other diseases (besides cancer) related to VEGFR-2 kinase and/or c-MET kinase, including but not limited to ocular fundus diseases, psoriasis, rheumatic arthritis, atherosclerosis, pulmonary fibrosis, and liver fibrosis. The compounds disclosed herein can be used as monotherapy or combination therapy, and can be used in combination with multiple compounds disclosed herein or in combination with other drugs than the present disclosure.

The above-mentioned embodiments are only preferred embodiments of the present disclosure and are not intended to limit the present disclosure. Any modification, equivalent replacement and improvement made within the spirit and principle of the present disclosure should be included within the protection scope of the present disclosure.

What is claimed is:

1. A compound of formula (I), or a pharmaceutically acceptable salt, an enantiomer, a diastereomer, a hydrate, or a solvate thereof,

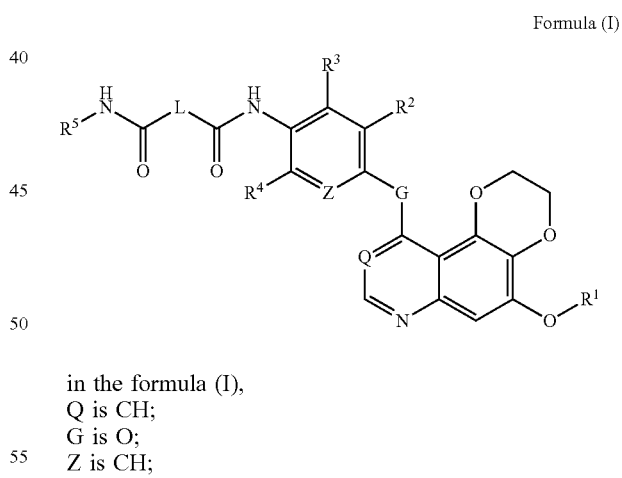

Formula (I)

in the formula (I),
Q is CH;
G is O;
Z is CH;
L is selected from the group consisting of

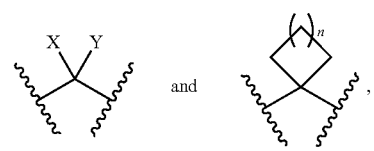

and, wherein X is H or $C_1$-$C_3$ alkyl; Y is H or $C_1$-$C_3$ alkyl; n is 0 to 3, and when n is 0, L represents

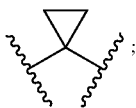 [SMILES: *C1(*)CC1];

R¹ is H, $C_1$-$C_9$ alkyl, $C_3$-$C_7$ cycloalkyl, 4- to 7-membered heterocyclyl, $C_1$-$C_6$ alkyl substituted with $C_3$-$C_7$ cycloalkyl, $C_1$-$C_6$ alkyl substituted with 4- to 7-membered heterocyclyl, or $C_1$-$C_9$ alkyl substituted with one or more of the following: hydroxyl, $C_1$-$C_6$ alkoxy, $C_1$-$C_6$ alkylthio or —$NR^6R^7$, R⁶ and R⁷ are each independently H, $C_1$-$C_6$ alkyl, $C_1$-$C_6$ alkyl substituted with hydroxyl, or $C_1$-$C_6$ alkyl substituted with $C_1$-$C_3$ alkoxy;

each of the above 4- to 7-membered heterocyclyl is a 4- to 7-membered heterocyclyl containing 1 to 2 atoms selected from the group consisting of N, O, and S, which is unsubstituted, or is substituted with $C_1$-$C_3$ alkyl or $C_1$-$C_3$ acyl, or is oxidized by 1 to 2 oxygen atoms;

R² is H, $C_1$-$C_3$ alkyl or halogen;
R³ is H, $C_1$-$C_3$ alkyl or halogen;
R⁴ is H, $C_1$-$C_3$ alkyl or halogen;
R⁵ is H, $C_1$-$C_9$ alkyl, $C_3$-$C_7$ cycloalkyl, $C_1$-$C_6$ alkyl substituted with $C_3$-$C_7$ cycloalkyl, aryl, $C_1$-$C_6$ alkyl substituted with aryl, heteroaryl, or $C_1$-$C_6$ alkyl substituted with heteroaryl;

each of the above aryl and heteroaryl are unsubstituted, or substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl, aryloxy and methylsulfonyl; and each of the above heteroaryl is a monocyclic or bicyclic group containing 1 to 3 heteroatoms selected from the group consisting of N, O, and S, and containing 5 to 10 ring atoms.

2. The compound, or the pharmaceutically acceptable salt, the enantiomer, a diastereomer, a hydrate, or a solvate thereof according to claim 1, wherein R¹ is H, $C_1$-$C_6$ alkyl, $C_3$-$C_6$ cycloalkyl, 5- to 6-membered heterocyclyl, $C_1$-$C_3$ alkyl substituted with $C_3$-$C_6$ cycloalkyl, $C_1$-$C_3$ alkyl substituted with 5- to 6-membered heterocyclyl, or $C_1$-$C_6$ alkyl substituted with the following: hydroxyl, $C_1$-$C_3$ alkoxy, $C_1$-$C_3$ alkylthio or —$NR^6R^7$, R⁶ and R⁷ are each independently —H, $C_1$-$C_3$ alkyl, $C_1$-$C_3$ alkyl substituted with hydroxyl, or $C_1$-$C_3$ alkyl substituted with $C_1$-$C_3$ alkoxy; and each of the above 5- to 6-membered heterocyclyl is a 5- to 6-membered heterocyclyl containing 1 to 2 atoms selected from the group consisting of N, O, and S, which is unsubstituted, or is substituted with $C_1$-$C_3$ alkyl or $C_1$-$C_3$ acyl, or is oxidized by 1 to 2 oxygen atoms.

3. The compound, or the pharmaceutically acceptable salt, the enantiomer, a diastereomer, a hydrate, or a solvate thereof according to claim 1, wherein R¹ is selected from the group consisting of one or more of the following: methyl, ethyl, propyl, isopropyl, methoxyethyl, methoxypropyl, methoxybutyl, methoxypentyl, methoxyhexyl, tetrahydrofuran-3-yl, tetrahydro-2H-pyran-4-yl, tetrahydropyrrol-1-ylethyl, tetrahydropyrrol-1-ylpropyl, piperidin-1-ylethyl, piperidin-1-ylpropyl, piperazin-1-ylethyl, piperazin-1-ylpropyl, morpholin-4-ylethyl, morpholin-4-ylpropyl, methylpiperazin-4-ylethyl, methylpiperazin-4-ylpropyl, N-formylpiperazin-4-ylethyl, N-formylpiperazin-4-ylpropyl, N-acetylpiperazin-4-ylethyl, N-acetylpiperazin-4-ylpropyl, (1,1-dioxothiomorpholin)-4-ylethyl, (1,1-dioxothiomorpholin)-4-ylpropyl, methylthioethyl, methylthiopropyl, dimethylaminoethyl, dimethylaminopropyl, dimethylaminobutyl, dimethylaminopentyl, dimethylaminohexyl, diethylaminoethyl, diethylaminopropyl, hydroxyethyl, hydroxypropyl, hydroxyethylaminoethyl, hydroxypropylaminoethyl, hydroxyethylaminopropyl, methoxyethylaminoethyl, methoxypropylaminoethyl, methoxyethylaminopropyl, aminoethyl, aminopropyl, aminobutyl, N-methyl-N-hydroxyethylaminoethyl, N-methyl-N-hydroxypropylaminoethyl, N-methyl-N-hydroxyethylaminopropyl, N-methyl-N-methoxyethylaminoethyl, N-methyl-N-methoxypropylaminoethyl, N-methyl-N-methoxyethylaminopropyl, 2-methyl-2-hydroxypropyl, 3-methyl-3-hydroxybutyl, (3S)-3-aminobutyl, (3R)-3-aminobutyl, (3S)-3-hydroxybutyl or (3R)-3-hydroxybutyl.

4. The compound, or the pharmaceutically acceptable salt, the the enantiomer, a diastereomer, a hydrate, or a solvate thereof according to claim 1, wherein R¹ is selected from the group consisting of butyl, isobutyl, pentyl, isopentyl, hexyl, cyclopropylmethyl, cyclopropylethyl, cyclopropylpropyl, cyclobutylmethyl, cyclobutylethyl, cyclobutylpropyl, 4,4-dimethylpiperidin-1-ylethyl, 4,4-dimethylpiperidin-1-ylpropyl, and oxetan-3-yl.

5. The compound, or the pharmaceutically acceptable salt, the the enantiomer, a diastereomer, a hydrate, or a solvate thereof according to claim 1, wherein the halogen described in R², R³, and R⁴ is Cl or F.

6. The compound, or the pharmaceutically acceptable salt, the the enantiomer, a diastereomer, a hydrate, or a solvate thereof according to claim 1, wherein R⁵ is —H, $C_1$-$C_6$ alkyl, $C_3$-$C_6$ cycloalkyl, $C_1$-$C_3$ alkyl substituted with $C_3$-$C_6$ cycloalkyl, aryl, $C_1$-$C_3$ alkyl substituted with aryl, heteroaryl, or $C_1$-$C_3$ alkyl substituted with heteroaryl, wherein eahc of the above aryl and heteroaryl are substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl, aryloxy and methylsulfonyl; and each of the above heteroaryl is a monocyclic or bicyclic group containing 1 to 2 heteroatoms selected from the group consisting of N, O, and S, and containing 5 to 10 ring atoms.

7. The compound, or the pharmaceutically acceptable salt, the the enantiomer, a diastereomer, a hydrate, or a solvate thereof according to claim 6, wherein R⁵ is selected from the group consisting of H, methyl, ethyl, propyl, isopropyl, isopentyl, cyclopropyl, cyclobutyl, cyclopentyl, cyclohexyl, phenyl, 4-fluorophenyl, 3-fluorophenyl, 2-fluorophenyl, 4-chlorophenyl, 3-chlorophenyl, 2-chlorophenyl, 2,4-difluorophenyl, 2,5-difluorophenyl, 3,4-difluorophenyl, 2,4-dichlorophenyl, 2,5-dichlorophenyl, 3,4-dichlorophenyl, 2-fluoro-4-(trifluoromethyl)phenyl, 2-fluoro-5-(trifluoromethyl)phenyl, 3-fluoro-4-(trifluoromethyl)phenyl, 3-fluoro-5-(trifluoromethyl)phenyl, 3-(trifluoromethyl)-4-fluorophenyl, 2-fluoro-4-chlorophenyl, 2-fluoro-5-chlorophenyl, 3-fluoro-4-chlorophenyl, 3-fluoro-5-chlorophenyl, 3-chloro-4-fluorophenyl, 2-chloro-4-(trifluoromethyl)phenyl, 2-chloro-5-(trifluoromethyl)phenyl, 3-chloro-4-(trifluoromethyl)phenyl, 3-chloro-5-(trifluoromethyl)phenyl, 3-(trifluoromethyl)-4-chlorophenyl, 2-chloro-4-fluorophenyl, 2-chloro-5-fluorophenyl, 3-chloro-4-fluorophenyl, benzyl, phenethyl, 4-fluorobenzyl, naphthalen-1-yl, 3-methyl-isoxazol-5-yl, 4-phenoxyphenyl, 3-(methylsulfonyl)phenyl, 4-(methylsulfonyl)phenyl, pyridin-2-yl, pyridin-3-yl, pyridin-4-yl, 3-methoxybenzyl or 4-methoxybenzyl.

8. A compound of formula (I), or a pharmaceutically acceptable salt, an the enantiomer, a diastereomer, a hydrate, or a solvate thereof, Formula (I)

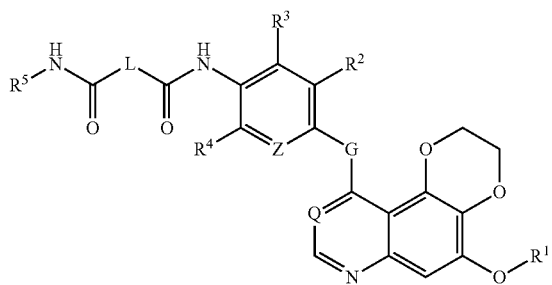

in the formula (I),
Q is CH;
G is O;
Z is CH;
L is selected from the group consisting of

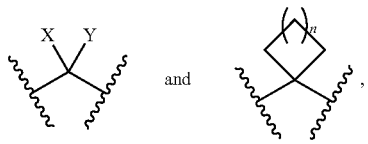

wherein X is H or $C_1$-$C_3$ alkyl; Y is H or $C_1$-$C_3$ alkyl; n is 0 to 3, and when n is 0, L represents

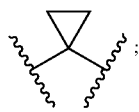

$R^1$ is $C_1$-$C_6$ alkyl substituted with 1 to 3 substituents selected from the group consisting of $C_1$-$C_3$ acyl, halogen, trifluoromethyl, cyano, —$CONH_2$, —$NR^aR^b$ and 4- to 7-membered heteroalicyclic group, wherein the 4- to 7-membered heteroalicyclic group is a 4- to 7-membered heteroalicyclic group containing 1 to 2 atoms selected from the group consisting of N, O, and S as ring atoms, and the 4- to 7-membered heteroalicyclic group is substituted with 1 to 3 substituents selected from the group consisting of halogen, $C_1$-$C_3$ alkyl, hydroxyl, —$NH_2$, and $C_1$-$C_3$ acyl, $R^a$ and $R^b$ are each independently —H, $C_1$-$C_6$ alkyl, $C_3$-$C_6$ cycloalkyl, $C_1$-$C_6$ alkyl substituted with $C_1$-$C_3$ alkoxy, $C_1$-$C_6$ alkyl substituted with $C_1$-$C_3$ alkylthio, $C_1$-$C_6$ alkyl substituted with substituted amino or unsubstituted amino, wherein the substituted amino is substituted with mono- or di-$C_1$-$C_3$ alkyl;

$R^2$, $R^3$, and $R^4$ are each independently H, $C_1$-$C_3$ alkyl or halogen;

$R^5$ is —H, $C_1$-$C_9$ alkyl, $C_3$-$C_7$ cycloalkyl, $C_1$-$C_6$ alkyl substituted with $C_3$-$C_7$ cycloalkyl, aryl, $C_1$-$C_6$ alkyl substituted with aryl, heteroaryl, or $C_1$-$C_6$ alkyl substituted with heteroaryl;

each of the above aryl and heteroaryl are unsubstituted, or are substituted with 1 to 3 substituents selected from the group consisting of one or more of the following: hydroxyl, amino, cyano, $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl, and methylsulfonyl; and each of the above heteroaryl is a monocyclic or bicyclic group containing 1 to 3 heteroatoms selected from the group consisting of N, O, and S and containing 5 to 10 ring atoms.

9. The compound, or the pharmaceutically acceptable salt, the the enantiomer, a diastereomer, a hydrate, or a solvate thereof according to claim 8, wherein $R^1$ is $C_1$-$C_6$ alkyl substituted with 1 to 3 substituents selected from the group consisting of $C_1$-$C_3$ acyl, —F, trifluoromethyl, cyano, —$CONH_2$, —$NR^aR^b$ or 4- to 7-membered heteroalicyclic group, wherein the 4- to 7-membered heteroalicyclic group is a 4- to 7-membered heteroalicyclic group containing 1 to 2 atoms selected from the group consisting of N, O, and S as ring atoms, and the 4- to 7-membered heteroalicyclic group is substituted with 1 to 3 substituents selected from the group consisting of —F, $C_1$-$C_3$ alkyl, hydroxyl, —$NH_2$, and $C_1$-$C_3$ acyl, $R^a$ and $R^b$ are each independently —H, $C_1$-$C_3$ alkyl, $C_3$-$C_6$ cycloalkyl, $C_1$-$C_3$ alkyl substituted with $C_1$-$C_3$ alkoxy, $C_1$-$C_3$ alkyl substituted with $C_1$-$C_3$ alkylthio, $C_1$-$C_3$ alkyl substituted with substituted amino or unsubstituted amino, wherein the substituted amino is substituted with mono- or di-$C_1$-$C_3$ alkyl;

$R^2$, $R^3$ and $R^4$ are each independently —H, —F or —Cl;

$R^5$ is —H, aryl, $C_1$-$C_3$ alkyl substituted with aryl, heteroaryl, or $C_1$-$C_3$ alkyl substituted with heteroaryl, wherein each of the above aryl and heteroaryl are unsubstituted, or are substituted with 1 to 3 substituents selected from the group consisting of one or more of the following: hydroxyl, amino, cyano, $C_1$-$C_3$ alkyl, $C_1$-$C_3$ alkoxy, $C_1$-$C_3$ alkylthio, amino substituted with mono- or di-$C_1$-$C_3$ alkyl, halogen, trifluoromethyl and methylsulfonyl; and each of the above heteroaryl is a monocyclic or bicyclic group containing 1 to 2 heteroatoms selected from the group consisting of N, O, and S, and containing 5 to 10 ring atoms.

10. A pharmaceutical composition, consisting of the compound of formula (I), or the pharmaceutically acceptable salt, the enantiomer, a diastereomer, a hydrate, or a solvate thereof according to claim 1 and pharmaceutically acceptable carrier(s) or excipient(s).

11. A method of inhibiting VEGFR-2 and/or c-MET tyrosine kinase in a subject, comprising administering to the subject the compound of formula (I), or the pharmaceutically acceptable salt, the the enantiomer, a diastereomer, a hydrate, or a solvate thereof according to claim 1.

12. The compound, or the pharmaceutically acceptable salt, the the enantiomer, a diastereomer, a hydrate, or a solvate thereof according to claim 1, wherein:
Q is CH;
G is O;
Z is CH;
L represents

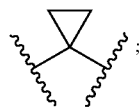

$R^1$ is $C_1$-$C_6$ alkyl, or $C_1$-$C_6$ alkyl substituted with 4- to 7-membered heterocyclyl;
the above 4- to 7-membered heterocyclyl is a 4- to 7-membered heterocyclyl containing 1 to 2 atoms selected from the group consisting of N, O, and S, which is unsubstituted, or is substituted with $C_1$-$C_3$ alkyl or $C_1$-$C_3$ acyl, or is oxidized by 1 to 2 oxygen atoms;

$R^2$ is H or halogen;

$R^3$ is H or halogen;

$R^4$ is H or halogen;

$R^5$ is aryl, wherein the aryl is unsubstituted, or substituted with one or more halogen.

13. The compound, or the pharmaceutically acceptable salt, the the enantiomer, a diastereomer, a hydrate, or a solvate thereof according to claim 12, wherein: $R^1$ is $C_1$-$C_6$ alkyl, or $C_1$-$C_3$ alkyl substituted with 5- to 6-membered heterocyclyl, the above 5- to 6-membered heterocyclyl is a 5- to 6-membered heterocyclyl containing 1 to 2 atoms selected from the group consisting of N, O, and S.

14. The compound, or the pharmaceutically acceptable salt, the the enantiomer, a diastereomer, a hydrate, or a solvate thereof according to claim 12, wherein: $R^1$ is selected from the group consisting of one or more of the following: methyl, ethyl, propyl, isopropyl, tetrahydropyrrol-1-ylethyl, tetrahydropyrrol-1-ylpropyl, piperidin-1-ylethyl, piperidin-1-ylpropyl, piperazin-1-ylethyl, piperazin-1-ylpropyl, morpholin-4-ylethyl, morpholin-4-ylpropyl, methylpiperazin-4-ylethyl, methylpiperazin-4-ylpropyl, N-formylpiperazin-4-ylethyl, N-formylpiperazin-4-ylpropyl, N-acetylpiperazin-4-ylethyl, N-acetylpiperazin-4-ylpropyl, (1,1-dioxothiomorpholin)-4-ylethyl, and (1,1-dioxothiomorpholin)-4-ylpropyl.

15. A compound, or a pharmaceutically acceptable salt, an the enantiomer, a diastereomer, a hydrate, or a solvate thereof, wherein the compound is selected from the group consisting of:

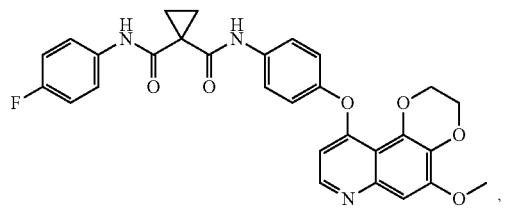
,

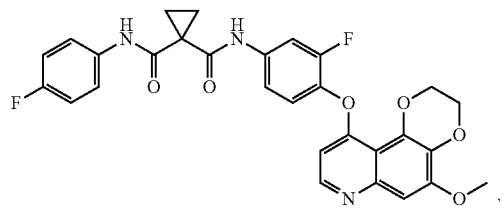
,

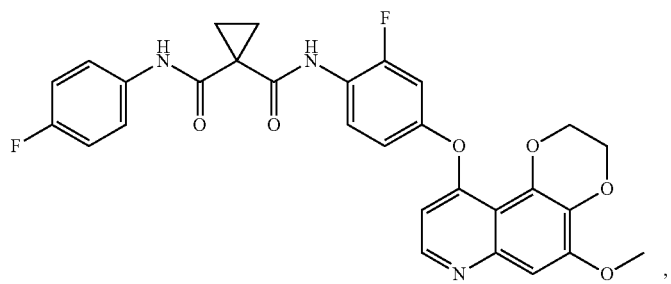
,

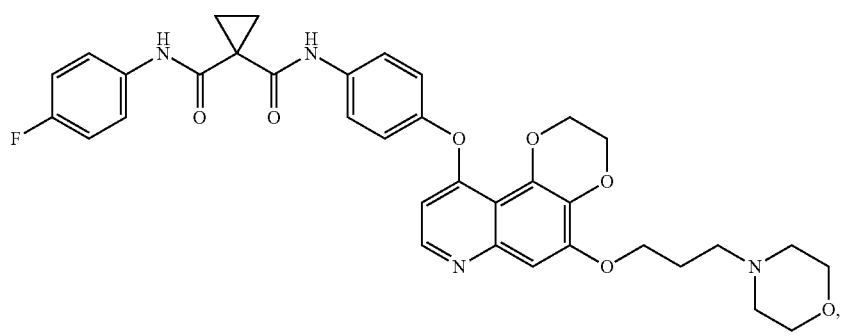
,

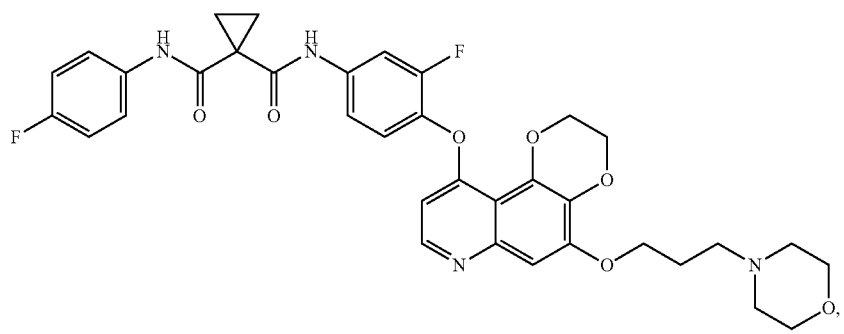
,

-continued
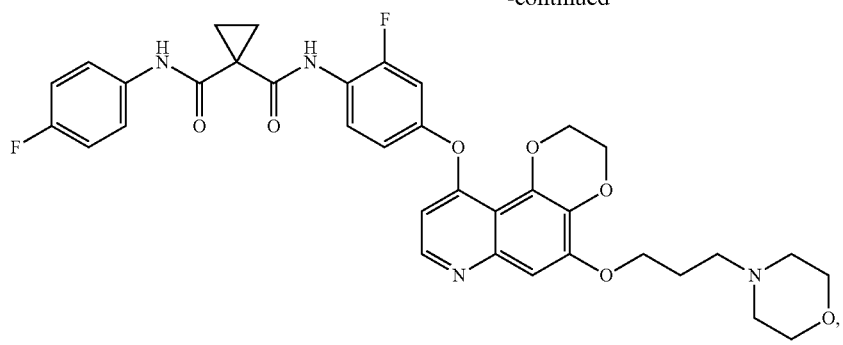
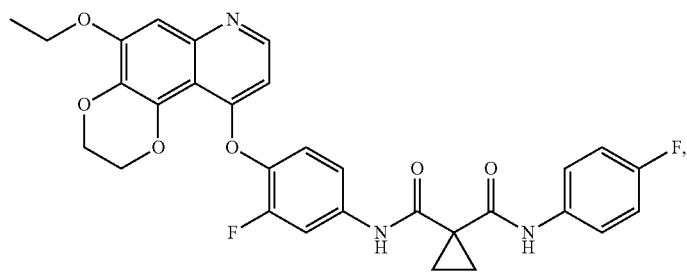
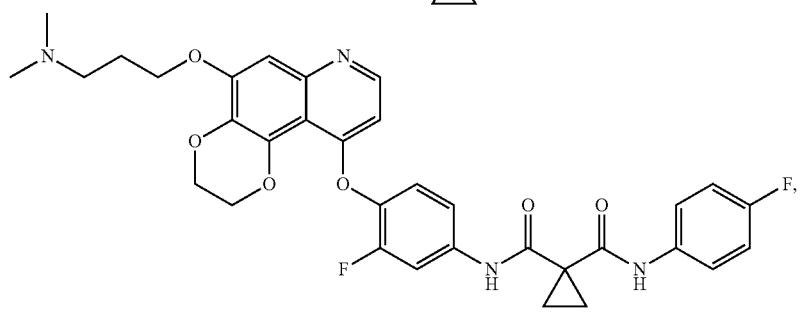
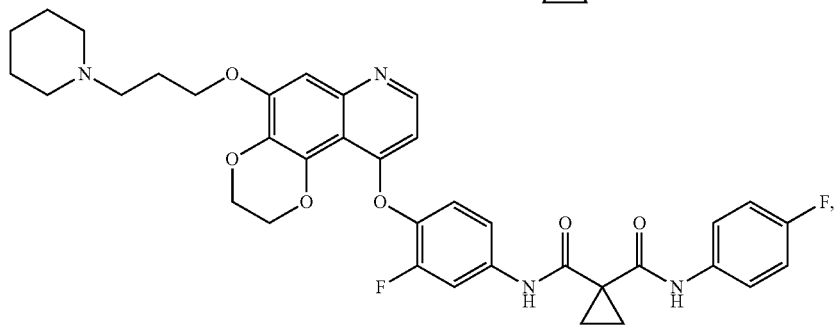
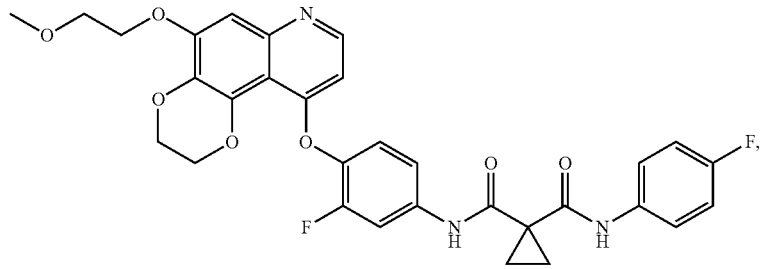
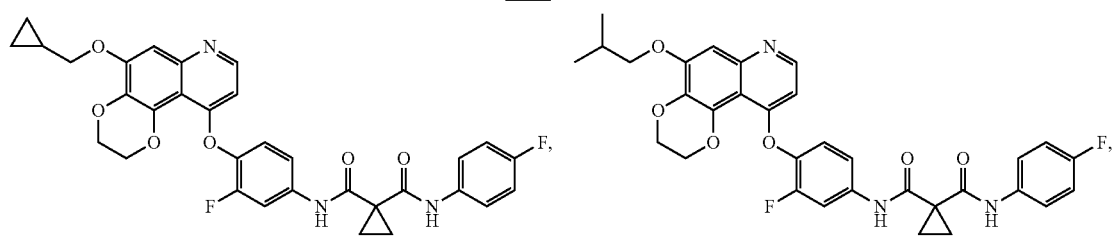

-continued
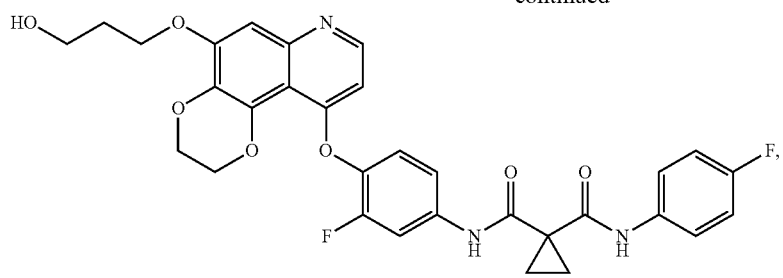
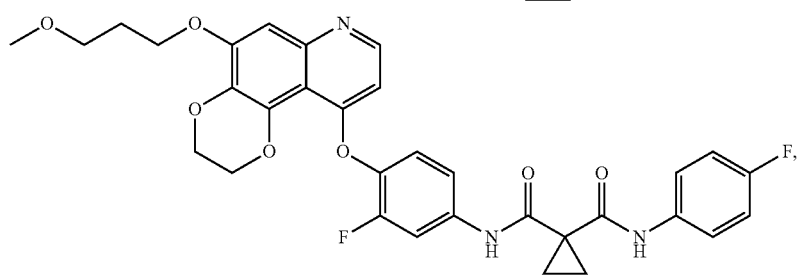
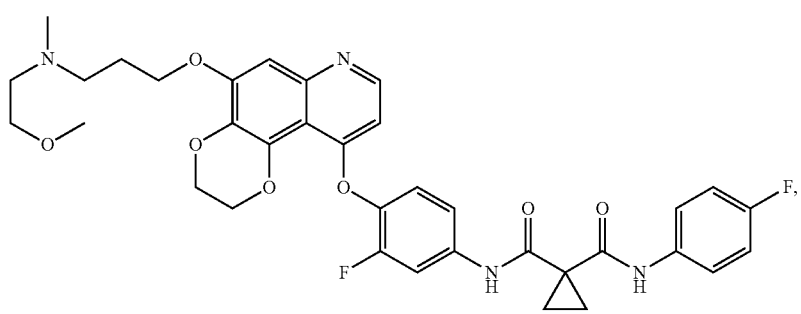
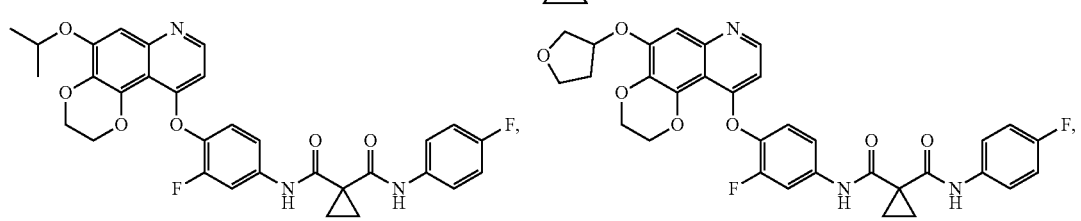
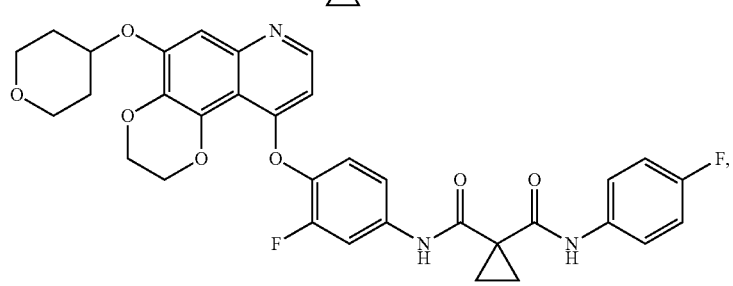
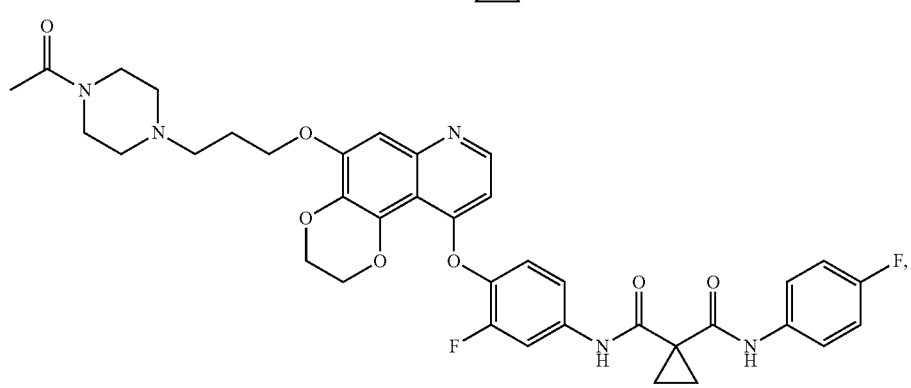

-continued
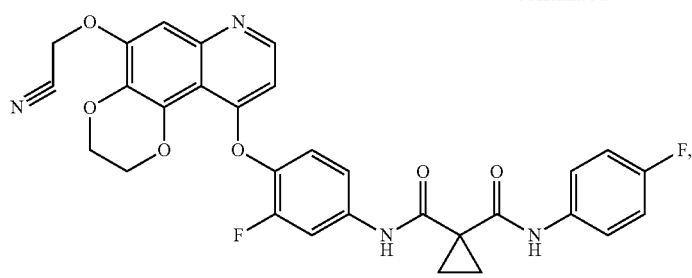
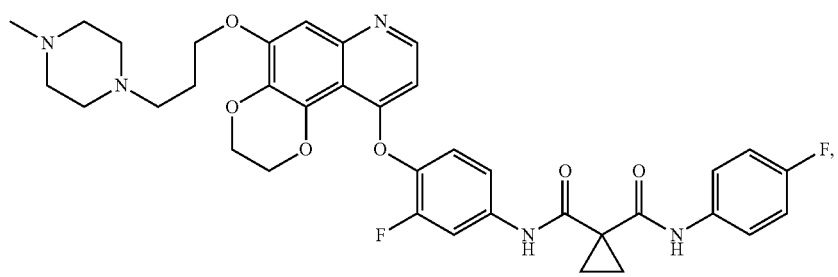
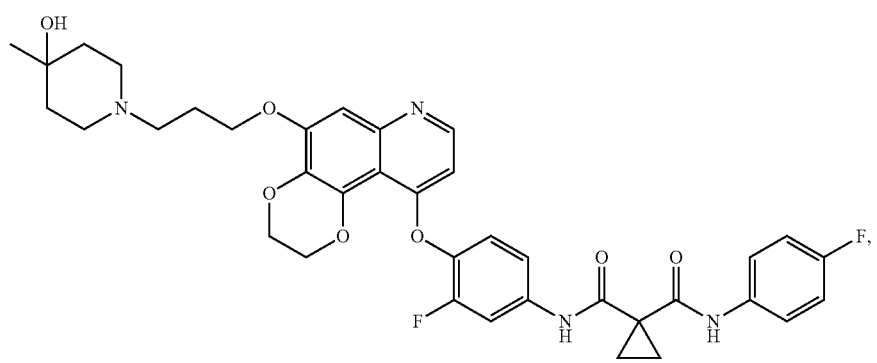
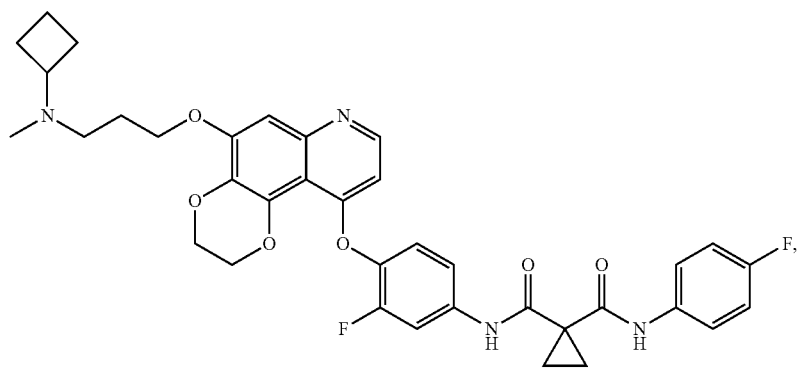
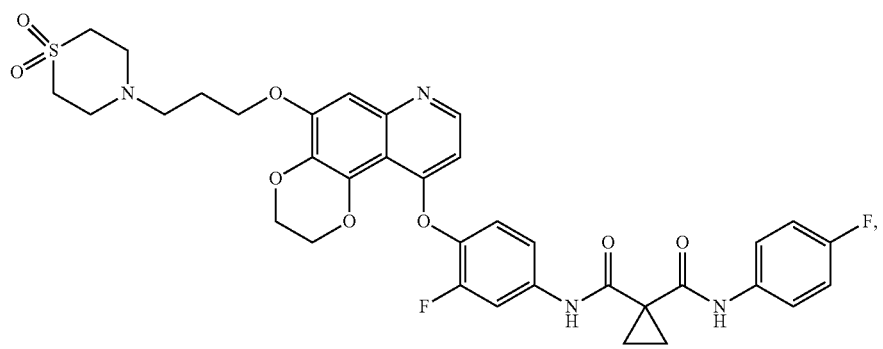

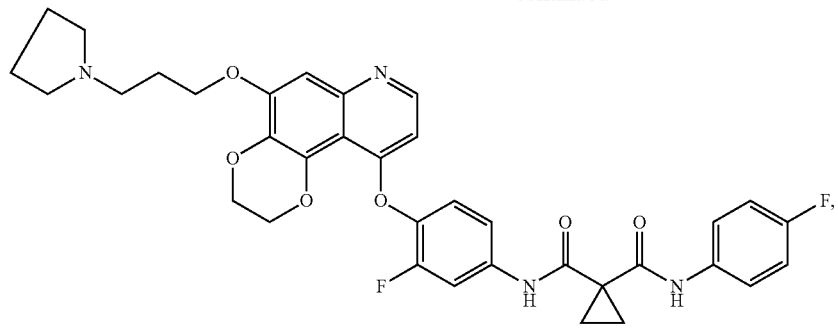
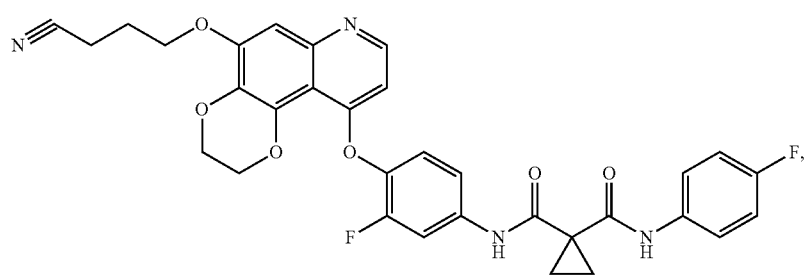
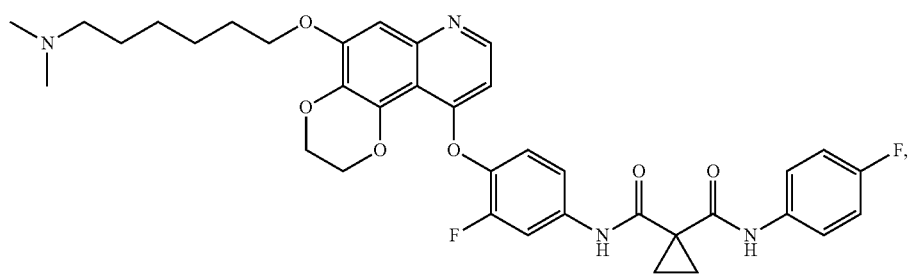
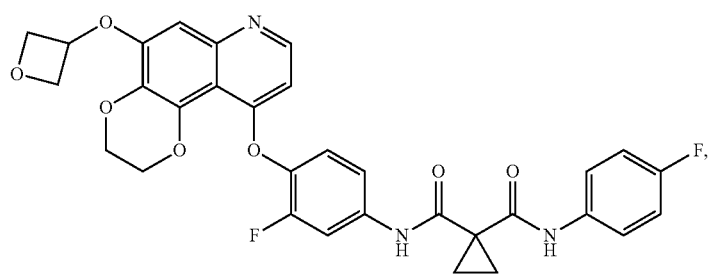
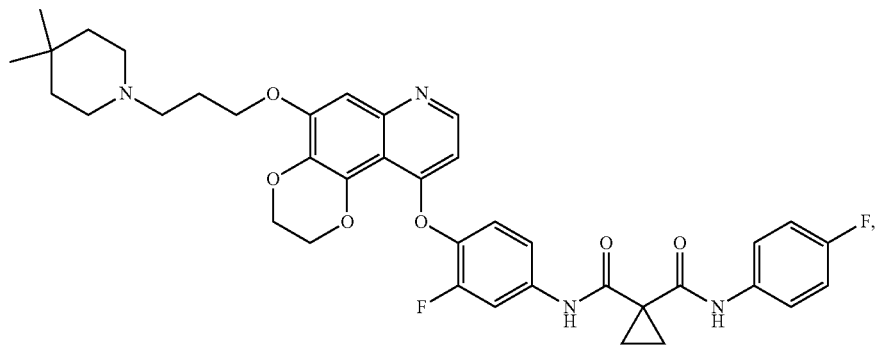

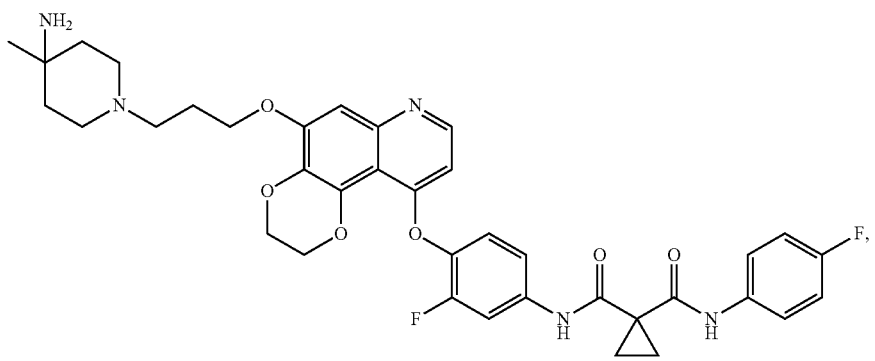
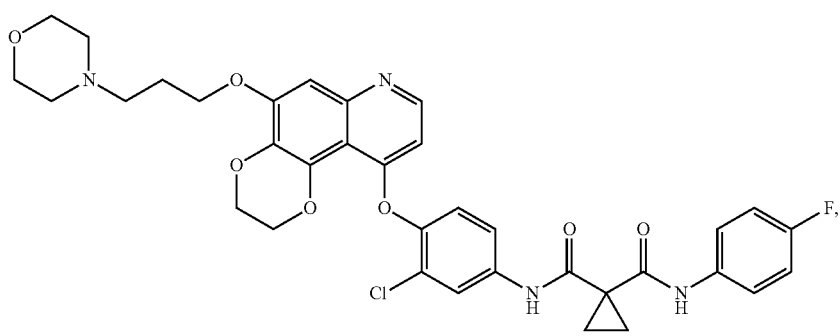
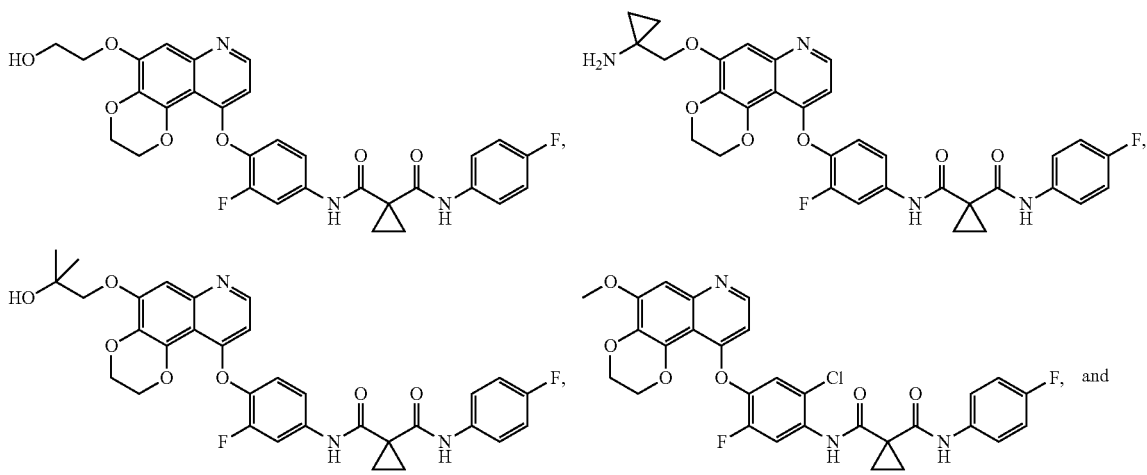
and
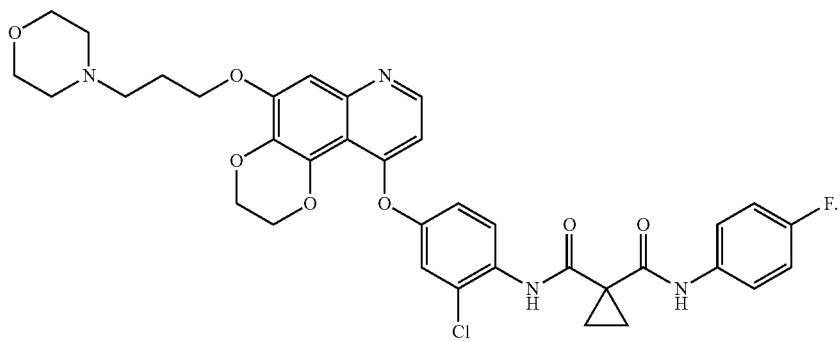

16. The compound according to claim 15, wherein the compound has the following structure:

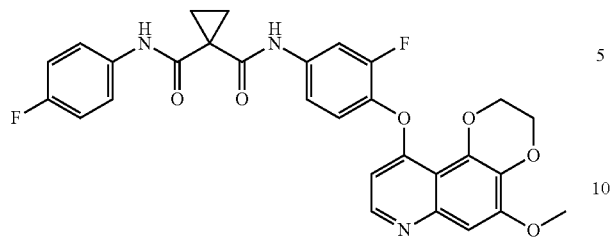

or the pharmaceutically acceptable salt thereof.

17. The compound according to claim 15, wherein the compound has the following structure:

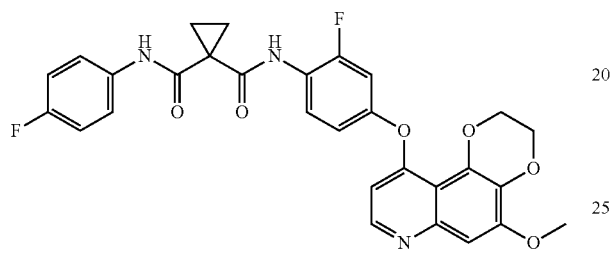

or the pharmaceutically acceptable salt thereof.

18. The compound according to claim 15, wherein the compound has the following structure:

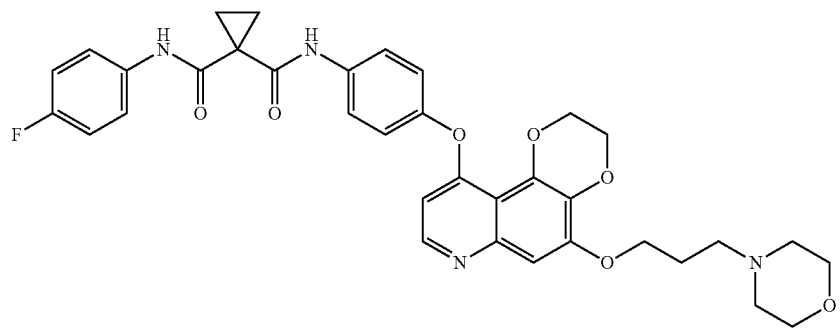 [SMILES: O=C(Nc1ccc(F)cc1)C1(C(=O)Nc2ccc(Oc3ccnc4cc(OCCCN5CCOCC5)c5c(c34)OCCO5)cc2)CC1]

or the pharmaceutically acceptable salt thereof.

19. The compound according to claim 15, wherein the compound has the following structure:

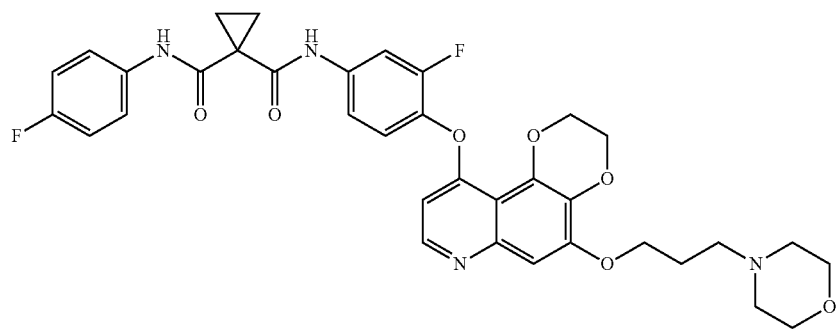 [SMILES: O=C(Nc1ccc(F)cc1)C1(C(=O)Nc2ccc(Oc3ccnc4cc(OCCCN5CCOCC5)c5c(c34)OCCO5)c(F)c2)CC1]

or the pharmaceutically acceptable salt thereof.

20. The compound according to claim 15, wherein the compound has the following structure:

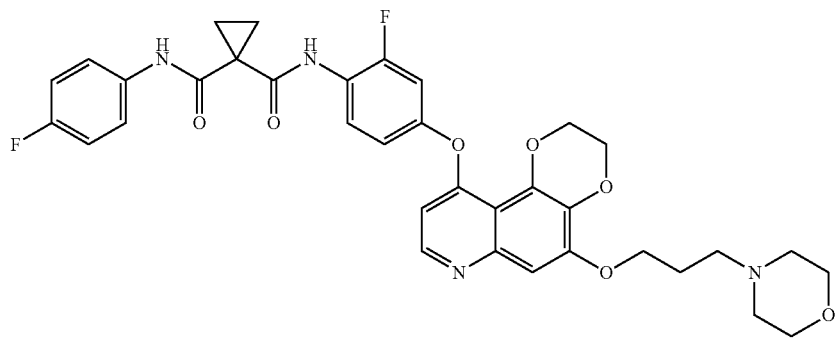 [SMILES: O=C(Nc1ccc(F)cc1)C1(C(=O)Nc2ccc(Oc3ccnc4cc(OCCCN5CCOCC5)c5c(c34)OCCO5)cc2F)CC1]

or the pharmaceutically acceptable salt thereof.

21. The compound, or the pharmaceutically acceptable salt, the enantiomer, or the diastereomer thereof according to claim 1.

22. The compound, or the pharmaceutically acceptable salt, the enantiomer, or the diastereomer thereof according to claim 8.

23. The compound, or the pharmaceutically acceptable salt, the enantiomer, or the diastereomer thereof according to claim 15.

* * * * *

UNITED STATES PATENT AND TRADEMARK OFFICE
CERTIFICATE OF CORRECTION

| | |
|---|---|
| PATENT NO. | : 11,407,760 B2 |
| APPLICATION NO. | : 16/968797 |
| DATED | : August 9, 2022 |
| INVENTOR(S) | : Qiang Zhang et al. |

It is certified that error appears in the above-identified patent and that said Letters Patent is hereby corrected as shown below:

In the Claims

Column 57, Claim number 2, Line number 40, replace "a diastereomer, a hydrate, or a solvate thereof" with "the diastereomer, the hydrate, or the solvate thereof".

Column 57, Claim number 3, Line number 56, replace "a diastereomer, a hydrate, or a solvate thereof" with "the diastereomer, the hydrate, or the solvate thereof".

Column 58, Claim number 4, Line number 18, replace "the the enantiomer, a diastereomer, a hydrate, or a solvate thereof" with "the enantiomer, the diastereomer, the hydrate, or the solvate thereof".

Column 58, Claim number 5, Line number 26, replace "the the enantiomer, a diastereomer, a hydrate, or a solvate thereof" with "the enantiomer, the diastereomer, the hydrate, or the solvate thereof".

Column 58, Claim number 6, Line number 30, replace "the the enantiomer, a diastereomer, a hydrate, or a solvate thereof" with "the enantiomer, the diastereomer, the hydrate, or the solvate thereof".

Column 58, Claim number 7, Line number 43, replace "the the enantiomer, a diastereomer, a hydrate, or a solvate thereof" with "the enantiomer, the diastereomer, the hydrate, or the solvate thereof".

Column 60, Claim number 9, Line number 6, replace "the the enantiomer, a diastereomer, a hydrate, or a solvate thereof" with "the enantiomer, the diastereomer, the hydrate, or the solvate thereof".

Column 60, Claim number 10, Line number 41, replace "a diastereomer, a hydrate, or a solvate thereof" with "the diastereomer, the hydrate, or the solvate thereof".

Signed and Sealed this
Third Day of December, 2024

Katherine Kelly Vidal
*Director of the United States Patent and Trademark Office*

Column 60, Claim number 11, Line number 47, replace "the the enantiomer, a diastereomer, a hydrate, or a solvate thereof" with "the enantiomer, the diastereomer, the hydrate, or the solvate thereof".

Column 60, Claim number 12, Line number 49, replace "the the enantiomer, a diastereomer, a hydrate, or a solvate thereof" with "the enantiomer, the diastereomer, the hydrate, or the solvate thereof".

Column 61, Claim number 13, Line number 10, replace "the the enantiomer, a diastereomer, a hydrate, or a solvate thereof" with "the enantiomer, the diastereomer, the hydrate, or the solvate thereof".

Column 62, Claim number 14, Line number 2, replace "the the enantiomer, a diastereomer, a hydrate, or a solvate thereof" with "the enantiomer, the diastereomer, the hydrate, or the solvate thereof".

Column 62, Claim number 15, Line number 14, replace "an the enantiomer" with "an enantiomer".